(12) United States Patent
Gangjee

(10) Patent No.: US 6,537,999 B2
(45) Date of Patent: *Mar. 25, 2003

(54) PYRIMIDINE DERIVATIVES AND METHODS OF MAKING AND USING THESE DERIVATIVES

(75) Inventor: Aleem Gangjee, Allison Park, PA (US)

(73) Assignee: Duquesne University of the Holy Ghost, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/803,510

(22) Filed: Mar. 9, 2001

(65) Prior Publication Data

US 2002/0052384 A1 May 2, 2002

Related U.S. Application Data

(62) Division of application No. 09/315,762, filed on May 20, 1999, which is a continuation-in-part of application No. 09/073,593, filed on May 6, 1998, now Pat. No. 5,958,930, which is a continuation of application No. 09/190,374, filed on Nov. 12, 1998, now Pat. No. 6,096,750, which is a continuation of application No. 08/660,023, filed on Jun. 6, 1996, now Pat. No. 5,939,420.

(51) Int. Cl.$^7$ .................. C07D 487/04; C07D 491/048; A61K 31/519; A61K 33/02; A61K 33/08
(52) U.S. Cl. .................... 514/265.1; 546/289; 546/309; 544/250; 544/253; 544/278; 544/279; 544/280
(58) Field of Search .......................... 544/280; 514/258

(56) References Cited

U.S. PATENT DOCUMENTS

| | | | |
|---|---|---|---|
| 3,904,624 A | 9/1975 | Perronnet et al. | 260/251 |
| 4,435,570 A | 3/1984 | Nishimura et al. | 544/280 |
| 4,923,872 A | 5/1990 | Kostlan et al. | 514/258 |
| 4,996,206 A | 2/1991 | Taylor et al. | 514/258 |
| 5,028,608 A | 7/1991 | Taylor et al. | 514/258 |
| 5,196,424 A * | 3/1993 | Gossett et al. | 514/258 |
| 5,248,775 A | 9/1993 | Taylor et al. | 544/280 |
| 5,254,687 A | 10/1993 | Taylor | 544/280 |
| 5,344,932 A | 9/1994 | Taylor | 544/280 |
| 5,346,900 A | 9/1994 | Gangjee | 514/258 |
| 5,508,281 A | 4/1996 | Gangjee | 514/258 |
| 5,877,178 A * | 3/1999 | Gangjee | 514/258 |
| 5,958,930 A * | 9/1999 | Gangjee | 514/258 |

OTHER PUBLICATIONS

Kuyper et al. Pyrrolo[2,3–d]pyrimidines as conformationally restricted analogs of the antibacterial agent trimethoprim. Bioorg. Med. Chem. 4, 593–603, 1996. Abstract.*

Hurlbert, B.S., et al., "Studies in Condensed Pyrimidine Systems. XXIII. Synthesis of 2,4–Diaminopyrido[2,3–d] pyrimidines from 6–Keto Esters", *J. Med. Chem.*, vol. 11, pp. 703–707 (1968).

(List continued on next page.)

*Primary Examiner*—Mark Berch
(74) *Attorney, Agent, or Firm*—Debra Z. Anderson; Eckert Seamans Cherin & Mellott, LLC

(57) ABSTRACT

This invention discloses pyrimidine derivatives, and pharmaceutically acceptable salts and prodrugs thereof, of the following formula:

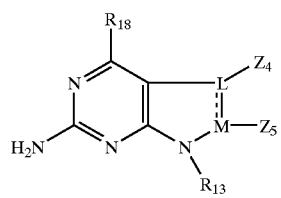

wherein L and M are selected from the group consisting of carbon and CH, the chemical bond between L and M is selected from the group consisting of a single bond and a double bond, wherein $Z_4$ and $Z_5$ are different and are selected from the group consisting of $R_{14}$ and

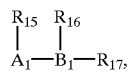

where $Z_4$ is $R_{14}$ when $Z_5$ is

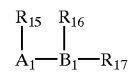

and $Z_4$ is

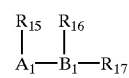

when $Z_5$ is $R_{14}$;
wherein $A_1$ is CH;
wherein $B_1$ is CH;
wherein $R_{17}$ is selected from the group consisting of aryl, diaryl, triaryl, mono-, di- or tri-substituted aryl, mono-, di- or tri-substituted diaryl, mono-, di- or tri- substituted triaryl, a substituted or unsubstituted heteroaryl and p-aroyl-L-glutamate;
wherein $R_{18}$ is a lower akyl group; and
said compound capable of inhibiting dihydrofolate reductase and thymidylate synthase. These compounds are useful in the treatment of certain illnesses, including cancer and secondary infections caused by *Pneumocystis carinii* and *Toxoplasmosis gondii* in immunocompromised patients.

21 Claims, 24 Drawing Sheets

OTHER PUBLICATIONS

Hurlbert, B.S., and Valenti, B.F., "Studies on Condensed Pyrimidine Systems. XXIV. The Condensation of 2,4,6–Triaminopyrimidine with Malondialdehyde Derivatives", *J. Med. Chem.*, vol. 11, pp. 708–710 (1968).

Hurlbert, B.S., et al., "Studies on Condensed Pyrimidine Systems. XXV. 2,4–Diaminopyrido[2,3–d]pyrimidines. Biological Data", *J. Med. Chem.*, vol. 11, pp. 711–717 (1968).

Grivsky, E.M., et al., "Synthesis and Antitumor Activity of 2,4–Diamino–6–(2,5–dimethoxybenzyl)–5–methylpyrido [2,3–d]pyrimidine", *J. Med. Chem.*, vol. 23, pp. 327–329 (1980).

Elsager, E. F., et al., "Folate Antagonists. 20. Synthesis and Antitumor and Antimalarial Properties of Trimetrexate and Related 6–[(phenylamino)methyl]–2,4–quinazolinediamines", *J. Med. Chem.*, vol. 26, pp. 1753–1760 (1983).

Nishimura, S. and Akimoto, H., *Chem. Abstracts*, C.A. vol. 99:70481a (1983).

Piper, J.R., et al., "Syntheses and Antifolate Activity of 5–Methyl–5–deaza Analogues of Aminopterin, Methotrexate, Folic Acid, and N–10–Methylfolic Acid", *J. Med. Chem.*, vol. 29, pp. 1080–1087 (1986).

Werbel, L.M., et al., "Synthesis and Antimalarial Activity of a Series of 2,4–Diamino–6–[(N–alkylanilino)methyl] quinazolines", *J. Heterocyclic Chem.*, vol. 24, pp. 345–349 (1987).

Miwa, T. et al., "Novel Pyrrolo[2,3–d]pyrimidine Antifolates: Synthesis and Antitumor Activities",*J. Med. Chem.*, 1991, pp. 555–560, vol. 34, No. 2.

Taylor, E.C., et al., "A Dideazatetrahydrofolate Analogue Lacking a Chiral Center at C–6, N–[4–[2–(2–Amino–3, 4–dihydro–4–oxo–7H–pyrrolo[2,3–d] pyrimidin–5–yl)ethyl]benzoyl]–L–glutamic Acid, Is an Inhibitor of Thymidylate Synthase", *J. Med. Chem*, vol. 35, pp. 4450–4454 (1992).

Gangjee, A., et al., "Classical and Nonclassical Furo[2,3–d] pyrimidines as Novel Antifolates: Synthesis and Biological Activities", *J. Med. Chem.*, 1994, pp. 1169–1176, vol. 37, No. 8.

Gangjee, A., et al., "Novel 2,4–Diamino–5–Substituted–pyrrolo[2,3–d]pyrimidines as Classical and Nonclassical Antifolate Inhibitors of Dihydrofolate Reductases",*J. Med. Chem.*, pp. 2158–2165, vol. 38, No. 12, (1995).

Gangjee, A., et al., "Effect of Bridge Region Variation on Antifolate and Antitumor Activity of Classical 5–Substituted 2,4–Diaminofuro[2,3–d]pyrimidines",*J. Med. Chem.*, 1995, pp. 3798–3805, vol. 38, No. 19.

Gangjee A., et al:, "2,4–Diamino–5–deaza–6–Substituted Pyrido{2,3–d pyrimidine Antifolates as Potent and Selective Nonclassical Inhibitors of Dihydrofolate Reductases", *J. Med. Chem.* 1996, vol. 39, No. 7, pp. 1438–1446.

Badawey, A.M., "Synthesis and in vitro Evaluation of Some New Pyrimidines and Related Condensed Ring Systems as Potential Anticancer Agents",*J. Heterocyclic Chem.* 33:229 (1996).

Hoops, G.C., et al., "The Synthtesis and Determination of Acidic Ionization Constants of Certain 5–Substituted 2–Aminopyrrolo[2,3–d]pyrimidin–4–ones and Methylated Analogs", *J. Heterocyclic Chem.* 33:767 (1996).

Meade, E.A. and Beauchamp, L.M., "The Synthesis of 4–Benzylamino–6–methyl–1H–pyrrolo[3,2–c]pyridine and 4–Benzylamino–6–methyl–1H–pyrrolo[3,2–b]pyridine", *J. Heterocyclic Chem.* 33:303 (1996).

Gangjee, A., et al., "5–Arylthio–Substituted 2–Amino–4–oxo–6–methylpyrrolo[2,3–d]pyrimidine Antifolates as Thymidllate Synthase Inhibitors and Antitumor Agents",*J. Med. Chem.*, 1995, pp. 4495–4502, vol. 38, No. 22.

Gangjee, A., et al., "2–Amino–4–oxo–5–substituted–pyrrolo [2,3–d]pyrimidines as Nonclassical Antifolate Inhibitors of Thymidlylate Synthase", *J. Med. Chem.*, 1996, pp. 4563–4568, vol. 39, No. 23.

Gangjee, A., et al., "Classical and Nonclassical Antifolates as Potential Antitumor, Antipneumocystis and Antitoxoplasma Agents", *Current Pharmaceutical Design*, 1996, pp. 263–280, vol. 2.

Gangjee, A., et al., "Effect of $N^9$–Methylation and Bridge Atom Variation on the Activity of 5–Substituted 2,4–Diaminopyrrolo[2,3–d]pyrimidines against Dihydrofolate Reductase from *Pneumocystis carinii* and *Toxoplasma gondii*", *J. Med. Chem.*, 1997, pp. 1173–1177, vol. 40.

Cody, V., et al., "Comparison of Ternary Complexes of *Pneumocystis carinii* and Wild–Type Human Dihydrofolate Reductase with Coenzyme NADPH and a Novel Classical Antitumor Furo[2,3–d]pyrimidine Antifolate", *Acta. Cryst.*, 1997, pp. 638–649, vol. D53.

Shih, C., et al., "LY231514, a Pyrrolo[2,3–d]pyrimidine––based Antifolate that Inhibits Multiple Folate–requiring Enzymes", *Cancer Research*, Mar. 15, 1997, pp. 1116–1123, vol. 57.

Gangjee, A., et al., "Synthesis and Biological Activities of Tricyclic Conformationally Restricted Tetrahydropyrido Annulated Furo[2,3–d]pyrimidines as Inhibitors of Dihydrofolate Reductases", *J. Med. Chem.*, 1998, pp. 1409–1416, vol. 41.

Gangjee, A., et al., "Selective *Pneumocystis carinii* Dihydrofolate Reductase Inhibitors: Design, Synthesis, and Biological Evaluation of New 2,4–Diamino–5–substituted–furo [2,3–d]pyrimidines", *J. Med. Chem.*, 1998, pp. 1263–1271, vol. 44, No. 8.

Gangjee, A., et al., presented at the 217 ACS National Meeting, Anaheim, CA, Mar. 21–25, 1999, Abstract No. MEDI 049.

\* cited by examiner

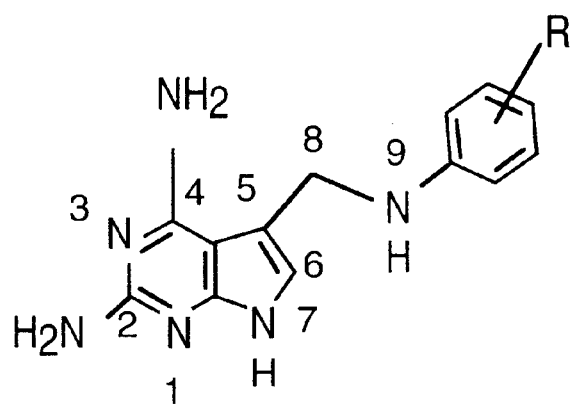
1: R=3',4',5' -(OCH3)3
2: R=3',4' -(OCH3)2
3: R=4' -(OCH3)
4: R=2',5' -(OCH3)2
5: R=2',5' -(OC2H5)2
6: R=3',4'-(Cl)2
7: R=2',3' -(CH)4
8: R=H
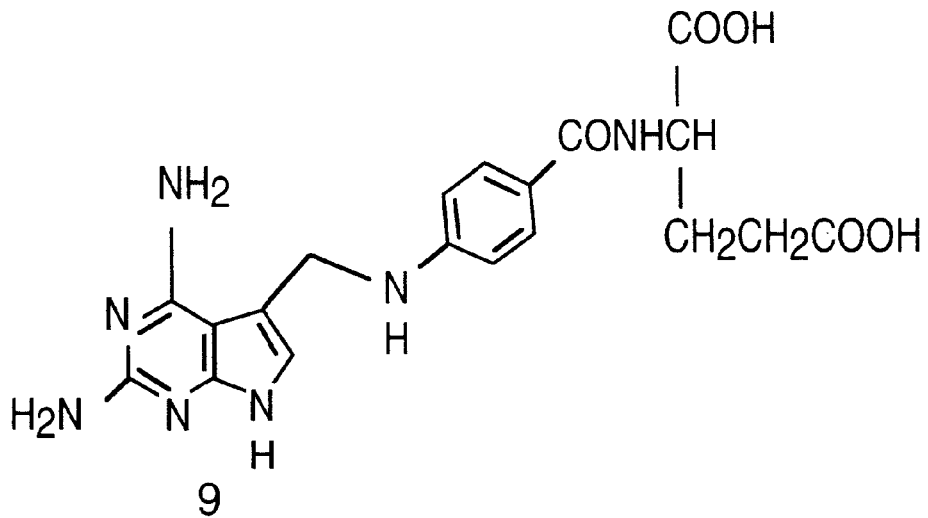
FIG. 2

(A): Raney Ni/HCOOH; (B): NaBH3; (C): 30% HBr-AcOH; (D): DMF; (E): NaH/DMF

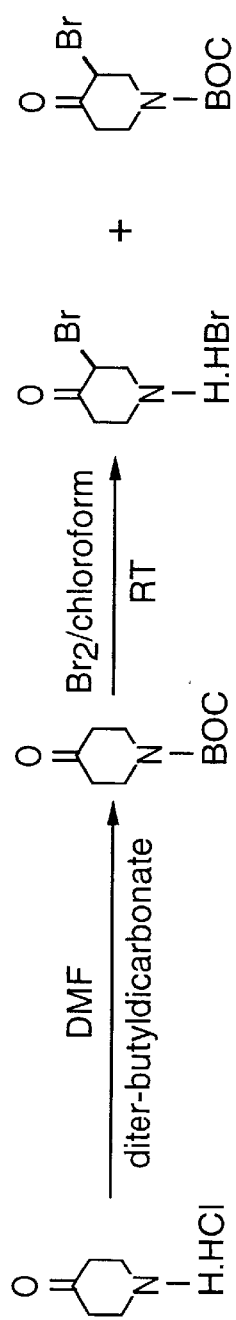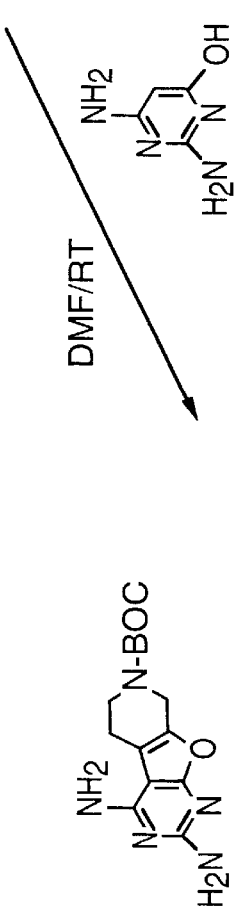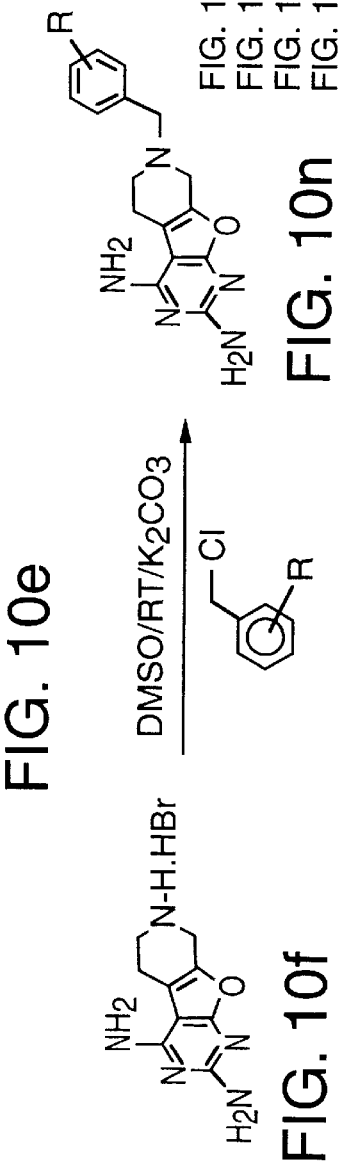
FIG. 10a  
FIG. 10b  
FIG. 10c  
FIG. 10d  
FIG. 10e  
FIG. 10f  
FIG. 10n  
FIG. 10g R=H
FIG. 10h R=3,4,5 trimethoxy
FIG. 10i R=3,5 dimethoxy
FIG. 10j R=2,4 dichloro
FIG. 10k R=3,4 dichloro
FIG. 10l R=2,6 dichloro
FIG. 10m R=—CONHCH₂CH₂CH₂COOH $R_1$ = H, $R_2$ = 3',4'-diOMe
$R_1$ = H, $R_2$ = H
$R_1$ = H, $R_2$ = 2',5'-diOMe
$R_1$ = H, $R_2$ = 4'-Cl
$R_1$ = H, $R_2$ = 2'-OMe
$R_1$ = H, $R_2$ = 4'-OMe
$R_1$ = H, $R_2$ = 3',4',5'-triOMe
$R_1$ = CH$_3$, $R_2$ = 3',4',5'-triOMe
$R_1$ = CH$_3$, $R_2$ = 2',5'-diOMe
$R_1$ = CH$_3$, $R_2$ = 3',4'-diOMe
$R_1$ = CH$_3$, $R_2$ = 3',4',5'-triOMe
$R_1$ = CH$_3$, $R_2$ = H
$R_1$ = H, $R_2$ = 3',4'-C$_4$H$_4$
$R_1$ = CH$_3$, $R_2$ = 3',4'-C$_4$H$_4$
$R_1$ = CH$_3$, $R_2$ = 2',3'-C$_4$H$_4$

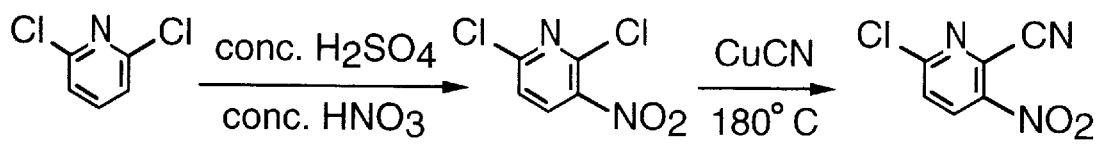
FIG. 12a
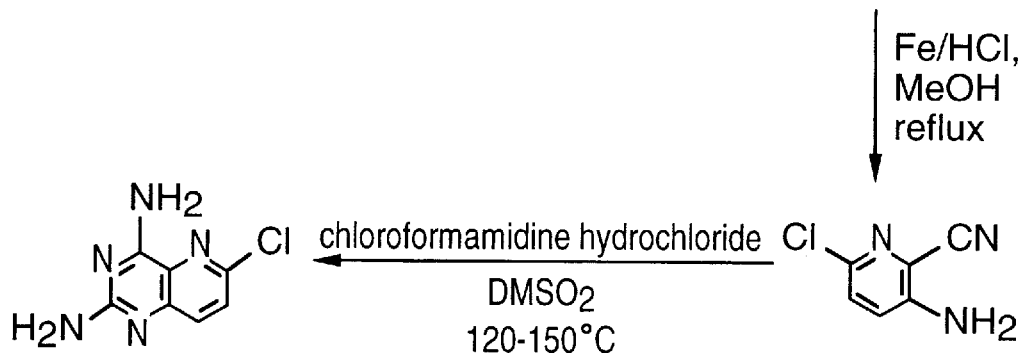
FIG. 12c
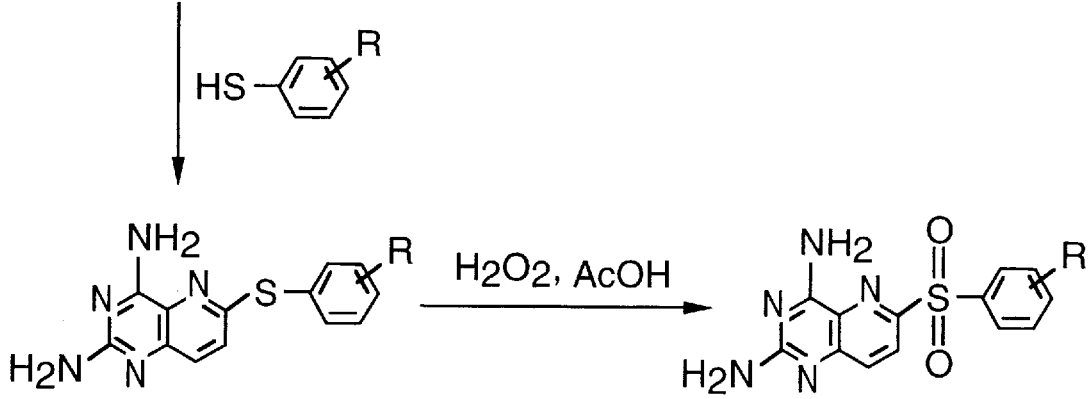
FIG. 12d
FIG. 12e
FIG. 12f R=4'-OMe
FIG. 12g R=3',4'-OMe
FIG. 12h R=2'-OMe
FIG. 12i R=4'-OMe
FIG. 12j R=3',4'-OMe
FIG. 12k R=2'-OMe

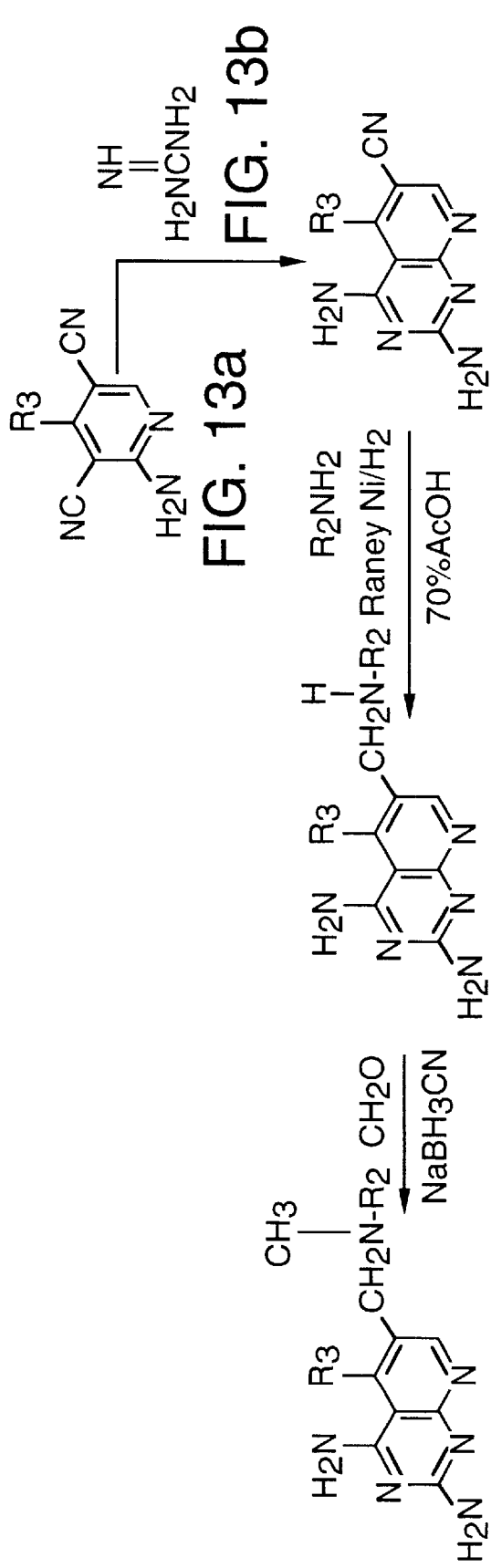

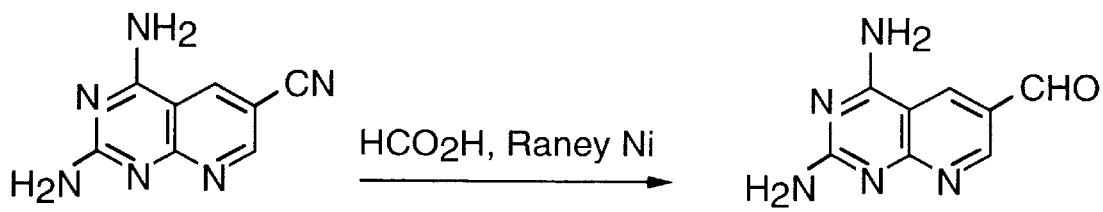
FIG. 14a  →  FIG. 14b
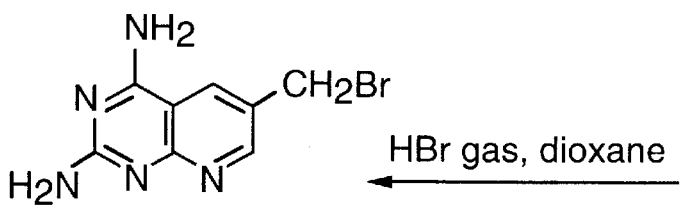
FIG. 14d  ←  FIG. 14c
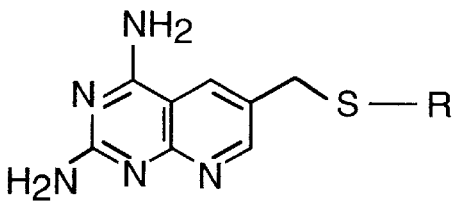
FIG. 14e  R = Phenyl
FIG. 14f  R = Napthylene

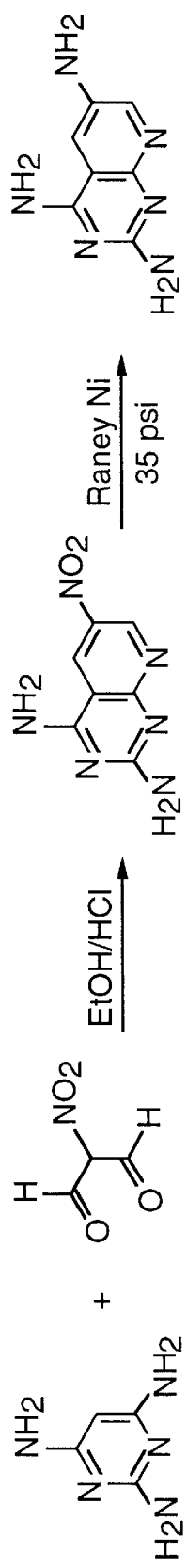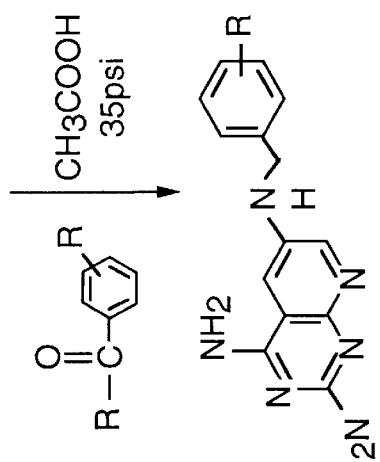
FIG. 15a
FIG. 15b
FIG. 15c

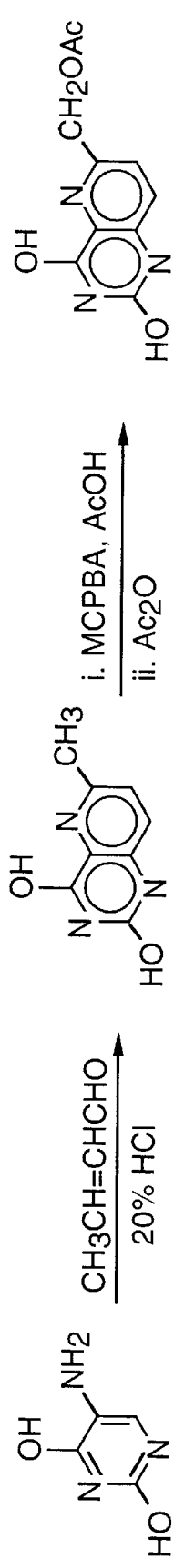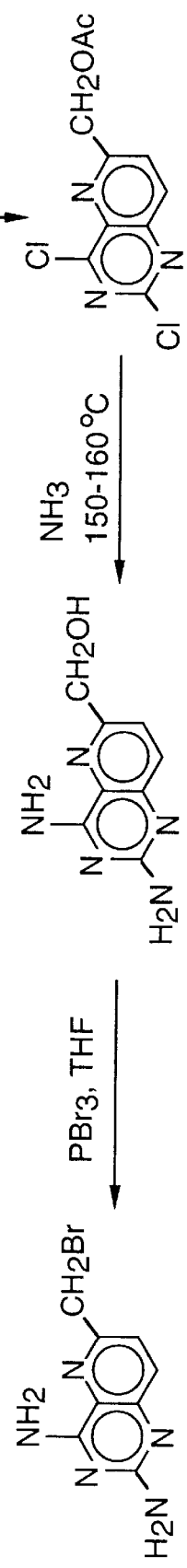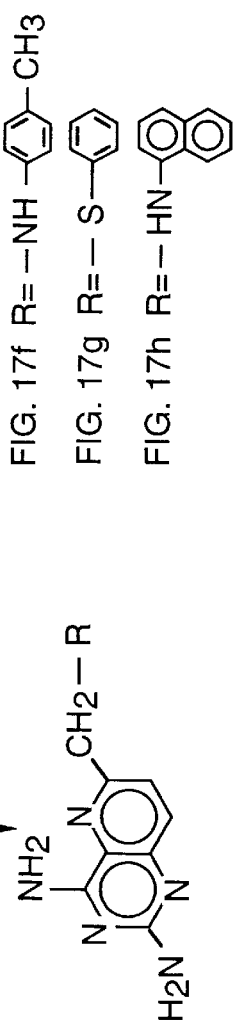
FIG. 17a
FIG. 17b
FIG. 17c
FIG. 17d
FIG. 17e
FIG. 17f R=—NH—C6H4—CH3
FIG. 17g R=—S—C6H5
FIG. 17h R=—HN—naphthyl

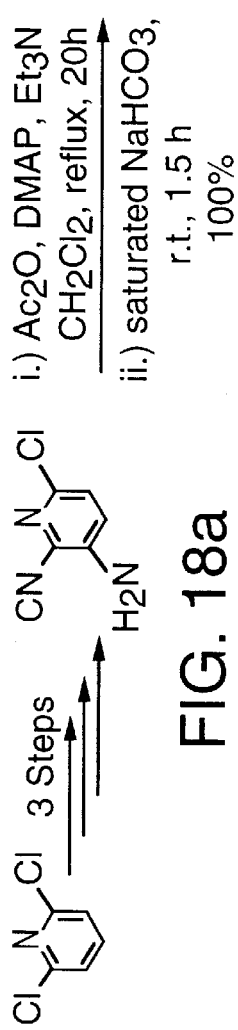
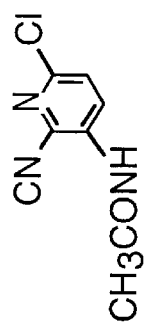
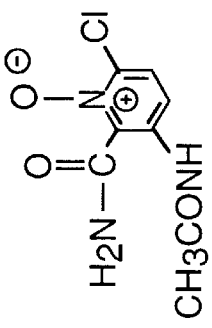
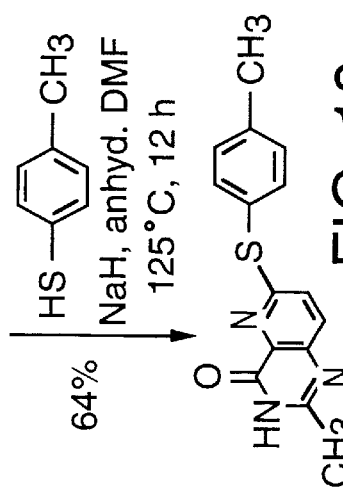
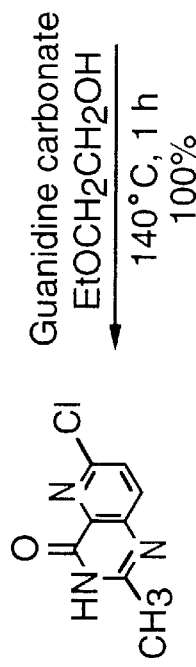
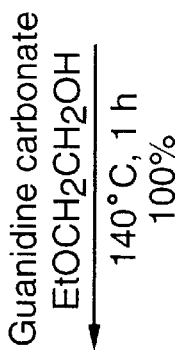
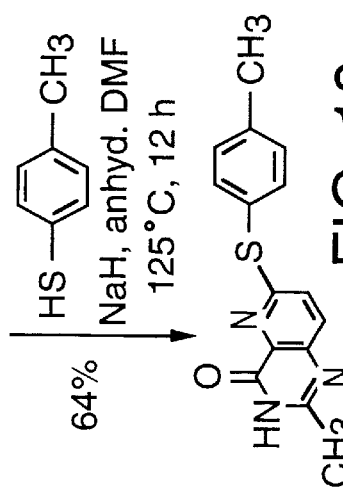
FIG. 18a  FIG. 18b  FIG. 18c  FIG. 18d  FIG. 18e

US 6,537,999 B2

PYRIMIDINE DERIVATIVES AND METHODS OF MAKING AND USING THESE DERIVATIVES

CROSS-REFERENCE TO RELATED APPLICATIONS

This application is a divisional of U.S. application Ser. No. 09/315,762, filed May 20, 1999, which is a Continuation-In-Part of 09/073,593, filed May 6, 1998, issued as U.S. Pat. No. 5,958,930 on Sep. 28, 1999, which is a continuation of Ser. No. 09/190,374, filed Nov. 12, 1998, issued as U.S. Pat. No. 6,096,750 on Aug. 1, 2000, which is a continuation of Ser. No. 08/660,023, filed Jun. 6, 1996, issued as U.S. Pat. No. 5,939,420 on Aug. 17, 1999.

This work was supported, in part, by grants from the National Institute of General Medical Sciences GM52811 (AG), and by the National Institute of Allergy and Infectious Disease AI 41743 (AG).

FIELD OF THE INVENTION

This invention relates to pyrimidine derivative compounds and pharmaceutically acceptable salts thereof. More specifically, this invention relates to furo[2,3-d]pyrimidines, pyrrolo[2,3-d]pyrimidines, pyrrolo[3,2-d]pyrimidines, pyrrolo[3,4-d]pyrimidines, thieno[2,3-d]pyrimidines, cyclopentapyrimidines, cyclopenta[d]pyrimidines, pyrido[2,3-d]pyrimidines and pyrido[3,2-d]pyrimidines. "Pyrimidine derivatives" as used herein generally refers to all of these types of compounds. These compounds have been found useful in resisting and treating *Pneumocystis carinii, Toxoplasmosis gondii, Mycobacterium tuberculosis* and *Mycobacterium avium* complex (MAC) infections in immunocompromised patients, such as, for example, patients with autoimmune deficiency syndrome (AIDS). These compounds are also useful as potential antitumor, antituberculosis, anti-*Mycobacterium avium*, antibiotic, antimalarial, antifungal or antiprotozoal agents, or as synergistic agents when used with sulfonamides or other compounds and may require the use of leucovorin rescue. These compounds are also useful as antitumor agents in cancer patients. Methods of preparing and using these compounds are also provided.

BACKGROUND OF THE INVENTION

Various pyrimidine systems, such as the pyrido[2,3-d] pyrimidine ring system, have been studied due to their involvement in the inhibition of dihydrofolate reductase (DHFR) enzymes activity. The pyrimidine derivatives disclosed herein function as DHFR inhibitors. Because DHFR reduces dihydrofolate to tetrahydrofolate, inhibition of DHFR deprives the cell of tetrahydrofolate, without which the cell cannot produce 5,10-methylenetetrahydrofolate. 5,10-Methylenetetrahydrofolate is essential for cell growth. The inhibition of DHFR by the compounds, and pharmaceutically acceptable salts thereof, of this invention therefore results in the inhibition of DNA synthesis and leads to cell death. Methotrexate (MTX), trimetrexate (TMQ), piritrexim (PTX) and other folic acid analogues function as inhibitors of cell growth by similar mechanisms involving the inhibition of dihydrofolate reductase.

The pyrimidine derivatives disclosed herein also function as thymidylate synthase (TS) inhibitors. TS, along with DHFR, forms part of the systems responsible for the synthesis of deoxythymidylate (dTMP) from deoxyuridylate (dUMP). TS catalyzes the sole de novo synthesis of dTMP from dUMP. Inhibition of TS, therefore, deprives the cell of thymidine, which is an essential constituent of DNA. Typically, the compounds as described herein where X and Y are both $NH_2$ or where X is $NH_2$ and Y is H or $CH_3$ and will function as DHFR inhibitors, and compounds where X is OH and Y is $NH_2$, H, or $CH_3$ will function as TS inhibitors, although the inventor does not wish to be bound by this generality.

Drugs useful for the reduction of cancerous cells are also known.

Elslager, Edward F., et al., "Folate Antagonists. 20. Synthesis and Antitumor and Antimalarial Properties of Trimetrexate and Related 6-[(Phenylamino)methyl]-2,4-quinazolinediamines" *J. Med. Chem.*, Vol. 26 pp. 1753–1760 (1983)), discloses the preparation of quinazolinediamines. This article states that the quinazolinediamines exhibit potent antimalarial, antibacterial and antitumor activity.

Methods of synthesizing diaminopyrido[2,3-d] pyrimidines having various substituents are known. See Hurlbert, B. S., et al., "Studies on Condensed Pyrimidine Systems. XXIII. Synthesis of 2,4-Diaminopyrido[2,3-d] pyrimidines from β-Keto Esters", *J. Med. Chem.*, Vol. 11, pp. 703–707 (1968), and Hurlbert, B. S., and Valenti, B. F., "Studies on Condensed Pyrimidine Systems. XXIV. The Condensation of 2,4,6-Triaminopyridimine with Malondialdehyde Derivatives", *J. Med. Chem.*, Vol. 11, pp. 708–710 (1968).

Hurlbert, B. S., et al., "Studies on Condensed Pyrimidine Systems. XXV. 2,4-Diaminopyrido[2,3-d]pyrimidines. Biological Data", *J. Med. Chem.*, Vol. 11, pp. 711–717 (1968), discloses the antimicrobial activities of several subgroups of pyridopyrimidines. This article states that 2,4-diaminopyrido[2,3-d]pyrimidines bearing alkyl and aralkyl substituents in the pyrimidine moiety are inhibitors of dihydrofolate reductase having antibacterial and antiprotozoal activity and that these compounds potentiate sulfonamides.

Grivsky, E. M., et al., "Synthesis and Antitumor Activity of 2,4-Diamino-6-(2,5-dimethoxybenzyl)-5-methylpyrido [2,3-d]pyridimine", *J. Med. Chem.*, Vol. 23, pp. 327–329 (1980), discloses the synthesis of 2,4-diamino-6-(2,5-dimethoxybenzyl)-5-methylpyrido[2,3-d]pyridimine (BW301U,7). This article states that BW301U,7 is as effective as methotrexate as an inhibitor of dihydrofolate reductase purified from human leukemic cells and, in contrast to metoprine, has minimal activity as an inhibitor of histamine metabolism.

Shih et al., "LY231514, a Pyrrolo[2,3-d]pyrimidine-based Antifolate That Inhibits Multiple Folate-requiring Enzymes", *Cancer Research*, Vol. 57, pp. 1116–1123 (1997) teaches a pyrrolo [2,3-d]pyrimidine-based antifolate that inhibits multiple folate-requiring enzymes. A classical or glutamic acid substituted pyrrolo pyrimidine is disclosed.

Taylor et al., "A Dideazatetrahydrofolate Analogue Lacking a Chiral Center at C-6, N-[4-[2-(2-Amino-3,4-dihydro4-oxo-7H-pyrrolo[2,3-d]pyrimidin-5-yl) ethyl]benzoyl]-L-glutamic Acid, Is an Inhibitor of Thymidylate Synthase", *J. Med. Chem.*, Vol. 35, pp. 4450–4454 (1992) also teaches a classic pyrrolo pyrimidine compound useful in the inhibition of thymidylate synthase. Taylor reports other pyrrolo pyrimidine compounds in U.S. Pat. Nos. 4,996,206; 5,028,608; 5,248,775; 5,254,687; and 5,344,932.

Werbel, Leslie, M., et al., "Synthesis and Antimalarial Activity of a Series of 2,4-Diamino-6-[(N-alkylanilino) methyl]quinazolines [1,2]", *J. Heterocyclic Chem.*, Vol. 24, pp. 345–349 (1987), discloses the synthesis of N6 substituted quinazoline dihydrofolate reductase inhibitors. This article states that these analogs demonstrate substantial activity against *Plasmodium berghei* infections in mice.

Piper, J. R., et al., "Syntheses and Antifolate Activity of 5-Methyl-5-deaza Analogues of Aminopterin, Methotrexate, Folic Acid, and $N^{10}$-Methylfolic Acid", *J. Med. Chem.*, Vol. 29, pp. 1080–1087 (1986), discloses that 5-methyl-5-deaza analogues of aminopterin and methotrexate are much more growth inhibitory than methotrexate.

Pyrido [2,3-d] and [3,2-d] pyrimidines are also disclosed in U.S. Pat. Nos. 5,346,900 and 5,508,281, and co-pending application Ser. Nos. 08/515,491 and 08/660,023 all of which are hereby expressly incorporated by reference.

Pyrrolo[2,3-d]pyrimidines are disclosed by Gangjee et al. in "Novel 2,4-diamino-5-substituted-pyrrolo[2,3-d] pyrimidines As Classical and Non-Classical Antifolate Inhibitors of Dihydrofolate Reductases", *J. Med. Chem.*, Vol. 38, pp. 2158–2165 (Jun. 6, 1995).

Gangjee, A., et al., "Classical and Non-Classical Furo[2, 3-d]Pyrimidines As Novel Antifolates: Synthesis and Biological Activities", *J. Med. Chem.*, Vol. 37, pp. 1169–1176 (1994), discloses furo[2,3-d]pyrimidines.

Mavandadi, et al., disclose 5-substituted classical and nonclassical 2,4-diaminopyrrolo[2,3-d]pyrimidines as antitoxoplasma, antipneuomocystis and antitumor agents in *J. Med. Chem.*, 40:1173–1177 (1997). Mavandadi, et al. also disclose use of pyrrolo[2,3-d]pyrimidines as nonclassical inhibitors of thymidylate synthase in *J. Med. Chem.*, 39:4563–4568 (1996).

There remains a very real and substantial need for compounds that are more active and more selective than known compounds at resisting and treating infections caused by *Pneumocystis carinii* and *Toxoplasmosis gondii*, and other organisms in immunocompromised patients, reducing the tumor size and/or the number of cancerous cells in cancer patients, and for methods of preparing and using such compounds.

SUMMARY OF THE INVENTION

The present invention has met the above described need by providing potent and selective pyrrolo[2,3-d]pyrimidine compounds and furo[2,3-d]pyrimidine compounds.

Methods of synthesizing the above compounds are also disclosed.

This invention provides methods for therapeutically and/or prophylactically using the compounds, and pharmaceutically acceptable salts and prodrugs thereof, described herein. More specifically, this invention provides methods of using the present pyrimidine derivatives for therapeutic and prophylactic purposes including employing these compounds to resist and treat secondary infections caused by *Pneumocystis carinii, Toxoplasmosis gondii, Mycobacterium tuberculosis* and *Mycobacterium avium* complex or other organisms in immunocompromised patients, such as for example patients with AIDS. The immunocompromised patient has a primary infection caused by a retrovirus, including for example, human immunodeficiency virus (HIV). In addition, this invention provides methods of using pyrimidine derivatives as antitumor, antituberculosis, anti-*Mycobacterium avium* complex, antibiotic, antimalarial, antifungal and antiprotozoal agents and as synergistic agents with sulfonamides in such patients.

This invention also provides methods of using pyrimidine derivatives for therapeutic and/or prophylactic purposes as antitumor agents or to otherwise destroy or minimize growth or proliferation of cancerous cells in cancer patients.

It is an object of this invention to provide pyrimidine derivative compounds, and pharmaceutically acceptable salts thereof, for substantially inhibiting dihydrofolate reductase enzymes.

It is an object of this invention to provide pyrimidine derivative compounds, and pharmaceutically acceptable salts thereof, for substantially inhibiting thymidylate synthase enzymes.

It is an object of the present invention to provide pyrimidine derivative compounds, and pharmaceutically acceptable salts thereof, having antitumor, antituberculosis, anti-*Mycobacterium avium* complex, antibiotic, antimalarial, antifungal or antiprotozoal activity including synergistic activity with sulfonamides and/or other agents.

It is a further object of this invention to provide pyrimidine derivative compounds, and pharmaceutically acceptable salts thereof, having effective activity against secondary infections, such as for example infections caused by *Pneumocystis carinii, Toxoplasmosis gondii, Mycobacterium tuberculosis* and *Mycobacterium avium* complex that occur in immunocompromised patients, such as patients with AIDS.

It is another object of this invention to provide pyrimidine derivative compounds, and pharmaceutically acceptable salts thereof, having effective activity against tumors and other cancerous cells, such as those caused by cancer.

It is an object of this invention to provide a method of synthesizing various pyrimidine derivative compounds, and pharmaceutically acceptable salts thereof.

It is a further object of this invention to provide methods of using in a patient a therapeutically effective amount of pyrimidine derivative compounds, or pharmaceutically acceptable salts thereof.

It is a further object of this invention to provide methods of using in a patient a prophylactically effective amount of pyrimidine derivative compounds, or pharmaceutically acceptable salts thereof.

These and other objects of the invention will be more fully understood from the drawing and the following description of the invention and the claims appended hereto.

BRIEF DESCRIPTION OF THE FIGURES

FIG. 2 shows compounds 1–9 as synthesized by the methods shown in FIG. 1.

FIG. 10 shows a schematic diagram of methods of preparing tricyclic[2,3-d]pyrimidines.

FIG. 12 shows a schematic diagram of the methods of preparing pyrido[3,2-d]pyrimidines.

FIG. 13 shows a schematic diagram of the methods of preparing pyrido[2,3-d]pyrimidines.

FIG. 14 shows a schematic diagram of the methods of preparing various 2,4-diaminopyrido[2,3-d]pyrimidines.

FIG. 15 shows a schematic diagram of the methods of preparing 2,4-diamino-6-substituted-benzylaminopyrido[2,3-d]pyrimidines.

FIG. 17 shows a schematic diagram of the methods of preparing pyrido[3,2-d]pyrimidines.

FIG. 18 shows a schematic diagram of the methods of preparing pyrido[3,2-d]pyrimidines.

DETAILED DESCRIPTION OF THE INVENTION

Figure 1:
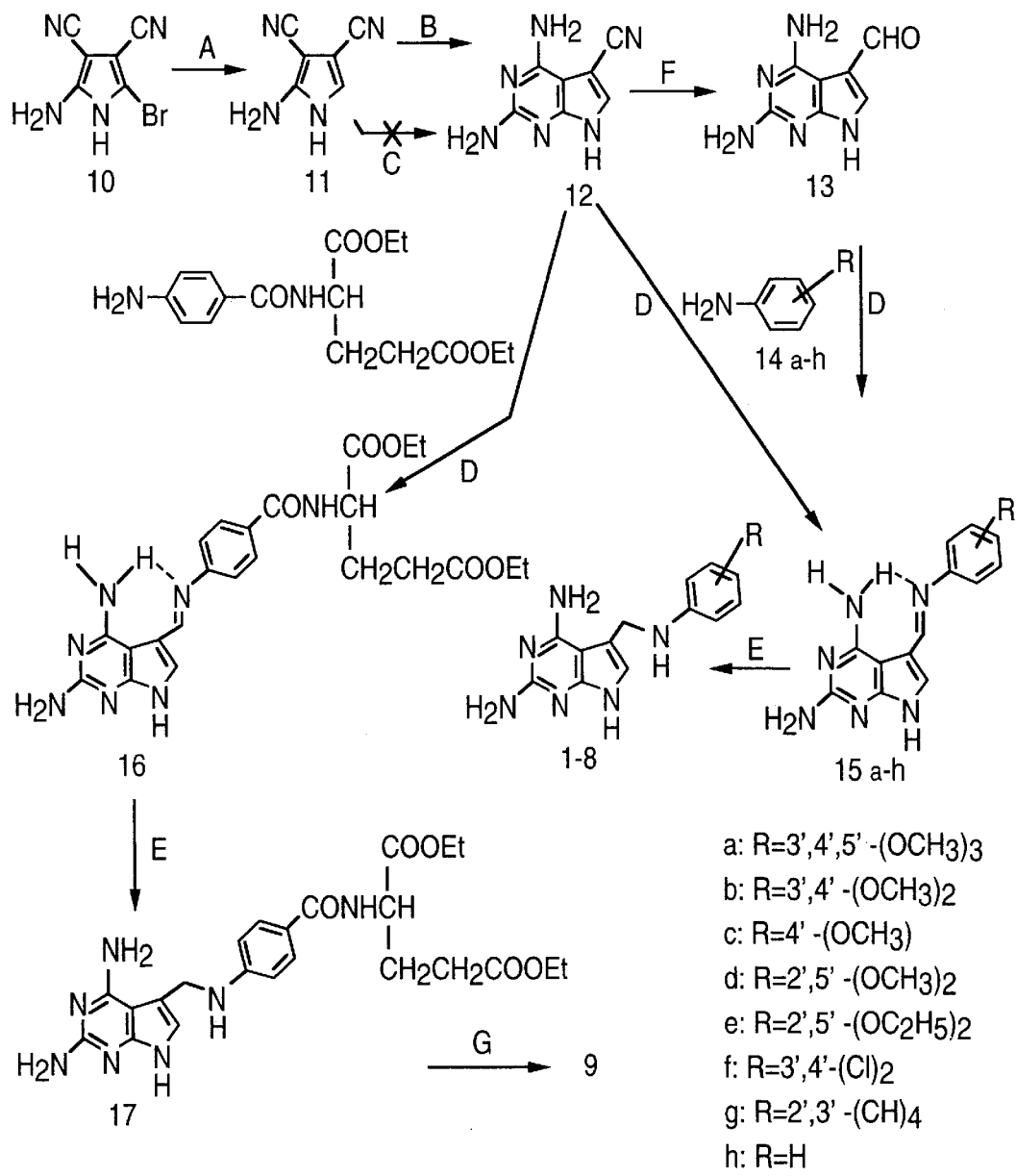
FIG. 1 shows a schematic diagram of methods of preparing 2,4-diamino-5-substituted-pyrrolo[2,3-d]pyrimidines.
Figure 3:
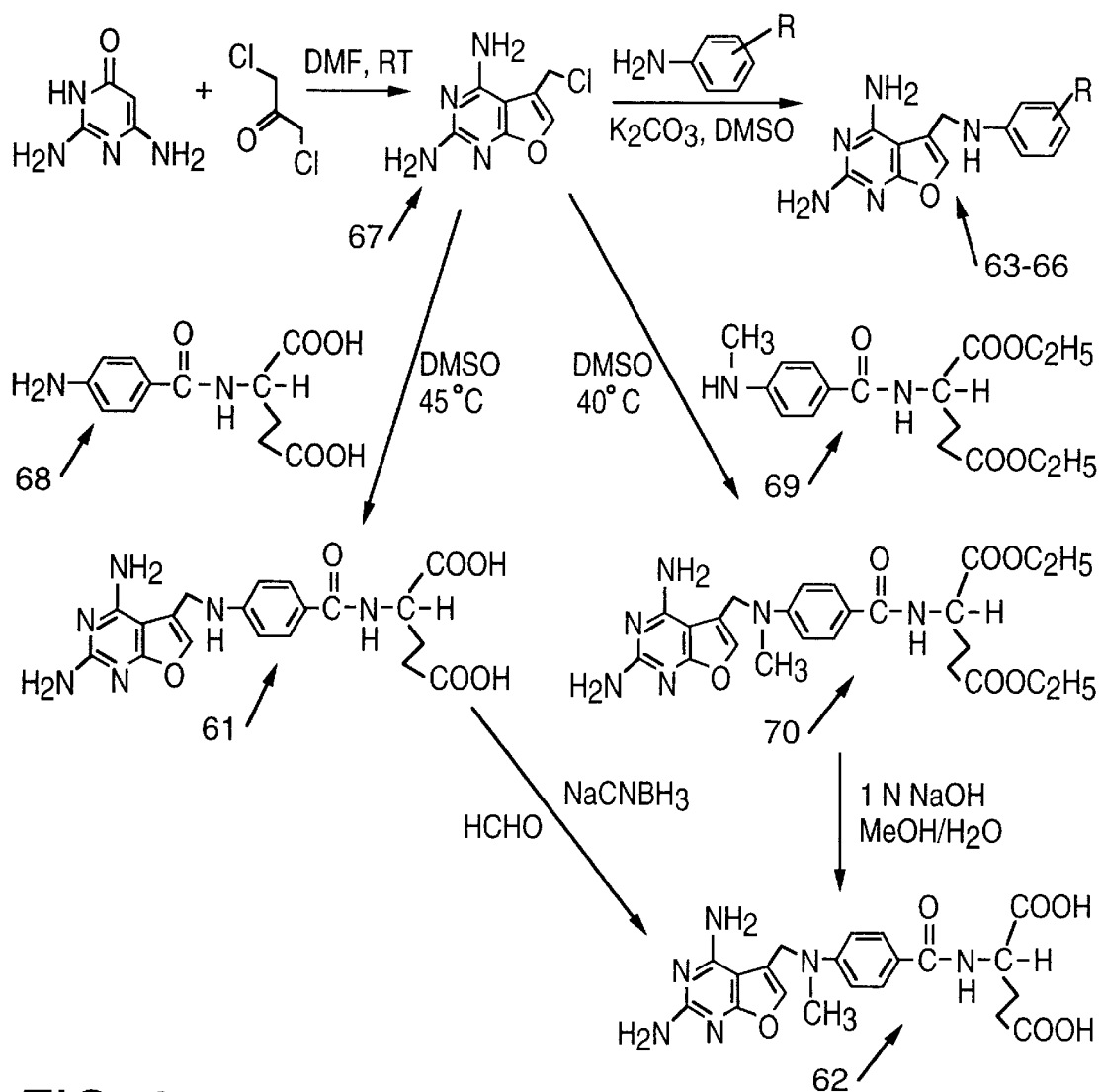
FIG. 3 shows a schematic diagram of the methods of preparing N-[4-[N-[2,4-diaminofuro[2,3-d]pyrimidin-5-yl]methyl]amino]benzoyl]-L-glutamic acid and the N-9 methyl analogue thereof.
Figure 4:
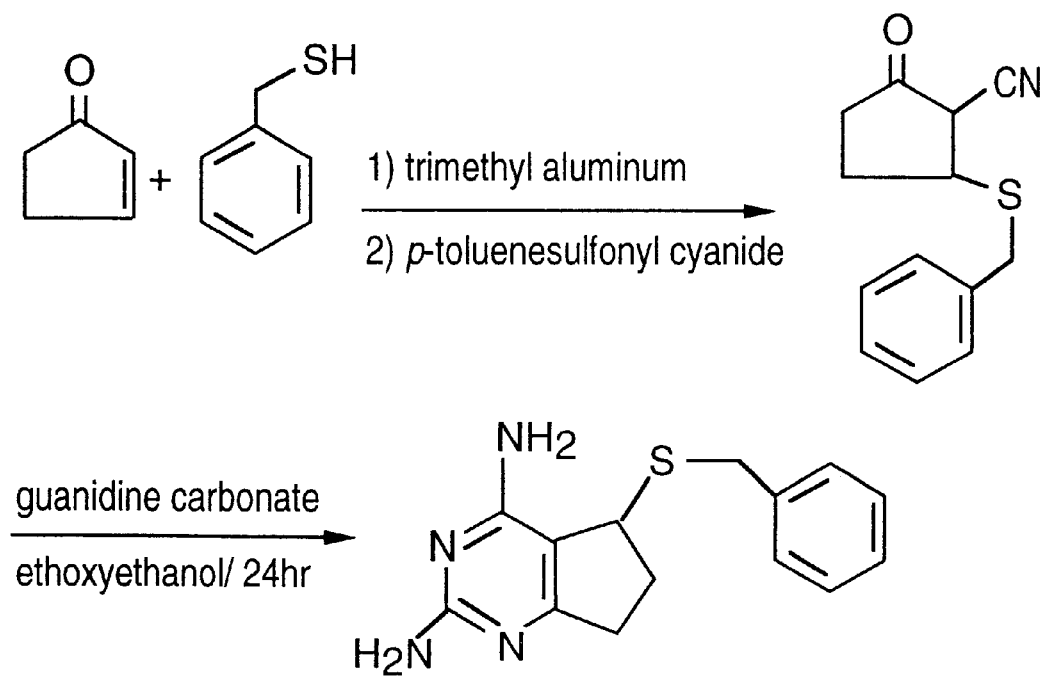
FIG. 4 shows a schematic diagram of the methods of preparing of a compound having formula 8.

As used herein, the term "patients" means members of the animal kingdom including but not limited to human beings.

The pyrimidine derivative compounds of the present invention, and pharmaceutically acceptable salts and prodrugs thereof, and methods of preparing and using these compounds provide for the therapeutic and prophylactic treatment of secondary infections caused by *Pneumocystis carinii, Toxoplasmosis gondii, Mycobacterium tuberculosis* and *Mycobacterium avium* complex in immunocompromised patients. Such patients could have a primary infection caused by a retrovirus including but not limited to human immunodeficiency virus (HIV). As will be appreciated by one skilled in the art, embodiments of the compounds, and pharmaceutically acceptable salts thereof, of the present invention which contain benzoyl-L-glutamate groups will not be applicable to these methods. That is because *Pneumocystis carinii* and *Toxoplasmosis gondii* are not generally known to take up enough of the benzoyl-L-glutamate forms of these compounds to be effective.

In addition, these compounds function as antitumor, anti-tuberculosis and anti-*Mycobacterium avium* complex, antibiotic, antifungal, antimalarial and antiprotozoal agents, and as synergistic agents with other compounds.

The compounds of this invention also provide for the therapeutic treatment of tumors, or other cancerous cells, in cancer patients. As used herein, the term "cancer" refers to any type of cancer including, but not limited to, leukemia, lung cancer, colon cancer, CNS cancer, melanoma, ovarian cancer, renal cancer, prostate cancer, and breast cancer. Prophylactic treatment of cancer is also contemplated by the present methods, in which the growth and/or spread of cancerous cells is minimized.

Many of the compounds disclosed in the present invention have mechanisms of action including but not limited to antifolates. The pyrrolo[2,3-d]pyrimidine compounds, furo[2,3-d]-pyrimidine compounds, pyrrolo[3,2-d] and pyrrolo[3,4-d]pyrimidine compounds, thieno[2,3-d]pyrimidine compounds, cyclopentapyrimidine compounds, cyclopenta-[d]pyrimidine compounds, pyrido[2,3-d]pyrimidine compounds, and pyrido[3,2-d]pyrimidine compounds, and pharmaceutically acceptable salts, formulations and prodrugs thereof, of this invention inhibit dihydrofolate reductase (DHFR) enzymes. The DHFR enzymes are needed for normal cell growth because they reduce dihydrofolate to tetrahydrofolate. Tetrahydrofolate is a precursor of 5,10-methylenetetrahydrofolate, which is essential for DNA replication and thus cell growth. The derivatives of the present invention inhibit dihydrofolate reductase and consequently inhibit DNA synthesis. Inhibition of DNA synthesis results in cell death.

In addition, the pyrimidine derivative compounds of the present invention, and pharmaceutically acceptable salts thereof, inhibit thymidylate synthase (TS). TS, along with DHFR, forms part of the system responsible for the synthesis of deoxythymidylate (dTMP) from deoxyuridylate (dUMP). Inhibition of TS deprives the cell of thymidine, which is an essential component of DNA.

As used herein, the term "pharmaceutically acceptable salts" include, salts of the present pyrimidine derivative compounds which are suitable for use in pharmaceutical applications. One skilled in the art would easily be able to determine whether a salt form of any given compound is suitable for use as a pharmaceutical. Examples of pharmaceutically acceptable salts include but are not limited to, acetate, formate, glucuronate, ethantate, sulfonate, or other salts known to those skilled in the art. "Pharmaceutically acceptable prodrugs" similarly refers to any prodrug formulations of the present compounds. A prodrug will be understood by those skilled in the art as a chemical compound that is converted into an active curative agent by processes within the body. Other formulations comprising the pyrimidine derivatives described herein are also within the scope of the present invention.

In the pyrimidine derivative formulas presented herein, when X and Y are either OH or $NH_2$, the enol form of the compounds is represented. The enol form is equivalent to and includes the keto form of the compounds.

As will be understood one skilled in the art, when any of the variables used herein equal zero, that variable is not present in a particular embodiment of the general formula. In any of the formulas described herein, when any of the "A" variables equals zero, the "R" variable attached thereto also equals zero, and the "B" variable is either zero or is attached directly to the carbon ring. When the "B" variable is zero, one or more of the "R" variables attached thereto can also be zero or are attached directly to the A variable. When both the A and B variables are zero, the R variables attached thereto can also be zero or are attached directly to the carbon ring. One skilled in the art will understand this based upon the particular formulas included herein and coupled with basic organic chemistry principles.

Some of the pyrrolo[2,3-d]pyrimidine compounds, and pharmaceutically acceptable salts thereof, of the present invention have the general formula (1):

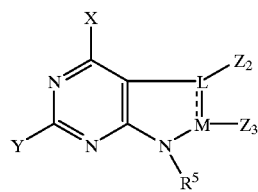

(1)

wherein X and Y are the same or different and are selected from the group consisting of OH, NH$_2$, H and CH$_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z$_2$ and Z$_3$ are different and are selected from the group consisting of R$_4$ and

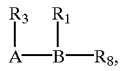

where Z$_2$ is R$_4$ when Z$_3$ is

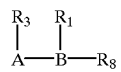

and Z$_2$ is

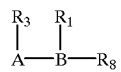

when Z is R$_4$;

wherein A is selected from the group consisting of CH and zero;

wherein B is selected from the group consisting of CH, nitrogen, N—CH$_2$, CH$_2$—N, CH$_2$—CH$_2$, oxygen, sulfur, sulfoxide, sulfone and zero;

wherein R$_1$ is selected from the group consisting of hydrogen, a lower alkyl group, a nitroso group, a formyl group and zero and R$_1$ is zero when B is zero, oxygen, sulfur, sulfoxide or sulfone;

wherein R$_3$ is selected from the group consisting of hydrogen, a lower alkyl group and zero, and R$_3$ is zero when A is zero;

wherein R$_4$ is selected from the group consisting of hydrogen and a lower alkyl group;

wherein R$_5$ is selected from the group consisting of hydrogen and a lower alkyl group;

wherein R$_8$ is selected from the group consisting of naphthyl, mono-, di- and tri-substituted naphthyl, thionaphthyl, thiophenyl and hydroxyphenyl when R$_1$ is hydrogen and R$_4$ is hydrogen;

wherein R$_8$ is selected from the group consisting of phenyl, mono-, di- and tri-substituted phenyl, naphthyl, mono-, di- and tri-substituted naphthyl, pyridine and p-aroyl-L-glutamate when R$_1$ is a lower alkyl group and R$_4$ is hydrogen;

wherein R$_8$ is selected from the group consisting of pyridine, phenyl, mono-, di- and tri-substituted phenyl, naphthyl, and mono-, di- and tri-substituted naphthyl and p-aroyl-L-glutamate when R$_1$ is zero;

wherein R$_8$ is selected from the group consisting of phenyl, mono-, di- and tri-substituted phenyl, naphthyl, mono-, di- and tri-substituted naphthyl and p-aroyl-L-glutamate when R$_1$ is hydrogen and R$_4$ is a lower alkyl group; and wherein R$_8$ is not p-benzoyl-L-glutamate or pyridine when X is OH, A is zero, B is sulfur, R$_4$ is methyl and R$_5$ is hydrogen, and R$_8$ is not p-benzoyl-L-glutamate when X is OH, A is CH, B is CH, R$_4$ is hydrogen and R$_5$ is hydrogen; and wherein each lower alkyl group is independently selected from the group consisting of lower alkyl groups having from 1 to 6 carbons.

Preferred embodiments of formula 1 are further recited in Table 1.

TABLE 1

| Compound | X | Y | L—M Bond | A | B | R$_1$ | R$_3$ | R$_4$ | R$_5$ | R$_8$ |
|---|---|---|---|---|---|---|---|---|---|---|
| 301 | NH$_2$ | NH$_2$ | dbl | CH | N | H | H | H | H | 1-naphthyl |
| 303 | NH$_2$ | NH$_2$ | dbl | CH | N | H | H | H | H | 4-OHphenyl |
| 304 | NH$_2$ | NH$_2$ | dbl | CH | N | CH$_3$ | H | H | H | 2,5-dimethoxy-phenyl |
| 305 | NH$_2$ | NH$_2$ | dbl | CH | N | CH$_3$ | H | H | H | 3,4-dichloro-phenyl |
| 306 | NH$_2$ | NH$_2$ | dbl | CH | N | CH$_3$ | H | H | H | 1-naphthyl |
| 307 | NH$_2$ | NH$_2$ | dbl | CH | S | —* | H | H | H | 3,4-dimethoxy-phenyl |
| 308 | NH$_2$ | NH$_2$ | dbl | CH | S | — | H | H | H | 3,4-dichloro-phenyl |
| 309 | NH$_2$ | NH$_2$ | dbl | CH | S | — | H | H | H | 1-naphthyl |
| 310 | NH$_2$ | NH$_2$ | dbl | CH | S | — | H | H | H | 2-naphthyl |
| 312 | NH$_2$ | NH$_2$ | dbl | CH | N | CH$_3$ | H | H | H | p-benzoyl-L glutamate |
| 313 | OH | NH$_2$ | dbl | CH | N | H | H | CH$_3$ | H | p-benzoyl-L glutamate |

TABLE 1-continued

| Compound | X | Y | L—M Bond | A | B | $R_1$ | $R_3$ | $R_4$ | $R_5$ | $R_8$ |
|---|---|---|---|---|---|---|---|---|---|---|
| 314 | OH | $NH_2$ | dbl | CH | N—$CH_2$ | H | H | $CH_3$ | H | p-benzoyl-L-glutamate |
| 315 | OH | $NH_2$ | dbl | CH | S | — | H | $CH_3$ | H | 4-pyridine |
| 317 | OH | $NH_2$ | dbl | — | S | — | — | $CH_3$ | H | 3,4-dimethoxyphenyl |
| 318 | OH | $NH_2$ | dbl | — | S | — | — | $CH_3$ | H | 3,4-dichlorophenyl |
| 319 | OH | $NH_2$ | dbl | — | S | — | — | $CH_3$ | H | 4-chlorophenyl |
| 320 | OH | $NH_2$ | dbl | — | S | — | — | $CH_3$ | H | 4-$NO_2$phenyl |
| 321 | OH | $NH_2$ | dbl | — | S | — | — | $CH_3$ | H | phenyl |
| 322 | OH | $NH_2$ | dbl | — | S | — | — | $CH_3$ | H | 2-naphthyl |

"—" indicates that the substituent is zero, that is, not present in the particular embodiment.

The most preferred embodiments of formula 1 are identified as compounds 312 and 320.

The present invention is further directed to methods of synthesizing 5-substituted pyrrolo[2,3-d]pyrimidines. Synthesis of these compounds according to the methods of the present invention can be accomplished by convergent synthesis. As will be understood by one skilled in the art, convergent synthesis involves the production of an intermediate product from which numerous additional compounds can be made. Here, the preferred intermediate product is 2,4-diamino-5-cyano pyrrolo-[2,3-d]pyrimidine.

More specifically, the present invention is directed to a method of synthesizing a compound, and pharmaceutically acceptable salts thereof, having the formula:

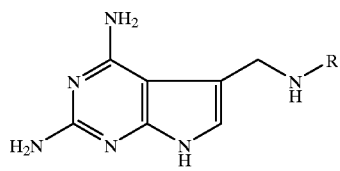

(2)

wherein R is selected from the group consisting of a lower alkyl group, a p-aroyl-L-glutamate group, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, a substituted alkoxyaryloxy group and a halogen; and wherein each lower alkyl group is independently selected from the group consisting of lower alkyl groups having from about 1 to 6 carbons, comprising the steps of:
a) debrominating a pyrrole;
b) fusing the product of step a) with an amidine;
c) condensing the product of step b) with a nucleophile;
d) reducing the product of step c); and
e) purifying the compounds of step d).

Preferably, the debromination of step a) is performed in a mixture of dimethylformamide (DMF) and methanol under hydrogenation in the presence of a palladium catalyst. Either a 5% Pd-$BaCO_3$ or a 10% Pd-C catalyst can be used; 5% Pd-$BaCO_3$ is preferred. Typically, the debromination step will be completed in about 3 hours, and the reaction performed under hydrogen at a pressure of between about 40 and 60 psi, preferably at about 50 psi.

The fusion of step b) is preferably performed with chloroformamidine hydrochloride, and more preferably performed by heating a uniformly stirred suspension of the product of step a) and chloroformamidine hydrochloride in a liquid heat transfer media and heating to a temperature of between about 150° C. and 180° C., preferably between about 160° C. and 170° C., for a period of between about 36 and 50 hours, preferably about 48 hours. Any liquid heat transfer media can be used, including Dowtherm-A®, available from Dow Chemical Company.

The selective nucleophile as disclosed in condensing step c) is selected from the group consisting of an aniline, diethyl(p-aminoaroyl)-L-glutamate, N-methyl and diethyl (p-aminoaroyl)-L-glutamate. Any suitable aniline can be used, including but not limited to an aniline of the formula

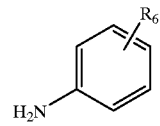

(3)

wherein $R_6$ is selected from the group consisting of 3',4',5'-trimethoxy, 3',4'-dimethoxy, 4'-methoxy, 2',5'-dimethoxy, 2',5'-diethoxy, 3',4'-dichloro, 2',3'-tetramethyl, hydrogen trimethoxy, dimethoxy and monomethoxy groups, trihalo, dihalo and monohalo groups, trialkyl, dialkyl and monoalkyl groups and combinations of methoxy groups, halo groups and lower alkyls.

Anilines of formula 3 are preferred for use in the methods of the present invention.

Preferably, the condensation of step c) is performed in 70% to 80% acetic acid under hydrogenation, and in the presence of a Raney nickel catalyst. Hydrogenation times of from about 24 to 72 hours, and hydrogenation pressures of between about 50 and 60 psi, preferably 55 psi, are preferred. Under these conditions, the Schiff bases are expected to form.

Alternatively, condensation can be accomplished by heating a mixture of the product of step b) with formaldehyde and Raney nickel at a temperature between about 70° and 90° C., preferably 80° C., for about 2 hours.

Reduction of the Schiff bases, step d), is preferably performed by stirring a solution of the product of step c) in methanol at room temperature using NaCNBH as the reducing agent. In addition, 50% methanolic hydrochloric acid or glacial acetic acid can be used to maintain the pH of the reaction mixture at about 2. The reduction step should take about 4 hours.

Preferably, the purification of step e) is performed by a method selected from the group consisting of silica gel column chromatography and dissolution of the product of step d) in methanol, filtration, evaporation of the filtrate, and trituration of the residue in anhydrous diethylether.

When either diethyl(p-aminoaroyl)-L-glutamate or N-methyl diethyl(p-aminoaroyl)-L-glutamate are used in the condensation of step c), an additional hydrolysis step, step f), is preferably performed following step e). Preferably, the hydrolysis of step f) is accomplished by stirring a solution of the product of step e) in a 1:1 sodium hydroxide:methanol solution at room temperature for between about 60 and 84 hours, preferably about 72 hours.

Specific embodiments of these methods are discussed in the examples below.

Preferred embodiments of the compounds produced by the methods of the present invention are further recited in Table 2.

TABLE 2

| Compound Number | R Group |
|---|---|
| 1 | 3,4,5-trimethoxyphenyl |
| 2 | 3,4-dimethoxyphenyl |
| 3 | 2,5-dimethoxyphenyl |
| 4 | 4-methoxyphenyl |
| 5 | 2,5-diethoxyphenyl |
| 6 | 3,4-dichlorophenyl |
| 7 | 2',3'-(CH)$_4$phenyl |
| 8 | phenyl |
| 9 | p-benzoyl-L-glutamate |

Compounds 4, 8 and 9, as defined in the above table, are preferred for therapeutically treating cancer patients, and compounds 4 and 8 for therapeutically and prophylactically treating infections caused by *Pneumocystis carinii* and *Toxoplasmosis gondii*.

The present invention also provides pyrrolo[2,3-d] pyrimidine compounds, and pharmaceutically acceptable salts thereof, having the formula (9):

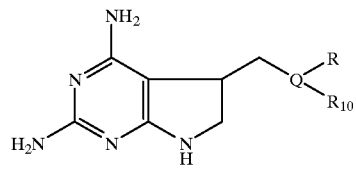

(9)

wherein Q is selected from the group consisting of nitrogen and sulfur;

wherein R is selected from the group consisting of a lower alkyl group, a p-aroyl-L-glutamate group, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, a substituted alkoxyaryloxy group and a halogen;

wherein $R_{10}$ is selected from the group consisting of hydrogen and a lower alkyl group; and wherein $R_{10}$ is a lower alkyl when Q is nitrogen.

Methods of synthesizing compounds having formula 9 as described above are also provided. These methods comprise the steps of:

a) debrominating a pyrrole;
b) fusing the product of step a) with an amide;
c) condensing the product of step b) with a nucleophile;
d) reducing the product of step c); and
e) purifying the compounds of step d); wherein the nucleophile of step c) is a compound having the general structure

wherein Q is selected from the group consisting of nitrogen and sulfur;

wherein R is selected from the group consisting of a lower alkyl group, a p-aroyl-L-glutamate group, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, a substituted alkoxyaryloxy group and a halogen;

wherein $R_{10}$ is selected from the group consisting of hydrogen and a lower alkyl group; and wherein $R_{10}$ is a lower alkyl when Q is nitrogen.

The present invention is also directed to furo[2,3-d] pyrimidine compounds, and pharmaceutically acceptable salts thereof, having the following general formula:

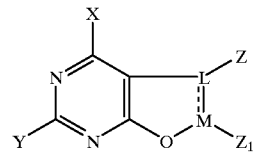

(4)

wherein X and Y are the same or different and are selected from the group consisting of OH, NH$_2$, H and CH$_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

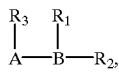

where Z is $R_4$ when $Z_1$ is

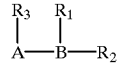

and Z is

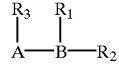

when $Z_1$ is $R_4$;

wherein A is selected from the group consisting of CH and zero;

wherein B is selected from the group consisting of sulfur, sulfoxide, sulfone, nitrogen, oxygen, CH, N—CH$_2$, CH$_2$—N, CH$_2$—CH$_2$, and zero;

wherein $R_1$ is selected from the group consisting of hydrogen, a lower alkyl group, a nitroso group, a formyl group and zero and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl, an alkoxy, an alkoxyaryloxy group, a halogen and zero but $R_2$ is not 3,4,5-trimethoxyphenyl, 3,4,5-trichlorophenyl, 3,4-dichlorophenyl, 2,5-dimethoxyphenyl or a p-benzoyl-L-glutamate when $R_1$ is hydrogen and $R_4$ is hydrogen, and $R_2$ is not p-benzoyl-L-glutamate when $R_1$ is methyl;

wherein $R_3$ is selected from the group consisting of hydrogen, a lower alkyl group, and zero and $R_3$ is zero when A is zero;

wherein $R_4$ is selected from the group consisting of hydrogen, a lower alkyl group, S—$R_7$ and

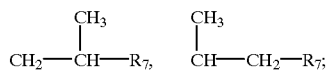

where $R_7$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl, an alkoxy, an alkoxyaryloxy group, a halogen and zero; and wherein each lower alkyl group is independently selected from the group consisting of lower alkyl groups having from 1 to 6 carbons.

In preferred embodiments of formula 4, X, Y, L, M and $R_4$ are as described above, A is CH, $R_3$ is H, B is S or N, $R_1$ is H or zero, and $R_2$ is selected from the group consisting of bicyclic and tricyclic ring systems. Preferably, $R_2$ is an unsubstituted or a mono, di or trisubstituted acridine, quinone, carbazole, phenanthrenes, dibenzofuran, anthracene, fluorene or fluorenone including but not limited to preferred embodiments wherein $R_2$ is selected from the group consisting of 1-anthracene, 2-anthracene, 1-fluorene, 2-fluorene, 2-(7-bromo)fluorene, 2-(9-hydroxy)fluorene, 1-fluoren-9-one, 2-fluoren-9-one, 3-fluoren-9-one, 4-fluoren-9-one, 2-(3-bromo)fluoren-9-one, 2-(7-bromo) fluoren-9-one, 2-fluoren-9-ol, 1-anthraquinone, 2-anthraquinone, 1-(9,10-dihydro)anthracene, 2-(9,10-dihydro)anthracene, 3-(9-ethyl)carbazole, and 2-(3-methoxy)dibenzofuran.

Particularly preferred embodiments of formula 4 are recited below in Table 3. For all of the embodiments described in Table 3, X is NH$_2$, Y is NH$_2$ and the bond between L and M is a double bond.

TABLE 3

| Compound | A | B | $R_1$ | $R_2$ | $R_3$ | $R_4$ |
|---|---|---|---|---|---|---|
| 159 | CH | S | — | phenyl | H | H |
| 160 | CH | S | — | 1-naphthyl | H | H |
| 161 | CH | S | — | 2-naphthyl | H | H |
| 162 | CH | N | H | 1-naphthyl | H | H |
| 163 | CH | N | H | 2-naphthyl | H | H |
| 164 | CH | O | — | 2-naphthyl | H | H |
| 165 | CH | N | H | 2-phenoxyphenyl | H | H |
| 166 | CH | N | H | 4-phenoxyphenyl | H | H |
| 167 | CH | N | H | 2-phenylphenol | H | H |
| 169 | CH | N | H | 2',5'-dichlorophenyl | H | H |
| 171 | CH | N | CH$_3$ | 3',4'-dichlorophenyl | H | H |
| 172 | CH | N | CH$_3$ | 3',4',5'-trichlorophenyl | H | H |
| 175 | CH | N | H | 3'-methoxyphenyl | H | H |
| 177 | CH | H | — | — | H | S—$R_7$* |
| 178 | CH | H | — | — | H | S—$R_7$† |
| 179 | — | — | — | phenyl | — | H |
| 420 | CH | S | — | phenyl | H | H |
| 421 | CH | S | — | 1-naphthyl | H | H |
| 422 | CH | S | — | 2-naphthyl | H | H |
| 423 | CH | N | H | 1-naphthyl | H | H |
| 424 | CH | N | H | 2-naphthyl | H | H |
| 425 | CH | O | — | 2-naphthyl | H | H |
| 426 | CH | N | H | 2-phenoxyphenyl | H | H |
| 427 | CH | N | H | 4-phenoxyphenyl | H | H |
| 428 | CH | N | H | 2-phenylphenyl | H | H |
| 429 | CH | N | CH$_3$ | 2-naphthyl | H | H |
| 430 | CH | N | H | 2,5-dichlorophenyl | H | H |
| 431 | CH | N | CH$_3$ | 3,4-dichlorophenyl | H | H |
| 432 | CH | N | CH$_3$ | 3,4,5-trichlorophenyl | H | H |
| 433 | CH | N | H | 3-methoxyphenyl | H | H |
| 434 | CH | N | CH$_3$ | 2,5-dimethoxyphenyl | H | H |
| 111-157B | CH | N | H | 1-anthracene | H | H |
| 111-178 | CH | N | H | 2-anthracene | H | H |
| 111-183 | CH | N | H | 1-fluorene | H | H |
| 111-184 | CH | N | H | 2-fluorene | H | H |
| 111-190 | CH | N | H | 2-methoxy(dibenzofuran) | H | H |
| 111-191 | CH | N | H | N-ethyl carbazole | H | H |
| 111-192 | CH | N | H | hydroxy fluorene | H | H |
| 111-194 | CH | N | H | 1-fluoren-5-one | H | H |
| 111-204 | CH | N | H | 1-fluoren-5-one | H | H |

*$R_7$ equals 1-naphthyl
†$R_7$ equals 2-naphthyl

Compounds 161 and 167, as well as compounds 422 and 428, as described in Table 3 are most preferred for therapeutically treating cancer patients, and therapeutically and prophylactically treating infections caused by *Pneumocystis carinii* and *Toxoplasmosis gondii*.

The present invention is also directed to methods for synthesizing the compound, and pharmaceutically acceptable salts thereof, having the formula (4)

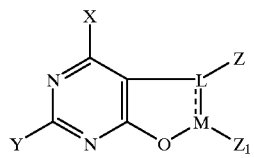

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

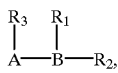

where Z is $R_4$ when $Z_1$ is

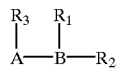

and Z is

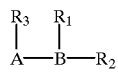

when $Z_1$ is $R_4$;

wherein A is selected from the group consisting of CH and zero;

wherein B is selected from the group consisting of sulfur, sulfoxide, sulfone, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, an alkoxyaryloxy group, a halogen and zero, but $R_2$ is not 3,4,5-trimethoxyphenyl, 3,4,5-trichlorophenyl, 3,4-dichlorophenyl, 2,5-dimethoxyphenyl or p-benzoyl-L-glutamate when $R_1$ is hydrogen and $R_4$ is hydrogen, and $R_2$ is not p-benzoyl-L-glutamate when $R_1$ is methyl;

wherein $R_3$ is selected from the group consisting of hydrogen, a lower alkyl group, and zero and $R_3$ is zero when A is zero;

wherein $R_4$ is selected from the group consisting of hydrogen, a lower alkyl group, S—$R_7$ and

where $R_7$ is selected from the group consisting of a lower alkyl group, p-aroyl-L-glutamate, an aryl group, an allylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl, an alkoxy, an alkoxyaryloxy group, a halogen and zero; and wherein each lower alkyl group is independently selected from the group consisting of lower alkyl groups having from 1 to 6 carbons, comprising the steps of:

a) stirring a pyrimidine and a substituted acetone in a solvent;
b) purifying the product of step a);
c) performing nucleophilic displacement of the chloride in the product of step b); and
d) purifying the product of step c).

In one embodiment of the methods described above, step a) is performed by stirring one equivalent each of 2,6-diamino-4-hydroxypyrimidine and 1,3-dichloroacetone in DMF at room temperature for a period of between about 12 and 36 hours, preferably 24 hours.

Purification of the product of step a) can be accomplished by any means known in the art; column chromatography is preferred. The product resulting from the purification step b) is not generally stable for long durations at room temperature. It is, therefore, preferred that the nucleophilic displacement of step c) be performed within about 1 hour of completion of step b).

The nucleophilic displacement of step c) can be accomplished by any of various compounds including those selected from the group consisting of p-aminoaroyl)-L-glutamic acid, diethyl N-p-methylaminoaroyl)glutamate, and a nucleophile. As used in reference to the methods for synthesizing a compound, and pharmaceutically acceptable salts thereof, having formula (4), nucleophile includes, but is not limited to aniline, substituted anilines, phenols, thiophenols and substituted phenols and thiophenols.

When step c) is performed with (p-aminoaroyl)-L-glutamic acid, the purification of step d) is preferably performed by precipitating the product of step c) by diluting said product with a suitable solvent, preferably water, and separating said product from unreacted starting materials and impurities by any means known in the art; cellulose column chromatography is preferred. Acidification of the product is then preferred.

When the nucleophilic displacement of step c) is performed with diethyl N-[p-methylamino(aroyl)]glutamate, the purification of step d) is preferably accomplished by stirring the product of step c) with 1N sodium hydroxide at room temperature for between about 12 to 36, preferably 24 hours, followed by acidification.

Alternatively, when conducting the nucleophilic displacement with p-aminoaroyl)-L-glutamic acid, the desired product can also be obtained by reductive methylation of the intermediate with a suitable aldehyde, preferably formaldehyde, and sodium cyanoborohydride at a pH of approximately 6 to 7. Purification is then accomplished by any means known in the art, preferably by wet cellulose column, and acidification of the product performed.

When the nucleophilic displacement reactions are accomplished with an aniline, the product of step b) is preferably mixed with anhydrous dimethylsulfoxide and two equivalents of potassium carbonate for approximately 60 to 84 hours, preferably 72 hours, at room temperature. Heating the reaction mixture to between about 35° and 45° C. for a period of between about 60 and 84 hours, preferably 72 hours, increases the yield of the desired product. The product is then isolated from impurities and other unreacted starting materials by any means known in the art. Preferably, isolation is accomplished by adding excess water to the reaction mixture and stirring at room temperature for a period of approximately 6 to 8 hours to separate the product; chromatographic purification is then performed.

The present invention is also directed to compounds, and pharmaceutically acceptable salts thereof, having the general formula

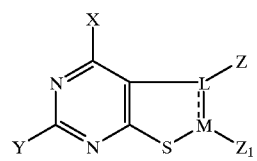

(5)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

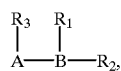

where $Z_1$ is $R_4$ when $Z_1$ is

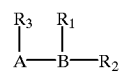

and Z is

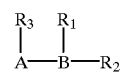

when $Z_1$ is $R_4$;

wherein A is selected from the group consisting of CH and zero;

wherein B is selected from the group consisting of sulfur, sulfoxide, sulfone, nitrogen, oxygen, CH, N—$CH_2$, $CH_2$—N, $CH_2$—$CH_2$, and zero;

wherein $R_1$ is selected from the group consisting of hydrogen, a lower allyl group, a nitroso group, a formyl group and zero and $R_1$ is zero when B is zero, oxygen, sulfur, sulfoxide or sulfone;

wherein $R_2$ is selected from the group consisting of a lower alkyl group, an aryl group, p-aroyl-L-glutamate, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and lower alkyl group; and wherein each lower alkyl group is independently selected from the group consisting of lower alkyl groups having from about 1 to 6 carbons.

The present invention is also directed to compounds, and pharmaceutically acceptable salts thereof, having the general formula:

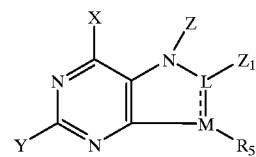

(6)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

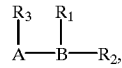

where Z is $R_4$ when $Z_1$ is

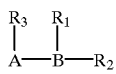

and Z is

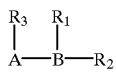

when $Z_1$ is $R_4$;

wherein A is selected from the group consisting of CH and zero;

wherein B is selected from the group consisting of sulfur, sulfoxide, sulfone, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero, and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and lower alkyl group;

wherein $R_5$ is selected from the group consisting of hydrogen and lower alkyl group; and wherein each lower alkyl group is independently selected from the group consisting of lower alkyl groups having from about 1 to 6 carbons.

In preferred embodiments of formula 6, Y and X are $NH_2$, the bond between L and M is a double bond, A is zero, B is CH, $R_1$ is hydrogen, $R_2$ is selected from the group consisting of phenyl and 3,4-dichlorophenyl, $R_3$ is zero, $R_4$ is selected from the group consisting of hydrogen and lower alkyl and $R_5$ is selected from the group consisting of hydrogen and lower alkyl.

The present invention is also directed to compounds, and pharmaceutically acceptable salts thereof, having the general formula:

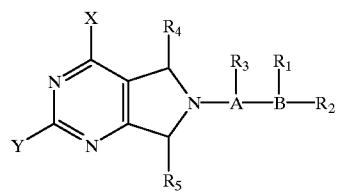

(7)

wherein X and Y are the same or different and are selected from the group consisting of OH, $NH_2$, H and $CH_3$;

wherein A is selected from the group consisting of CH and zero;

wherein B is selected from the group consisting of sulfur, sulfoxide, sulfone, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkoxy, an alkoxyaryloxy group, a halogen and zero;

wherein $R_3$ is selected from the group consisting of hydrogen, a lower alkyl group, and zero, and $R_3$ is zero when A is zero;

wherein $R_4$ is selected from the group consisting of hydrogen and lower alkyl group; and wherein each lower alkyl group is independently selected from the group consisting of lower alkyl groups having from about 1 to 6 carbons.

Figure 5:
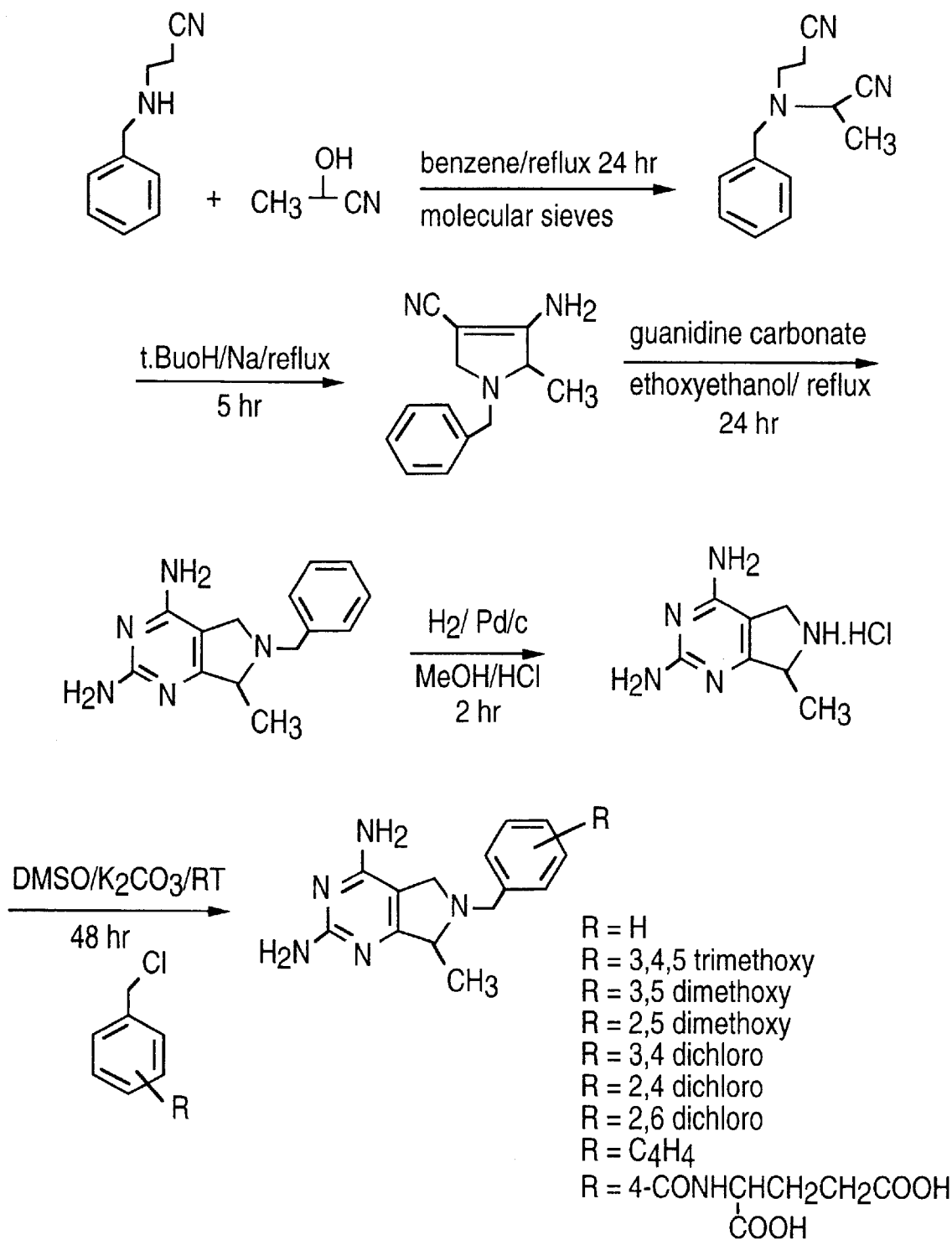
FIG. 5 shows a schematic diagram of the methods of preparing several compounds having formula 7.

In preferred embodiments of formula 7, X and Y are $NH_2$, A is zero, B is CH, $R_1$ is hydrogen, $R_2$ is selected from the group consisting of 3,4,5-trimethoxy-benzyl, 3,5-dimethoxybenzyl, 2,5-dimethoxybenzyl, 3,4-dichlorobenzyl, 2,6-dichloro-benzyl, 2,4-dichlorobenzyl, 2-$CH_2$-naphthyl, $C_4H_4$benzyl and 4-benzyl-L-glutamate, $R_3$ is zero, $R_4$ is hydrogen, and $R_5$ is selected from the group consisting of hydrogen and methyl. The most preferred embodiments of formula (7) are illustrated in FIG. 5.

The present invention is also directed to compounds, and pharmaceutically acceptable salts thereof, having the formula:

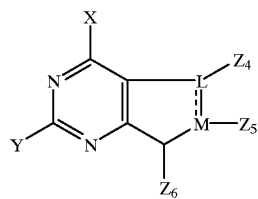

(8)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $Z_4$, $Z_5$ and $Z_6$ are different and are selected from the group consisting of $R_4$, $R_5$ and

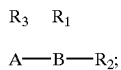

wherein A is selected from the group consisting of CH, sulfur and zero;

wherein B is selected from the group consisting of sulfur, sulfoxide, sulfone, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero, and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and a lower alkyl group;

wherein $R_5$ is selected from the group consisting of hydrogen and a lower alkyl group;

where $R_4$ is the same or different than $R_5$;

wherein each of said $R_4$, $R_5$ and

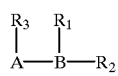

substituents is used once; and wherein each lower alkyl group is independently selected from the group consisting of lower alkyl groups having from about 1 to 6 carbons.

In a preferred embodiment of formula 8, X and Y are $NH_2$, the bond between L and M is single, A is sulfur, B is carbon, $R_1$ is hydrogen, $R_2$ is phenyl and $R_3$ is zero.

The present invention is also directed to tricyclic [3,2-d] and [2,3-d]pyrimidine compounds, and pharmaceutically acceptable salts thereof, having the general formula:

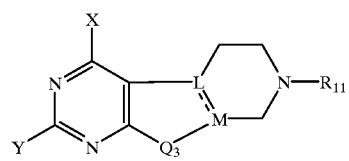

(10)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $R_{11}$ is selected from the group consisting of a lower alkyl group, an aryl group, p-aroyl-L-glutamate, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, an alkoxyaryloxy group, a halogen and zero; and $Q_3$ is selected from the group consisting of oxygen, NH, sulfur and $CH_2$.

In a preferred embodiment of formula 10, X and Y are $NH_2$, the bond between L and M is double, $Q_3$ is oxygen, and R is selected from the group consisting of phenyl, 3,4,5-trimethoxyphenyl, 3,5-dimethoxyphenyl, 2,4-dichlorophenyl, 3,4-dichlorophenyl, 2,6, dichlorophenyl and p-benzoyl-L-glutamate.

The present invention is also directed to a method for synthesizing the tricyclic pyrimidine compounds generally represented by formula (10). These methods generally include the steps of condensing a biselectrophile derived from a piperidine with a pyrimidine, preferably 2,4-diamino-6-hydroxy pyrimidine. Any compatible piperidine can be used; the piperidine chosen will depend on the final pyrimidine compound desired.

In a preferred method, the piperidine is 4-piperidine hydrochloride; protection of the piperidine is effected with ditertiary butyl-decarbonate in DMF at room temperature. Bromination of this protected piperidine is then performed in chloroform at room temperature to yield a mixed product containing a bromo-piperidine hydrobromide compound and an N-Boc brominated compound. These compounds are then condensed with a pyrimidine at room temperature for about 36 to 50 hours, preferably 48 hours. The resulting product is then reacted with the desired benzyl halide in anhydrous DMSO and anhydrous potassium carbonate for between about 48 and 72 hours at room temperature. Alternatively, the resulting product can be reacted with a benzoyl-L-glutamic acid diethyl ester instead of a benzyl halide.

The desired products of the above synthesis methods can be isolated using any purification means known in the art; chromatographic purification is preferred. The isolation of the products may be simplified by adding an excess of water to the reaction mixture and stirring at room temperature for between about 1 and 3 hours, which allows the products to separate.

The present invention is also directed to pyrido[2,3-d] and [3,2-d] pyrimidine compounds and pharmaceutically acceptable salts having the general formula:

(11)

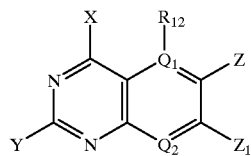

wherein X and Y may be the same or different and are selected from the group consisting of OH, $NH_2$, H and $CH_3$;

wherein Z and $Z_1$ are different and are selected from the group consisting of $R_4$ and

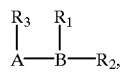

where Z is $R_4$ when $Z_1$ is

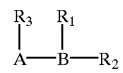

and Z is

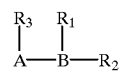

when $Z_1$ is $R_4$;

wherein $Q_1$ and $Q_2$ are the same or different and are selected from the group consisting of CH and nitrogen;

wherein A is selected from the group consisting of nitrogen, CH, sulfur and zero;

wherein B is selected from the group consisting of sulfur, sulfoxide, sulfone, CH, oxygen, nitrogen and zero, but B is not sulfur, sulfoxide, sulfone, oxygen or nitrogen when A is sulfur;

wherein $R_1$ is selected from the group consisting of hydrogen, a nitroso group, an aldehyde, a lower alkyl group, a formyl group and zero, and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an aklyltriaryl group, a substituted diaryl group and a substituted triaryl group, and each substituent of the substituted aryl group, diaryl group, and triaryl group is the same or different and is selected from the group consisting of a lower alkyl group, an alkoxy, a substituted alkoxyaryloxy group, a halogen and zero;

wherein $R_3$ is selected from the group consisting of H, a lower alkyl and zero, and $R_3$ is zero when A is zero;

wherein $R_{12}$ is selected from the group consisting of hydrogen and methyl;

but $R_2$ is not 2,5-dimethoxyphenyl when X is $NH_2$, Y is $NH_2$, $Q_1$ is CH, $Q_2$ is N, $Z_1$ is H, B is CH, $R_1$ is H and $R_{12}$ is methyl; and wherein each lower alkyl group is independently selected from the group consisting of lower alkyl groups having from about 1 to 6 carbons.

In one embodiment of formula 11, X and Y are both $NH_2$, $Q_1$ is nitrogen, $Q_2$ is CH, $Z_1$ is hydrogen, A is zero, B is nitrogen, $R_1$ is hydrogen, $R_2$ is selected from the group consisting of phenyl, 2-methoxyphenyl, 4-methoxyphenyl, 4-chlorophenyl, 3,4-dimethoxyphenyl, 2,5-dimethoxyphenyl, 3,4,5-trimethoxyphenyl and 3,4-$C_4H_4$phenyl, $R_3$ is zero and $R_{12}$ is hydrogen.

In another embodiment of formula 11, X and Y are both $NH_2$, $Q_1$ is nitrogen, $Q_2$ is CH, $Z_1$ is hydrogen, A is zero, B is sulfur, $R_1$ is zero, $R_2$ is selected from the group consisting of 2-methoxyphenyl, 4-methoxyphenyl and 3,4-dimethoxyphenyl, $R_3$ is zero and $R_{12}$ is hydrogen.

In another embodiment of formula 11, X and Y are both $NH_2$, $Q_1$ is nitrogen, $Q_2$ is CH, $Z_1$ is hydrogen, A is zero, B is nitrogen, $R_1$ is methyl, $R_2$ is selected from the group consisting of 3,4,5-trimethoxyphenyl, 2,5-dimethoxyphenyl, 3,4-dimethoxyphenyl, 3,4,5-trimethoxyphenyl, phenyl, 3,4-$C_4H_4$phenyl and 2,3-$C_4H_4$phenyl, $R_3$ is zero and $R_{12}$ is hydrogen.

In another embodiment of formula 11, X and Y are both $NH_2$, $Q_1$ is nitrogen, $Q_2$ is CH, $Z_1$ is hydrogen, A is zero, B is sulfone, $R_1$ is zero, $R_2$ is selected from the group consisting of 2-methoxyphenyl, 4-methoxyphenyl, and 3,4-dimethoxy-phenyl, $R_3$ is zero and $R_{12}$ is hydrogen.

The present invention is also directed to pyrido[2,3-d] and [3,2-d] pyrimidine compounds and pharmaceutically acceptable salts having the general formula:

(12)

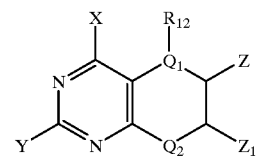

wherein X and Y may be the same or different and are selected from the group consisting of OH, $NH_2$, H and $CH_3$;

wherein Z and $Z_1$ are different and are selected from the group consisting of $R_4$ and

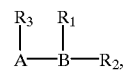

where Z is $R_4$ when $Z_1$ is

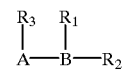

and Z is

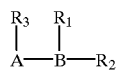

when $Z_1$ is $R_4$;

wherein $Q_1$ and $Q_2$ are the same or different and are selected from the group consisting of CH and nitrogen;

wherein A is selected from the group consisting of nitrogen, CH, sulfur and zero;

wherein B is selected from the group consisting of sulfur, sulfoxide, sulfone, CH, oxygen, nitrogen and zero, but B is not sulfur, sulfoxide, sulfone, oxygen or nitrogen when A is sulfur;

wherein $R_1$ is selected from the group consisting of hydrogen, a nitroso group, an aldehyde, a lower alkyl group, a formyl group and zero, and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an aklyltriaryl group, a substituted diaryl group and a substituted triaryl group, and each substituent of the substituted aryl group, diaryl group, and triaryl group is the same or different and is selected from the group consisting of a lower alkyl group, an alkoxy, a substituted alkoxyaryloxy group, a halogen and zero;

wherein $R_3$ is selected from the group consisting of H, a lower alkyl and zero, and $R_3$ is zero when A is zero;

wherein $R_{12}$ is selected from the group consisting of hydrogen and methyl; and wherein each lower alkyl group is independently selected from the group consisting of lower alkyl groups having from about 1 to 6 carbons.

The present invention is also directed to 5-substituted 2,4-diaminopyrrolo[2,3-d]pyrimidines and 2-amino-4-oxo-pyrrolo[2,3-d]pyrimidines, and pharmaceutically acceptable salts thereof, having the general formula:

(13)

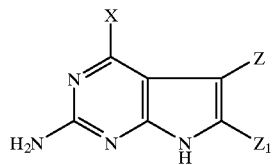

wherein X is selected from the group consisting of OH and $NH_2$;

wherein Z and $Z_1$ are different and are selected from the group consisting of $R_4$ and

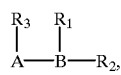

where Z is $R_4$ when $Z_1$ is

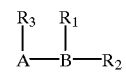

and Z is

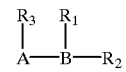

group when $Z_1$ is $R_4$;

wherein A is selected from the group consisting of CH, sulfur, nitrogen and zero;

wherein B is selected from the group consisting of CH, NH, N—$CH_2$, $CH_2$—N, $CH_2$—$CH_2$, O, S, sulfoxide, sulfone and zero, but B is not sulfur, sulfoxide, sulfone, oxygen or nitrogen when A is sulfur;

wherein $R_1$ is selected from the group consisting of H, a lower alkyl group, a nitroso group, a formyl group and zero, and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkoxy, alkoxyaryloxy group, halogen and zero;

wherein $R_3$ is selected from the group consisting of hydrogen, a lower alkyl group and zero, and $R_3$ is zero when A is zero;

wherein $R_4$ is selected from the group consisting of hydrogen, and a lower alkyl group; and wherein each lower alkyl group is independently selected from the group consisting of lower alkyl groups having from about 1–6 to carbons.

Preferred embodiments of formula 13 are represented in the following table:

TABLE 4

| Cmpd. | X | A | B | $R_1$ | $R_2$ | $R_3$ | $R_4$ |
|---|---|---|---|---|---|---|---|
| 402 | $NH_2$ | CH | CH | H | p-benzoyl-L-glutamate | H | H |
| 403 | $NH_2$ | CH | N | H | p-benzoyl-L-glutamate | H | H |
| 404 | OH | CH | CH | H | p-benzoyl-L-glutamate | H | H |
| 405 | OH | CH | N | H | p-benzoyl-L-glutamate or substituted aryl rings | H | H |
| 406 | OH | — | S | — | p-benzoyl-L-glutamate | — | $CH_3$ |
| 408 | OH | CH | N | H | 2,5-dimethoxyphenyl | H | H |
| 409 | OH | CH | N | H | 3,5-dimethoxyphenyl | H | H |
| 410 | OH | CH | N | H | 2,4-dimethoxyphenyl | H | H |
| 411 | OH | CH | N | H | 3,4,5-trimethoxyphenyl | H | H |
| 412 | OH | CH | N | H | 2,5-dichlorophenyl | H | H |
| 413 | OH | CH | N | H | 3,5-dichlorophenyl | H | H |
| 414 | OH | CH | N | H | 2,4-dichlorophenyl | H | H |
| 415 | OH | CH | N | H | 3-chlorophenyl | H | H |

Particularly preferred embodiments are represented by compounds 402 and 405. The substituted aryl rings of compound 405 can be any substituted aryl ring, including but not limited to an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkoxy, alkoxyaryloxy group, halogen and zero. Suitable substituents include but are not limited to substituted and unsubstituted acridine, anthracenes, fluorenes, fluorenones, carbazoles, dibenzofuran and phenanthrenes.

Compounds represented generally by formula 13, particularly those described above, and more particularly compound 404, have shown excellent antitumor activity. It has been observed that a 2,4-diamino substituted pyrimidine ring can contribute to potent DHFR inhibitory activity. Compounds 402 and 403 have particularly strong DHFR inhibitory potency. An unexpected result of the present invention, is the potent inhibitory activity of Compound 404 against both DHFR and TS.

Other pyrrolo[2,3-d]pyrimidines, and pharmaceutically acceptable salts, formulations, and prodrugs thereof, encompassed by the present invention have the general formula:

(14)

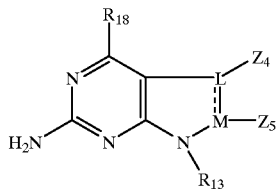

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $Z_4$ and $Z_5$ are different and are selected from the group consisting of $R_{14}$ and

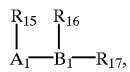

where $Z_4$ is $R_{14}$ when $Z_5$ is

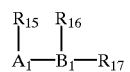

and $Z_4$ is

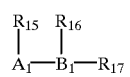

when $Z_5$ is $R_{14}$;
wherein $A_1$ is CH;
wherein $B_1$ is CH;

wherein $R_{13}$ is selected from the group consisting of H, a lower alkyl group, a substituted or unsubstituted aralkyl group, and a substituted or unsubstituted aryl group;

wherein $R_{14}$ is selected from the group consisting of H and a lower alkyl group;

wherein $R_{15}$ is selected from the group consisting of H and a lower alkyl group;

wherein $R_{16}$ is selected from the group consisting of H and a lower alkyl group;

wherein $R_{17}$ is selected from the group consisting of aryl, diaryl, triaryl, mono-, di- or tri-substituted aryl, mono-, di- or tri-substituted diaryl, mono-, di- or tri-substituted triaryl, substituted or unsubstituted heteroaryl, and p-aroyl-L-glutamate and each of said substituents is independently selected from the group consisting of a substituted or unsubstituted lower alkyl group, a substituted or unsubstituted alkoxy, a substituted or unsubstituted alkoxyaryloxy group and a halogen;

wherein $R_{18}$ is a lower alkyl group; and wherein each lower alkyl group is independently selected from the group consisting of lower alkyl groups having from about 1 to 6 carbons.

Several preferred embodiments of formula 14 are illustrated in Table 5 below. For all of these compounds, L and M are carbon and the bond between L and M is double, $Z_5=R_{14}=H$, $R_{15}$ is H, $R_{16}$ is H, and $R_{18}$ is methyl.

TABLE 5

PREFERRED EMBODIMENTS OF FORMULA 14

| Compound | $R_{13}$ | $R_{17}$ |
|---|---|---|
| 113–102 | benzyl | phenyl |
| 113–103 | H | phenyl |
| 113–118 | benzyl | 4-methoxy phenyl |
| 113–125 | H | 4-methoxy phenyl |
| 113–143 | benzyl | 3-methoxy phenyl |
| 113–143B | H | 3-methoxy phenyl |
| 113–148 | benzyl | 2-methoxy phenyl |
| 113–154B | H | 2-methoxy phenyl |
| 113–149 | benzyl | 3,4,5-trimethoxy phenyl |
| 113–154A | H | 3,4,5-trimethoxy phenyl |
| 113–151 | benzyl | p-benzoyl-L-glutamate |
| 113–161 | H | p-benzoyl-L-glutamate |

Particularly preferred embodiments are represented by compounds 113–143, 113–149 and 113–154B.

The present invention is further directed to furo[2,3-d]pyrimidine compounds, and pharmaceutically acceptable salts and prodrugs thereof, having the general formula:

(15)

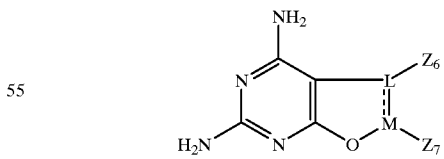

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $Z_6$ and $Z_7$ are different and are selected from the group consisting of $R_{14}$ and

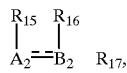

where $Z_6$ is $R_{14}$ when $Z_7$ is

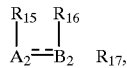

and $Z_6$ is

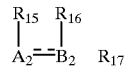

when $Z_5$ is $R_{14}$;
wherein $A_2$ is selected from the group consisting of carbon and CH;
wherein $B_2$ is selected from the group consisting of carbon and CH;
wherein the chemical bond between $A_2$ and $B_2$ is selected from the group consisting of a single bond and a double bond, $A_2$ and $B_2$ are carbon when the bond is a double bond and $A_2$ and $B_2$ are CH when the bond is a single bond;
wherein $R_{14}$ is selected from the group consisting of H and a lower alkyl group;
wherein $R_{15}$ is selected from the group consisting of H and a lower alkyl group;
wherein $R_{16}$ is selected from the group consisting of H and a lower alkyl group;
wherein $R_{17}$ is selected from the group consisting of aryl, diaryl, triaryl, mono-, di- or tri-substituted aryl, mono-, di- or tri-substituted diaryl, mono-, di- or tri-substituted triaryl, substituted or unsubstituted heteroaryl, and p-aroyl-L-glutamate and each of said substituents is independently selected from the group consisting of a substituted or unsubstituted lower alkyl group, an alkoxy, a substituted or unsubstituted alkoxyaryloxy group and a halogen; and
wherein each lower alkyl group is independently selected from the group consisting of lower alkyl groups having from about 1 to 6 carbons.

Preferred embodiments of formula 15 are illustrated in Table 6 below. For all of these compounds, $Z_7=R_{14}=H$, $R_{15}$ is H, and $R_{16}$ is methyl.

TABLE 6

PREFERRED EMBODIMENTS OF FORMULA 15

| COMPOUND | L | M | $A_2$ | $B_2$ | $R_{17}$ |
|---|---|---|---|---|---|
| 120-74 | carbon | carbon | CH | CH | p-benzoyl-L-glutamate |
| 120-88 | carbon | carbon | carbon | carbon | p-benzoyl-L-glutamate* |
| 120-82 | carbon | carbon | carbon | carbon | p-benzoyl-L-glutamate** |
| 120-44 | carbon | carbon | CH | CH | phenyl |
| 120-35 | carbon | carbon | CH | CH | 3,4,5-trimethoxy phenyl |
| 120-54 | carbon | carbon | CH | CH | 3,4-dimethoxy phenyl |
| 120-76 | carbon | carbon | CH | CH | 3-methoxy phenyl |
| 120-70-2 | carbon | carbon | CH | CH | 2-methoxy phenyl |
| 120-58 | carbon | carbon | CH | CH | 3,4-dichloro phenyl |
| 120-61 | carbon | carbon | CH | CH | 2,3,4-trichloro phenyl |
| 120-67 | carbon | carbon | CH | CH | 2,5-dichloro phenyl |
| 120-69 | carbon | carbon | CH | CH | 2,4-dichloro phenyl |
| 120-49 | carbon | carbon | CH | CH | 6-methoxy naphthyl |
| 120-92 | carbon | carbon | CH | CH | naphthyl |
| 120-101 | carbon | carbon | CH | CH | fluorene |
| 120-103 | carbon | carbon | CH | CH | biphenyl |
| 120-103-2 | CH | CH | CH | CH | biphenyl |
| 120-105 | carbon | carbon | CH | CH | 2,5-dimethoxy phenyl |
| 120-106 | carbon | carbon | CH | CH | 2-chlorophenyl |
| 120-106-2 | CH | CH | CH | CH | 2-chlorophenyl |
| 120-107 | carbon | carbon | CH | CH | 4-chlorophenyl |
| 120-38 | carbon | carbon | carbon | carbon | phenyl### |
| 120-25 | carbon | carbon | carbon | carbon | 3,4,5-trimethoxy phenyl### |
| 120-50 | carbon | carbon | carbon | carbon | 3,4-dimethoxy phenyl### |
| 120-71 | carbon | carbon | carbon | carbon | 3-methoxy phenyl### |
| 120-70-1 | carbon | carbon | carbon | carbon | 2-methoxy phenyl* |
| 120-56 | carbon | carbon | carbon | carbon | 3,4-dichloro phenyl# |
| 120-57-2 | carbon | carbon | carbon | carbon | 2,3,4-trichloro phenyl |
| 120-57 | carbon | carbon | carbon | carbon | 2,3,4-trichloro phenyl## |
| 120-37-1 | carbon | carbon | carbon | carbon | 2,5-dichloro phenyl* |
| 120-37-2 | carbon | carbon | carbon | carbon | 2,5-dichloro phenyl*** |
| 120-66 | carbon | carbon | carbon | carbon | 2,4-dichloro phenyl* |
| 120-46 | carbon | carbon | carbon | carbon | 6-methoxy naphthyl### |
| 120-91 | carbon | carbon | carbon | carbon | naphthyl### |
| 120-20 | carbon | carbon | carbon | carbon | naphthyl* |
| 120-48 | carbon | carbon | carbon | carbon | biphenyl |
| 120-40-1 | carbon | carbon | carbon | carbon | 2,5-dimethoxy phenyl |
| 120-64 | carbon | carbon | carbon | carbon | 2-chloro phenyl* |
| 120-60 | carbon | carbon | carbon | carbon | 3-chloro phenyl* |
| 120-65 | carbon | carbon | carbon | carbon | 4-chloro phenyl## |
| 120-94 | carbon | carbon | carbon | carbon | 4-carbethoxy phenyl |
| 120-96 | carbon | carbon | CH | CH | 4-carbethoxy phenyl |

*= E isomer
**= Z:E ratio = 1:1
***= Z isomer
= E:Z ratio = 3:2
= E:Z ratio = 4:1
= E:Z ratio = 2:1

As used herein, the term "lower alkyl group" refers to an alkyl group having between 1 and 6 carbons and can include straight, branched or cyclic alkyl chains. The number of carbons in each lower alkyl group in each of the present pyrimidine derivative formulas can vary. For example, in any given formula, $R_1$ could represent a lower alkyl group having 1 carbon, $R_2$ could represent a lower alkyl group having 2 carbons, $R_3$ could represent a lower alkyl group having 3 carbons, and $R_4$ could represent a lower allyl group having 4 carbons.

Thus, for all of the formulas described above, the lower alkyl groups are the same or different and are independently selected from straight chain, branched chain or cyclic (alicyclic hydrocarbon) arrangements having one to about six carbon atoms and can be substituted or unsubstituted, such as methyl, ethyl, propyl, i-propyl, butyl, i-butyl, t-butyl, pentyl, hexyl, cyclopropyl, cyclobutyl, cyclohexyl, cyclopropylmethyl or cyclobutylmethyl groups. The carbon atoms of these straight chain, branched chain or cyclic arranged lower alkyl groups may have one or more substituents for the hydrogens attached to the carbon atoms. Such substituents are described below. It will be understood that when the lower alkyl group contains one or more substituents three may be more than six carbons in the lower alkyl group, but the main carbon chain will typically have six or less carbons.

"Aryl" groups will be understood as referring to compounds whose molecules have a ring structure, such as the six carbon ring of benzene or multiple rings which are either fused or unfused, such as condensed six carbon rings of other aromatic derivatives. Suitable aryl groups therefore include for example phenyl, biphenyl, benzyl, naphthyl, phenanthrene and anthracene groups. Thus, the term "aryl" includes diaryl and triaryl groups which would have two and three rings, respectively, which are further described below. The aryl groups can be substituted or unsubstituted with any number of substituents including but not limited to a lower alkyl group, a substituted or unsubstituted alkoxy, a substituted or unsubstituted alkoxyaryloxy group and a halogen. Suitable substituted aryl groups include for example: mono-, di- and tri-substituted alkoxy phenyl groups; mono-, di- and tri-halogenated phenyl groups; mono-, di- and tri-substituted alkyl phenyl groups; mono-, di- and tri-substituted alkoxy benzyl groups and mono-, di- and tri-substituted halogenated benzyl groups. Similarly substituted diaryl and triaryl groups are also suitable. Also included within the term "aryl" are heterocycles, heteroaromatics or heteroaryls, which terms are used interchangeably herein and which will be understood to those skilled in the art as closed ring structures having at least one atom in the ring which is not carbon, such as oxygen, nitrogen or sulfur. Examples include but are not limited to pyrimidines, indoles, thiophenes, furans, benzofurans, pyridines, pyrroles, purines, and the like. "Heteroaryls" as used herein also refers to such ring structures that are part of larger ring structures, such as two or three member ring systems, which may be fused or unfused, in which one of the rings is as described above. It will be understood that this list is not meant to be exhaustive, and that any aryl group, as that term is commonly understood in the art, is within the scope of the present invention.

The terms "alkylaryl", "aryl alkyl" and "aralkyl" refer to groups having an alkyl moiety attached to an aryl ring such as a phenyl or benzyl ring. The alkyl moiety is preferably a lower alkyl chain having one to about seven carbon atoms. This alkyl moiety may also contain oxygen, nitrogen or sulfur atoms, such as for example methoxy groups. The aryl moiety of the alkylaryl group is an unsubstituted, mono-substituted, di-substituted or tri-substituted aryl group, as that term is described above.

As used herein, the term aroyl, such as for example when used within the term p-aroyl-L-glutamate, refers to heteroaroyl, benzoyl, napthoyl, thiophenoyl, furophenoyl, pyrroyl, and any other "aroyl" as that term would be understood by one skilled in the art. "Aroyl" is generally defined in the art as an aromatic or heteroaromatic compound having a carbonyl moiety.

The "R" groups described in the above formulas can generally be substituted or unsubstituted. Each substituent on each group is independently selected from the group consisting of a substituted or unsubstituted lower alkyl group having one to about six carbon atoms, a substituted or unsubstituted alkoxy group, for example methoxy, a substituted or unsubstituted aryl, diaryl or triaryl group, a substituted or unsubstituted heteroaryl, a substituted or unsubstituted alkoxyaryloxy group and a halogen, for example fluorene, chlorine or bromine.

Examples of other "R" substituent groups included in the formulas described above can include but are not limited to those wherein: the alkylaryl group is selected from the group consisting of an alkylphenyl and alkylbenzyl group; the alkyldiaryl group is selected from the group consisting of alkylnaphthyl, alkylbenzothiophene, alkylindene, alkylbenzofuran, alkylindole and alkylaminoquinoline; the alkyltriaryl group is an alkylanthracyl group; the substituted aryl, diaryl and triaryl group is selected from the group consisting of a mono-, di- and tri-substituted alkylphenyl and alkylbenzyl group, alkylnaphthyl, alkylbenzothiophene, alkylindole, alkylbenzofuran, alkylindene, alkylaminoquinoline, alkylanthracyl; each substituted alkyldiaryl and alkyltriaryl group is selected from the group consisting of a mono-, di- and tri-substituted alkylnaphthyl, alkylbenzothiophene, alkylindole, alkylbenzofuran, alkylindene, alkylaminoquinoline and alkylanthracyl group; and each substituent is the same or different and is selected from the group consisting of methyl, ethyl, n-propyl, i-propyl, n-butyl, i-butyl, t-butyl, branched n-pentyl, branched pentyl, n-hexyl, branched hexyl, cyclopropyl, cyclobutyl, cyclopentyl, cyclohexyl, cyclopropylmethyl, cyclobutylmethyl, methoxy group, chlorine atom, bromine atom and fluorene atom.

Examples of substituted or unsubstituted diaryl or triaryl (bicyclic or tricyclic) ring systems suitable for use in the present invention include but are not limited to acridine; anthracenes including but not limited to 1-anthracene, 2-anthracene, 1-(9,10-dihydro)anthracene, 2-(9,10-dihydro) anthracene; quinones including but not limited to 1-anthraquinone, 2-anthraquinone, fluorenes including but not limited to 1-fluorene, 2-fluorene, 2-(7-bromo)fluorene, 2-(9-hydroxy)fluorene, 1-fluoren-9-one; fluorenones including but not limited to 2-fluoren-9-one, 3-fluoren-9-one, 4-fluoren-9-one, 2-(3-bromo)fluoren-9-one, 2-(7-bromo) fluoren-9-one, 2-fluoren-9-ol; carbazoles including but not limited to 3-(9-ethyl)carbazole; dibenzofuran including but not limited to 2-(3-methoxy)dibenzofuran; and phenanthrenes. These ring systems can themselves contain any number of the additional "R" group substituents discussed above. For example, a diaryl ring system (two fused aryl rings) could itself have one or more aryl substituents, as could a triaryl ring system (three fused aryl rings). The tricyclic rings systems are preferred; their configuration increases the attraction between the compound and the enzyme and helps in the binding of the compound and enzyme.

In some embodiments of this invention, the compounds, and pharmaceutically acceptable salts thereof, having one of the formulas described above wherein X and Y are each $NH_2$, $R_1$ is selected from the group consisting of H, $CH_3$ and CHO, $CH_3$CHO, and zero and R, $R_2$, and $R_{17}$ are selected from the group consisting of 2,5-dimethoxyphenyl, 2,3,4- trimethoxyphenyl, 2,4,6-trimethoxyphenyl, naphthyl, 4-methoxynaphthyl, anthracyl and methoxy anthracyl, fluorene, benzothiophene, indene, benzofuran, indole, aminoquinoline, 2,3-dichlorophenyl, 2,4-dichlorophenyl, 2,5-dichlorophenyl, 2,6-dichlorophenyl, 3,4-dichlorophenyl and 3,5-dichlorophenyl. $R_3$ is $CH_3$ or hydrogen, $R_4$ is either hydrogen, methyl, ethyl, propyl and butyl group, cyclopropyl, cyclobutyl and cyclohexyl or zero, B is selected from the group consisting of nitrogen, carbon, sulfur and oxygen, A is selected from the group consisting of nitrogen, carbon and sulfur.

In other embodiments of this invention, compounds and pharmaceutically acceptable salts thereof, are provided having any of the above formulas wherein X and Y are each $NH_2$. $R_1$ is selected from the group consisting of H, $CH_3$, NO and CHO, $CH_3$CHO, zero. R, $R_2$ and $R_{17}$ are selected from the group consisting of 2-methoxyphenyl, 3-methoxyphenyl, 4-methoxyphenyl, 2,4-dimethoxyphenyl, 3,4-dimethoxyphenyl, 3-5-dimethoxyphenyl, 2-chlorophenyl, 3-chlorophenyl, 4-chlorophenyl, 2,3,4-trichlorophenyl, 2,4,5-trichlorophenyl, 2,4,6-trichlorophenyl, 3,4,5-trichlorophenyl, 2-bromophenyl, 3-bromophenyl, 4-bromophenyl, 2,4-dibromophenyl, 2,5-dibromophenyl, 2,6-dibromophenyl, 3,4-dibromophenyl, 3,5-dibromophenyl, 2,4,6-tribromophenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,4,5-trifluorophenyl, 2,4,6-trifluorophenyl, 2-methylphenyl, 3-methylphenyl, 4-methylphenyl, 2,3-dimethylphenyl, 2,4-dimethylphenyl, 2,5-dimethylphenyl, 2,6dimethylphenyl, 3,4-dimethylphenyl, 3,5-dimethylphenyl, 2,4,5-trimethylphenyl, and 2,4,6-trimethylphenyl. $R_3$ is $CH_3$ or hydrogen, and in formulas 3–5. $R_4$ is selected from the group consisting of hydrogen, methyl, ethyl, propyl, and butyl group, cyclopropyl, cyclobutyl, cyclohexyl and zero. B is selected from the group consisting of nitrogen, carbon, sulfur and oxygen and A is selected from the group consisting of nitrogen, carbon and sulfur.

In other embodiments of this invention, compounds and pharmaceutically acceptable salts thereof, are provided having any of the above formulas wherein X and Y are each $NH_2$. $R_1$ is selected from the group consisting of H, $CH_3$, NO and CHO, $CH_3$CHO, zero. R, $R_2$ and $R_{17}$ are selected from the group consisting of methyl, ethyl, n-propyl, n-butyl, cyclopropyl, cyclobutyl, cyclopentyl, cyclohexyl, 2-methoxybenzyl, 3,4-dimethoxybenzyl, 2,3-dimethoxybenzyl, 3,4-dimethoxybenzyl, 2,3,4-trimethoxybenzyl, 3,4,5-trimethoxybenzyl, 2-chlorobenzyl, 3,4-dichlorobenzyl, 2,3-dichlorobenzyl, 2,4-dichlorobenzyl, 2,5-dichlorobenzyl, 2,6-dichlorobenzyl, 2,6-dichlorobenzyl, 3,4-dichlorobenzyl, 3,5-dichlorobenzyl, 2-bromobenzyl, 3,4-dibromobenzyl, 2-fluorobenzyl, 3,4-difluorobenzyl, 2,4-difluorobenzyl, 2,5-difluorobenzyl, 2,6-difluorobenzyl and 3,4-difluorobenzyl. $R_3$ is $CH_3$ and hydrogen, and in formulas 3-5 $R_4$ is selected from the group consisting of a hydrogen, methyl, ethyl, propyl, butyl group, cyclopropyl, cyclobutyl, cyclohexyl; B is selected from the group consisting of nitrogen, carbon, sulfur and oxygen; and A is selected from the group consisting of nitrogen, carbon and sulfur.

The present invention further relates to methods of using the above-described compounds, and pharmaceutically acceptable salts thereof, in therapeutically an/or prophylactically treating a patient with an illness. As used herein, the term "illness" refers to cancer, infection by *Pneumocystis carinii*, infection by *Toxoplasmosis gondii*, *Mycobacterium tuberculosis* and *Mycobacterium avium* complex, or other secondary infections arising in immunocompromised patients, such as those with AIDS, and infections caused by bacteria, tuberculosis, malaria, fungi or protozoa.

A method of therapeutically treating a patient for an illness comprises the steps of:
  a) employing a compound, or pharmaceutically acceptable salts thereof, having any of the above formulas 1, 2 or 4–15;
  b) incorporating said compound in a suitable pharmaceutical carrier; and
  c) administering a therapeutically effective amount of said compound incorporated in said carrier to a patient.

As used herein, the term "suitable pharmaceutical carrier" refers to any pharmaceutical carrier known in the art, absent compatibility problems with the compounds of formula 1, 2 or 4–15. Preferred carriers include physiologic saline and 5% dextrose.

As used herein, the term "therapeutically effective amount" refers to that amount of any of said compounds of formulas 1, 2 or 4–15 incorporated in a suitable pharmaceutical carrier which is required to bring about a desired effect, such as reducing tumor size, destroying cancerous cells or resisting/treating infection caused by organisms such as *Pneumocystis carinii, Toxoplasmosis gondii, Mycobacterium tuberculosis* and *Mycobacterium avium* complex.

As will be understood by one skilled in the art, a therapeutically effective amount of said compound can be administered by any means known in the art, including but not limited to, injection, parenterally, orally, or, where appropriate, topically.

It is well within the skill of one practicing in the art to determine what dosage, and the frequency of this dosage, which will constitute a therapeutically effective amount for each individual patient, depending on the type of illness and the severity of such illness. It is also within the skill of one practicing in the art to select the most appropriate method of administering the compounds based upon the needs of each patient.

Methods of prophylactically treating a patient for an illness comprise the steps of:
  a) employing a compound, or pharmaceutically acceptable salts thereof, having any of the formulas 1, 2 or 4–15 as described above;
  b) incorporating said compound in a suitable pharmaceutical carrier; and
  c) administering a prophylactically effective amount of said compound incorporated in said carrier to a patient; wherein said illness is selected from the group consisting of infection caused by *Pneumocystis carinii, Toxoplasmosis gondii, Mycobacterium tuberculosis* and *Mycobacterium avium* complex.

As used herein, the term "prophylactically effective amount" refers to that amount of any of the compounds described above which will cause the body to generate antibodies in amounts sufficient to resist the onset of infection caused by *Pneumocystis carinii, Toxoplasmosis gondii, Mycobacterium tuberculosis* or *Mycobacterium avium* complex in immunocompromised patients.

As will be understood by one skilled in the art, a prophylactically effective amount of said compound can be administered by any means known in the art, including but not limited to, injection, parenterally, orally, or, where appropriate, topically.

It is well within the skill of one practicing in the art, to determine what dosage, and the frequency of this dosage, which will constitute a prophylactically effective amount for each individual patient, depending on the type of illness, such as the type of cancer, and the severity of such illness. It is also within the skill of one practicing in the art to select the most appropriate method of administering the compounds based upon the needs of each patient.

EXAMPLES

The following examples are set forth to illustrate various embodiments of the invention, and should not be construed as limiting the invention in any way. Standard test procedures familiar to those skilled in the art were used in the examples, such as those procedures described by Gangjee, A., et al., in "5-Arylthio-substituted 2-amino-4-oxo-6-methyl pyrrolo]2,3-d]pyrimidine antifolates as thymidylate synthase inhibitors and antitumor agents", *J. Med. Chem.*, Vol. 38, pp. 4495–4502 (1995); "Effect of bridge region variation on antifolate and antitumor activity of classical 5-substituted 2,4-diamino furo [2,3-d]pyrimidines", *J. Med. Chem.*, Vol. 38, pp. 3798–3805 (1995); and "Novel 2,4-diamino-5-substituted-pyrrolo[2,3-d]pyrimidines As Classical and Non-Classical Antifolate Inhibitors of Dihydrofolate Reductases", *J. Med. Chem.*, Vol. 38, pp. 2158–2165 (Jun. 6, 1995) and references disclosed therein.

Example 1

Compounds 1–6, 8, 301 and 303–312 were evaluated as inhibitors of dihydrofolate reductase (DHFR) from *Pneumocystis carinii* (Pc), *Toxoplasmosis gondii* (Tg) and rat liver (RL). Performance of these compounds was compared with that of trimetrexate (TMQ), piritrexim (PTX), trimethoprim (TMP) and methotroxate (MTX), all of which are currently available. Trimetrexate is available from Warner-Lambert/Parke Davis Pharmaceutical Research, Ann Arbor, Mich. Trimetrexate is approved by the United States Food and Drug Administration as an approved new drug for the treatment of *Pneumocystis carinii* infections in patients with AIDS. PTX is an experimental anticancer agent in Phase II clinical trials and is also an agent against *Pneumocystis carinii* and *Toxoplasmosis gondii*. TMP is an agent used against *Pneumocystis carinii* infection in conjunction with sulfonamides. MTX is a clinical used anticancer agent.

The evaluations of Compounds 1–6, 8, 301 and 303–312 consisted of determining the $IC_{50}$ values and selectivity ratios of each compound against Pc DHFR, Tg DHFR and RL DHFR. The $IC_{50}$ value is the concentration of a compound required to inhibit the dihydrofolate reductase activity by 50 percent (%). It will be understood by those skilled in the art that the lower the $IC_{50}$ value the more potent the compound. The selectivity ratio is a measure of the selectivity of a compound for Pc DHFR or Tg DHFR and is expressed as the $IC_{50}$ value of the DHFR from rate liver (RL) divided by the $IC_{50}$ value of either the Pc DHFR or the Tg DHFR, depending on which organism the compounds are being tested against. For example, the selectivity ratio of a compound is calculated by the following formula:

$$\frac{IC_{50}\ RL\ DHFR}{IC_{50}\ (Pc\ DHFR\ or\ Tg\ DHFR)}$$

It will be understood by those skilled in the art that the higher the selectivity ratio, the less toxic the compound is to mammalian dihydrofolate reductase, and thus, less toxic to the patient.

Table 7 sets forth the $IC_{50}$ values for Pc DHFR, RL DHFR and Tg DHFR and the corresponding selectivity ratios for the compounds tested.

TABLE 7

Inhibitory Concentrations ($IC_{50}$,μM) and Selectivity Ratios

| Compound # | Pc DHFR[1] | RL DHFR[1] | Selectivity Ratio: RL DHFR/ Pc DHFR | Tg DHFR[1] | Selectivity Ratio: RL DHFR/ Tg |
|---|---|---|---|---|---|
| 1 | >23 | 56.3 | <2.4 | 8.1 | 7.0 |
| 2 | 119.0 | 116.0 | 1.0 | 4.3 | 27.0 |
| 3 | 279.0 | 63.0 | 0.23 | 6.0 | 10.5 |
| 4 | 45.7 | 156.0 | 3.4 | 1.7 | 92.0 |
| 5 | >21 | 70.0 | <3.3 | 5.3 | 13.2 |
| 6 | 35.3 | 14.4 | 0.4 | 1.4 | 10.3 |
| 8 | 252.0 | >252 | >1 | 3.9 | >65 |
| 9 | 0.038 | 0.044 | 1.20 | 0.21 | 0.21 |
| 301 | 307.0 | 59.3 | 0.2 | 1.1 | 53.9 |
| 303 | 81.0 | 4.2 | 0.05 | 1.4 | 3.0 |
| 304 | >12.0 | >12.0 | ND* | 3.4 | >4.0 |
| 305 | 28.90 | 3.0 | 0.11 | 1.0 | 3.0 |
| 306 | 209.0 | 8.20 | 0.04 | 0.87 | 9.43 |
| 307 | 11.10 | 16.7 | 1.50 | 2.60 | 6.42 |
| 308 | 58.50 | 5.30 | 0.09 | 11.6 | 0.46 |
| 309 | 10.60 | 3.00 | 0.28 | 0.81 | 3.70 |
| 310 | 929.0 | 82.9 | 0.09 | 9.20 | 9.01 |
| 312 | 0.044 | 0.06 | 1.36 | 0.15 | 0.40 |
| TMQ | 0.042 | 0.003 | 0.07 | 0.01 | 0.30 |
| PTX | 0.038 | 0.001 | 0.04 | 0.01 | 0.14 |
| TMP | 12.0 | 133.0 | 11.1 | 2.7 | 49.0 |
| MTX | 0.001 | 0.003 | 3.0 | 0.014 | 0.21 |

*ND = not determined

As can be seen from the above table, Compound 4 is almost two-times as selective at TMP and 306 times as selective as TMQ. Compound 8 similarly showed much higher selectivity than the compounds known in the art. These two compounds, therefore, represent preferred embodiments of the invention for the treatment of infections caused by *Pneumocystis carinii* and *Toxoplasmosis gondii* as well as in treatment of cancer patients as an antitumor agent or to destroy cancerous cells. With regard to *Pneumocystis carinii*, Compounds 4 and 8, with their high potency and high selectivity, may be used clinically with a lesser amount of a leucovorin as compared to TMQ or may be used clinically without the necessity of leucovorin, and thus greatly reduce the cost of administering these compounds to a patient.

Example 2

Compound 9 was tested for DHFR inhibition against the growth of human leukemia CCRF-CEM cells. The performance of Compound 9 was evaluated against MTX. Four different types of cells were used: CCRF-CEM cells were unaltered; R30dm cells had a decreased amount of polyglutamate synthase; R1 cells had a twenty-fold increase in wild type DHFR protein and activity; and R2 cells were deficient in their ability to uptake the compounds into the cell. Results are presented in Table 8 below.

TABLE 8

Growth Inhibition of Parental CCRF-CEM and Sublines with Single, Defined Mechanisms of MTX Resistance During Continuous (0–120 hours) Exposure to MTX and Compound 9 ($EC_{50}$ in nM)

| Compound | CCRF-CEM | R30dm | R1 | R2 |
|---|---|---|---|---|
| MTX | 14.5 ± 0.4 (n = 5) | 14.5 ± 0.5 (n = 2) | 595 ± 5 (n = 2) | 3100 ± 100 (n = 2) |
| 9 | 12.8 ± 2.2 | 36 ± 1 | 515 ± 25 | 1650 ± 200 |

TABLE 8-continued

Growth Inhibition of Parental CCRF-CEM and Sublines with Single, Defined Mechanisms of MTX Resistance During Continuous (0–120 hours) Exposure to MTX and Compound 9 ($EC_{50}$ in nM)

| Compound | CCRF-CEM | R30dm | R1 | R2 |
|---|---|---|---|---|
| | (n = 5) | (n = 2) | (n = 2) | (n = 2) |

Average values are presented ± the standard deviation range for n=2 and ± the standard deviation range for n≧3.

As can be seen from the results of the above table, Compound 9 performed comparably to MTX. The example further demonstrates that polyglutamylation may play a limited role in the mechanism of action of Compound 9, even in continuous exposure. Both the $R_1$ subline, with amplified DHFR expression, and the MTX-transport deficient $R_2$ subline displayed resistance to MTX under continuous exposure.

Example 3

Compound 9 and MTX were also tested for growth inhibition of A253 and FaDu human squamous carcinoma cell lines; neither of these cell lines had any deficiencies. Results are presented below in Table 9.

TABLE 9

Growth Inhibition of A253 and FaDu Human Squamous Carcinoma Cell Lines Following Continuous (120 hours) Exposure to MTX and Compound 9 ($EC_{50}$ in nM)

| Compound | A253 | FaDu |
|---|---|---|
| MTX | 17 ± 1 | 31 ± 2 |
| 9 | 46 ± 4 | 22 ± 4 |

All values are average ± standard deviation range for duplicate determinations.

Example 4

Compound 9 and aminopterin were further tested for their activity as substrates for human leukemia cell CCRF-CEM folylpolyglutamate synthetase. Aminopterin is a classical 2,4-diamino antifolate substrate. Results are presented below in Table 10.

TABLE 10

Activity of Aminopterin and Compound 9 as Substrates for CCRF-CEM Human Leukemia Cell Folylpolyglutamate synthetase

| Substrate | KM, μM | $V_{max, rel}$ | $V_{max}/K_{m(rel)}$ | n |
|---|---|---|---|---|
| Aminopterin | 4.3 ± 0.2 | 1 | 0.23 ± 0.01 | 3 |
| 9 | <1 | 0.72 ± 0.07 | >0.72 | 4 |

Values presented are average ± standard deviation.

This example demonstrates that Compound 9 is a potent tumor cell growth inhibitor that shares determinates of response with MTX. It is similar in potency to MTX as an inhibitor of the growth of human leukemia and SCC cell lines in culture. DHFR is suggested as the target of Compound 9, which is supported by the data showing relatively potent DHFR inhibition in vitro and the cross-resistance to Compound 9 of a human cell line having amplified expression of DHFR. Compound 9 may also use the MTX/reduced folate-transport protein for uptake as evidenced by the cross-resistance of a human cell line in which this transport system is defective. This example indicates that Compound 9 may be an excellent substrate for human FPGS with a very low $K_m$. The slight cross-resistance to continuous exposure of the cell line having low levels of FPGS suggests that polyglutamate metabolites may play a role in growth inhibition even under these conditions.

Example 5

Compound 9 was further tested for its in vitro anti-cancer activity by the National Cancer Institute. Results are presented in Table 11 below. $GI_{50}$ represents the concentration at which growth was inhibited by 50%.

TABLE 11

In Vitro Anti-Cancer Activity of Compound 9

| Panel/Cell Line | $GI_{50}$ |
|---|---|
| Leukemia | |
| CCRF-CEM | ND |
| HL-60 (TB) | ND |
| MOLT-4 | ND |
| RPML-8226 | ND |
| SR | >1.00E-04 |
| Non-Small Cell Lung Cancer | |
| A549/ATCC | <1.00E-08 |
| EKVX | 3.97E-05 |
| HOP-62 | <1.00E-08 |
| HOP-92 | 8.40E-06 |
| NCI-H226 | >1.00E-04 |
| NCI-H23 | 5.75E-08 |
| NCI-H322M | >1.00E-04 |
| NCI-H522 | >1.00E-04 |
| Colon Cancer | |
| COLO 205 | >1.00E-04 |
| HCC-2998 | <1.00E-08 |
| HCT-116 | <1.00E-08 |
| HCT-15 | <1.00E-08 |
| HT29 | <1.00E-08 |
| KM12 | 3.32E-05 |
| SW-620 | 3.15E-06 |
| CNS Cancer | |
| SF-268 | <1.00E-08 |
| SF-295 | <1.00E-08 |
| SF-539 | <1.00E-08 |
| SNB-19 | >1.00E-04 |
| SNB-75 | <1.00E-08 |
| U251 | <1.00E-08 |
| Melanoma | |
| LOX IMVI | <1.00E-08 |
| MALME-3M | <1.00E-08 |
| M14 | <1.00E-08 |
| SK-MEL-2 | >1.00E-04 |
| SK-MEL-28 | >1.00E-04 |
| UACC-257 | ND |
| UACC-62 | <1.00E-08 |
| Ovarian Cancer | |
| IGROV1 | <1.00E-08 |
| OVCAR-3 | >1.00E-04 |
| OVCAR-4 | >1.00E-04 |
| OVCAR-5 | >1.00E-04 |
| OVCAR-8 | <1.00E-08 |
| SK-OV-3 | >1.00E-04 |
| Renal Cancer | |
| 786-0 | <1.00E-08 |
| ACHN | <1.00E-08 |
| CAKI-1 | <1.00E-08 |
| RXF 393 | >1.00E-04 |
| SN12C | <1.00E-08 |

TABLE 11-continued

In Vitro Anti-Cancer Activity of Compound 9

| Panel/Cell Line | GI$_{50}$ |
|---|---|
| TK-10 | >1.00E-04 |
| UO-31 | <1.00E-08 |
| Prostate Cancer | |
| PC-3 | >1.00E-04 |
| DU-145 | 1.09E-08 |
| Breast Cancer | |
| MCF7 | <1.00E-08 |
| MCF7/ADR-RES | <1.00E-08 |
| MDA-MB-231/ATCC | >1.00E-04 |
| HS 578T | >1.00E-04 |
| MDA-MB-435 | 6.87E-07 |
| MDA-N | <1.00E-08 |
| BT-549 | >1.00E-04 |
| T-47D | >1.00E-04 |

As will be appreciated by one skilled in the art, the lower the GI$_{50}$, the more effective the compound. A GI$_{50}$ of less than $1.00 \times 10^{-8}$ indicates a very high potency, whereas a GI$_{50}$ greater than $1.00 \times 10^{-4}$ indicates that the compound was relatively inactive.

As demonstrated in Table 11 above, Compound 9 was shown to be highly selective against certain cell lines, with little or no activity against other cell lines. This result indicates that Compound 9 is not a general poison, but rather is very selective. For example, in the eight breast cancer cell lines, Compound 9 was found to be highly potent, with GI$_{50}$ of less than $1.00 \times 10^{-8}$M, against the MCF7, MCF7-ADR-RES (resistant cell line) and the MDA-N cell lines, but was relatively inactive, with GI$_{50}$ greater than $1.00 \times 10^{-4}$M against breast cancer cell lines MDA-MB-231/ATCC, HS578T, BT-549 and T47D. The difference in activity of these two sets of breast cancer cells is ten thousand fold, which indicates a very high degree of selectivity. This kind of selectivity is repeated in all of the cell lines tested.

Example 6

The inhibitory concentration of Compounds 313 and 314 against TS was determined. The performance of these compounds was measured against PDDF, which is a standard TS inhibitor and experimental anticancer agent. The compounds were all tested against *Lactobacillus casei* and human lymphoma cells. Results are presented in Table 12 below:

TABLE 12

Inhibitory Concentrations (IC$_{50}$ in µM) Against TS

| Compound | *L. Casei* TS | Human TS |
|---|---|---|
| 313 | 180 | 180 |
| 314 | 360 | ND |
| PDDF | 0.036 | 0.036 |

As can be seen from the above table, Compound 313 and 314, when tested, had surprisingly high inhibitory concentration when compared with that of PDDF.

Example 7

Compounds 315 and 317–322 were tested for their inhibitory activity against TS. The performance of these compounds was measured against ZD1694, which is in Phase III clinical trials as an antitumor agent. All of the compounds were tested against human cells, *L. casei, E. coli,* and *S. faecium*. Results are presented in the Table 13 below. As can be seen in the table, compounds 318 and 320 are more potent than ZD1694.

TABLE 13

Inhibitory Concentrations (IC$_{50}$ in µM) Against TS

| Compound | Human | *L. Casei* | *E. Coli* | *S. Faecium* |
|---|---|---|---|---|
| ZD1694 | 0.22 | 8.8 | 5.3 | 8.8 |
| 315 | >25 | >26 | ND | ND |
| 317 | 2.4 | >24 (33%) | >24 (30%) | >24 (12%) |
| 318 | 0.13 | 45 | 45 | >45 (31%) |
| 319 | 1.0 | >26 (0%) | >26 (40%) | 30 |
| 320 | 0.15 | 5.1 | 13 | 15 |
| 321 | 30 | >30 (0%) | >30 (30%) | >30 (20%) |
| 322 | 2.0 | >25 (32%) | >25 (36%) | >25 (0%) |

Example 8

Compounds 317–320 were also tested for their ability to inhibit DHFR. Selectivity ratios were determined as measured against *Pneumocystis carinii* (Pc), *Toxoplasmosis gondii* (Tg) and rat liver (RL). Results are presented in Table 14 below.

TABLE 14

Inhibition of Dihydrofolate Reductase (IC$_{50}$ in µM)

| Compound | Pc | RL | Selectivity Ratio RL/Pc | Tg | Selectivity Ratio RL/Tg |
|---|---|---|---|---|---|
| 317 | >21 | >21 | ND | 20 | >1 |
| 318 | >20 | >20 | ND | 11.7 | >1.7 |
| 319 | 40 | 24.6 | 0.62 | 3.1 | 7.94 |
| 320 | >15 | 7470 | ND | 244 | 30.61 |

As can be seen from Table 14, Compound 320 is highly selective for *Toxoplasmosis gondii* DHFR.

Example 9

Compounds 317–322 were also tested for their ability to inhibit the growth of FaDu human squamous cell carcinoma cell lines. The performance of these compounds was tested against PDDF, and AG331, which is a TS inhibitor in Phase III clinical trials as an antitumor agent. Results are presented in Table 15 below.

TABLE 15

Growth Inhibition of the FaDu Human Squamous Cell Carcinoma Cell Line By Continuous (120 hours) Exposure to the Inhibitors

| Compound | EC$_{50}$ µM | n |
|---|---|---|
| 317 | >10 | 2 |
| 318 | insoluble | — |
| 319 | 6.7 ± 1.5 | 3 |
| 320 | 1.5 ± 0.4 | 3 |
| 321 | >10 | 2 |
| 322 | ND | — |
| PDDF | 1.7 ± 0.2 | 4 |
| AG331 | 1.0 ± 0.1 | 6 |

Values presented are average ± standard deviation.

Example 10

The following example describes methods of synthesizing the compounds represented by formula 2. These methods are illustrated in FIG. 1. Reference numerals and letters correspond with those of FIGS. 1 and 2.

2-amino-3,4-dicyanopyrrole (11)

A mixture of about 4.0 grams (g) of Compound 10, about 4.0 g of 5% Pd on $BaCO_3$, about 15 milliliters (ml) of DMF and about 25 ml methanol was hydrogenated at about 50 psi for approximately 3 hours. The mixture was filtered through Celite®, a filtering composition commercially available from Johns-Mannville Products Corporation, and the filtrate concentrated under reduced pressure to about 10 ml. About 200 ml of cold water was added to the concentrate, and a light brown solid was formed. This solid was collected by filtration to yield about 1.60 g of Compound 11.

2,4-diamino-5-cyanopyrrolo[2,3-d]pyrimidine (12)

A mixture of about 2.63 g of Compound 11 and about 2.5 g of chlorformamidine hydrochloride in about 50 ml Dowtherm-A®, a liquid heat transfer media commercial available from Dow Chemical Company, was heated at between about 160° and 170° C. for approximately 48 hours, until Compound 11 could not be detected by thin layer chromatography (TLC). The mixture was cooled to room temperature, and about 50 ml of $Et_2O$ was added thereto. A greenish-brown solid resulted. The solid was filtered and washed with $Et_2O$ to yield about 3.0 g of Compound 12.

2,4-diaminopyrrolo[2,3-d]pyrimidine-5-carboxaldehyde (13)

About 6.0 g of Raney Ni was added to a stirred solution of about 2.0 g of Compound 12 and about 50 ml of HCOOH. The mixture was heated to about 80° C. for about 2 hours, until no starting material could be detected by TLC. The mixture was cooled to room temperature and filtered through Celite®. The filtrate was evaporated under reduced pressure, azeotroping with methanol to remove traces of HCOOH. The residue was dissolved in about 25 ml of hot water, treated with Norit®, an activated adsorption carbon commercially available from American Norit Company, Inc., and filtered through Celite®. The filtrate was neutralized with $NH_4OH$. The light brown precipitate which resulted was filtered and dried to yield about 1.40 g of Compound 13, which was immediately used in subsequent reactions without further purification.

2,4-diamino-5[[N-(3',4',5'-trimethoxyphenyl)imino]methyl]pyrrolo]2,3-d]pyrimidine (14a)

A solution containing about 1.30 g of Compound 12 and about 2.06 g of 3,4,5-trimethoxyaniline in about 75 ml of 70% acetic acid and containing about 6.50 g of damp Raney Ni was hydrogenated at atmospheric pressure for about 24 hours at room temperature. The mixture was treated with Norit® and filtered through Celite® and the solvent removed from the filtrate by evaporation under reduced pressure. About 15 ml of cold water was added to the residue, and the suspension was added to about 100 ml of a stirred, cold, saturated solution of $NaHCO_3$. The mixture was stirred for about 10 minutes and refrigerated for about 6 hours. The brown precipitate which formed was collected, washed with water, and dried. This product, containing Compound 14A, was washed repeatedly with $Et_2O$ until no aniline was detected by TLC in the washings. The residue was then dissolved in about 100 ml methanol and filtered, and the filtrate evaporated under reduced pressure to near dryness. About 50 ml $Et_2O$ was added to the solution, and the precipitate filtered to yield about 1.20 g of Compound 15a.

2,4-diamino-5-[(3',4',5'-trimethoxyanilino)methyl]pyrrolo[2,3-d]pyrimidine (1)

About 0.05 g $NaCNBH_3$ were added to a solution containing about 0.20 g of Compound 15a in about 25 ml methanol. The pH was adjusted to about 2 with a 50% methanol/hydrochloric acid solution. The mixture was continuously stirred at room temperature for about 4 hours. The solvent was evaporated to dryness, and cold water was added to the residue, which was neutralized with $NH_4OH$. The resulting precipitate was filtered, dried, and dissolved in a 9:1 mixture of $CHCl_3$/(methanol. This was applied to a silica gel column (2.4cm×20 cm) packed in $CHCl_3$. The column was eluted with a gradient of 1% methanol in $CHCl_3$ to 15% methanol in $CHCl_3$. Fractions corresponding to the product, as determined by TLC, were pooled and evaporated to dryness under reduced pressure. The residue was triturated in cold $Et_2O$ and filtered to yield about 0.10 g of Compound 1.

2,4-diamino-5-[(3',4'-dimethoxyanilino)methyl]pyrrolo[2,3-d]pyrimidine (2)

The Schiff base was prepared as described for Compound 15a, except that the reaction was carried out in 80% acetic acid and using 3,4-dimethoxyaniline to yield about 1.20 g of Compound 15b. Reduction of Compound 15b was carried out as described for Compound 1. The crude product was dissolved in methanol and filtered. The filtrate was evaporated under reduced pressure to dryness. The residue was triturated in cold $Et_2O$ and filtered to yield about 0.51 g of Compound 2.

2,4-diamino-5-[(4'-methoxyanilino)methyl]pyrrolo[2,3-d]pyrimidine (3)

The Schiff base was prepared as described above for Compound 15b using 4-methoxyaniline to yield about 0.32 g of Compound 15c. Reduction of Compound 15c was carried out as described for Compound 15b to yield Compound 3.

2,4-diamino-5-[(2',5'-dimethoxyanilino)methyl]pyrrolo[2,3-d]pyrimidine (4)

The Schiff base was prepared as described above for Compound 15b using 2,5-dimethoxyaniline to yield about 0.90 g of Compound 15d. Reduction of Compound 15d was carried out as described above for Compound 15b to yield about 0.25 g of Compound 4.

2,4-diamino-5-[[(2',5'-diethoxphenyl)imino]methyl]-pyrrolo[2,3-d]pyrimidine (15e)

Method A, starting from Compound 13: A solution of about 1.15 g of Compound 13 and about 1.76 g of 2,5-diethoxyaniline (14e) in about 75 ml 70% acetic acid containing about 5.75 g of damp Raney Ni was hydrogenated at about 55 psi for about 12 hours at room temperature. The mixture was filtered through Celite® and the filtrate evaporated under reduced pressure. About 15 ml cold water were added to the residue and this suspension was added to about 100 ml of a stirred, cold, saturated solution of $NaHCO_3$. The mixture was stirred for an additional 10 minutes and refrigerated for about 4 hours. The brown precipitate which resulted was collected, washed with water, and dried. The crude product containing Compound 14e was washed repeatedly with $Et_2O$ until no aniline could be detected by TLC in the washings. The residue was then dissolved in about 100 ml methanol and filtered, and the filtrate evaporated to dryness under reduced pressure. About 20 ml Et$_2$O was added to the solution, and the precipitate filtered to yield about 1.20 g of Compound 15e.

Method B, starting from Compound 12: The Schiff base was prepared as described above for Compound 15b using 2,5-diethoxyaniline to yield about 0.90 g of Compound 15e, which was identical in all respects with the sample prepared according to Method A described above.

2,4-diamino-5-[(2',5'-diethoxyanilino)methyl]pyrrolo [2,3-d]pyrimidine (5)

Reduction of Compound 15e was performed as described above for Compound 15b to yield about 0.36 g of Compound 5.

2,4-diamino-5-[(3',4'-dichloroanilino)methyl]pyrrolo [2,3-d]pyrimidine (6)

The Schiff base was prepared as described above for Compound 15b using 3,4-dichloroaniline to yield about 1.0 g of Compound 15f. Reduction of Compound 15f was performed as described above for Compound 15b to yield about 0.34 g of Compound 6.

2,4-diamino-5-[(1'-naphthylamino)methyl]pyrrolo[2,3-d]pyrimidine (7)

The Schiff base was prepared as described above for Compound 15b, except that the reaction was carried out at about 30 psi for about 12 hours at room temperature using 1-aminonaphthylene to yield about 0.92 g of Compound 15 g. Reduction of Compound 15 g was carried out as described above for Compound 15b, except that glacial acetic acid was used to adjust the pH to about 2. Crude product 7 was dissolved in a 9:1 mixture of CHCl$_3$/methanol, which was loaded on a silica gel column (2.4cm×20 cm) packed in CHCl$_3$. The column was eluted with a gradient of 1% methanol in CHCl$_3$ to 5% methanol in CHCl$_3$. Fractions corresponding to the product, as determined by TLC, were pooled and evaporated under reduced pressure to dryness. The residue was triturated in cold Et$_2$O and the suspension filtered to yield about 0.24 g of Compound 7.

2,4-diamino-5-(anilinomethyl)pyrrolo[2,3-d] pyrimidine (8)

The Schiff base was prepared as described above for Compound 15b using aniline to yield about 0.69 g of Compound 15h. Reduction of Compound 15h was carried out as described for Compound 15b, except that glacial acetic acid was used to adjust the pH to about 2. About 0.19 g of Compound 8 resulted.

N-[4-[N-](2,4-diaminopyrrolo[2,3-d]pyrimidin-5-yl) methyl]amino]benzoyl]-L-glutamic acid (9)

The Schiff base was prepared as described above for Compound 15b using diethyl(p-aminobenzoyl)-L-glutamate to yield about 1.39 g of the diethylester of Compound 16. Reduction of Compound 16 was carried out as described above for Compound 15b to yield about 0.44 g of Compound 17. Hydrolysis of the esters was carried out by stirring a solution of about 0.30 g Compound 17 in about 10 ml of 1N sodium hydroxide and 10 ml methanol for about 72 hours at room temperature. The solvent was evaporated to 5 ml, and the mixture was carefully acidified with glacial acetic acid in an ice bath. The tan precipitate which resulted was filtered, washed with water, and dried to yield about 0.23 g of Compound 9.

Example 11

The DHFR inhibitory concentrations of Compounds 159–169, 171, 172, 175, 177, 178, and 179 was determined. Performance of these compounds was measured against TMQ and TMP. Inhibitory concentration was measured against *Pneumocystis carinii* and *Toxoplasmosis gondii*, as well as rat liver. Results are presented in Table 16 below.

TABLE 16

Inhibitory Concentrations (IC$_{50}$, μM) and Selectivity Ratios of 5-substituted furo[2,3-d]pyrimidines

| Compound # | Pc DHFR | RL DHFR | Selectivity Ratio RL/Pc | Tg DHFR | Selectivity Ratio RL/Tg |
|---|---|---|---|---|---|
| 159 | >26 | 252 | ND | >26 | ND |
| 160 | 19 | 23 | 1.2 | 19 | 1.2 |
| 161 | 0.65 | 12.3 | 18.9 | 11.6 | 1.1 |
| 162 | 13.5 | 12 | 0.89 | 37 | 0.32 |
| 163 | 41 | 36.5 | 0.89 | 38 | 0.96 |
| 164 | 14 | 60.3 | 4.31 | >42 | ND |
| 165 | >12 | >12 | ND | >12 | ND |
| 166 | 8.1 | 16.2 | 2.00 | 32.4 | 0.50 |
| 167 | 7.7 | 187 | 17.79 | 45.4 | 3.02 |
| 169 | 50.9 | 71.9 | 1.4 | >47 | ND |
| 171 | 44.8 | >27 | ND | >27 | ND |
| 172 | 284 | 34.3 | 0.1 | 21.5 | 1.6 |
| 175 | >31.3 | >31.3 | ND | >31.3 | ND |
| 177 | 8.6 | >83 | >10 | >83 | ND |
| 178 | >12 | >12 | ND | >12 | ND |
| 179 | >27.9 | >27.9 | ND | >27.9 | ND |
| TMQ | 0.042 | >0.003 | 0.07 | 0.01 | 0.30 |
| TMP | 12 | 133 | 11.1 | 2.7 | 49.0 |

As can be seen from the above table, Compound 161 is approximately 18 times more active than TMP and 1.7 times more selective; Compound 161 is 271 times more selective than TMQ and only 15 times less potent. These compounds, therefore, exhibit high selectivity for Pc DHFR. Compound 167 was also more selective than the compounds known in the art.

Example 12

Figure 6:
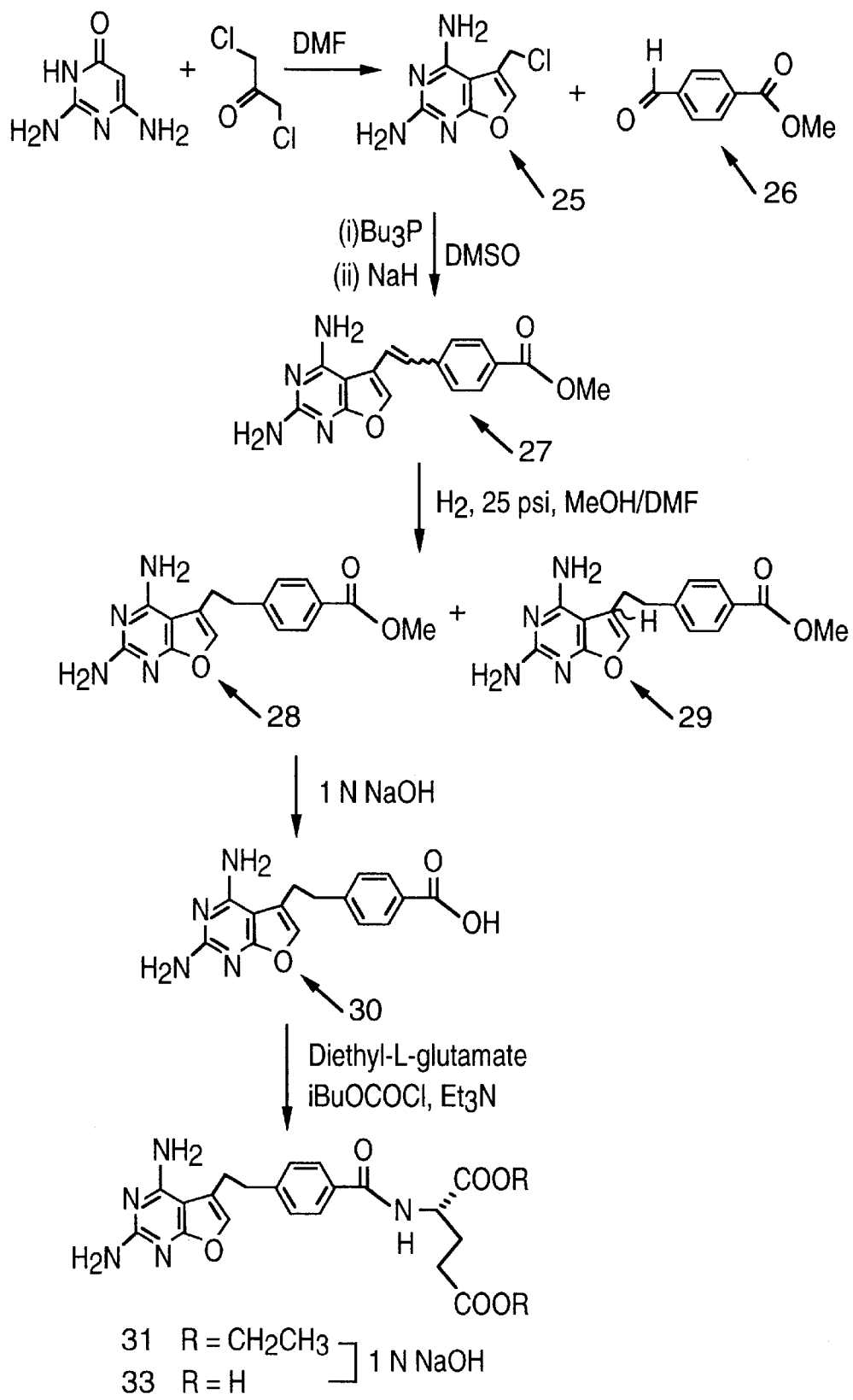
FIG. 6 shows a schematic diagram of the methods of preparing two of compounds having formula 4.
Figure 7:
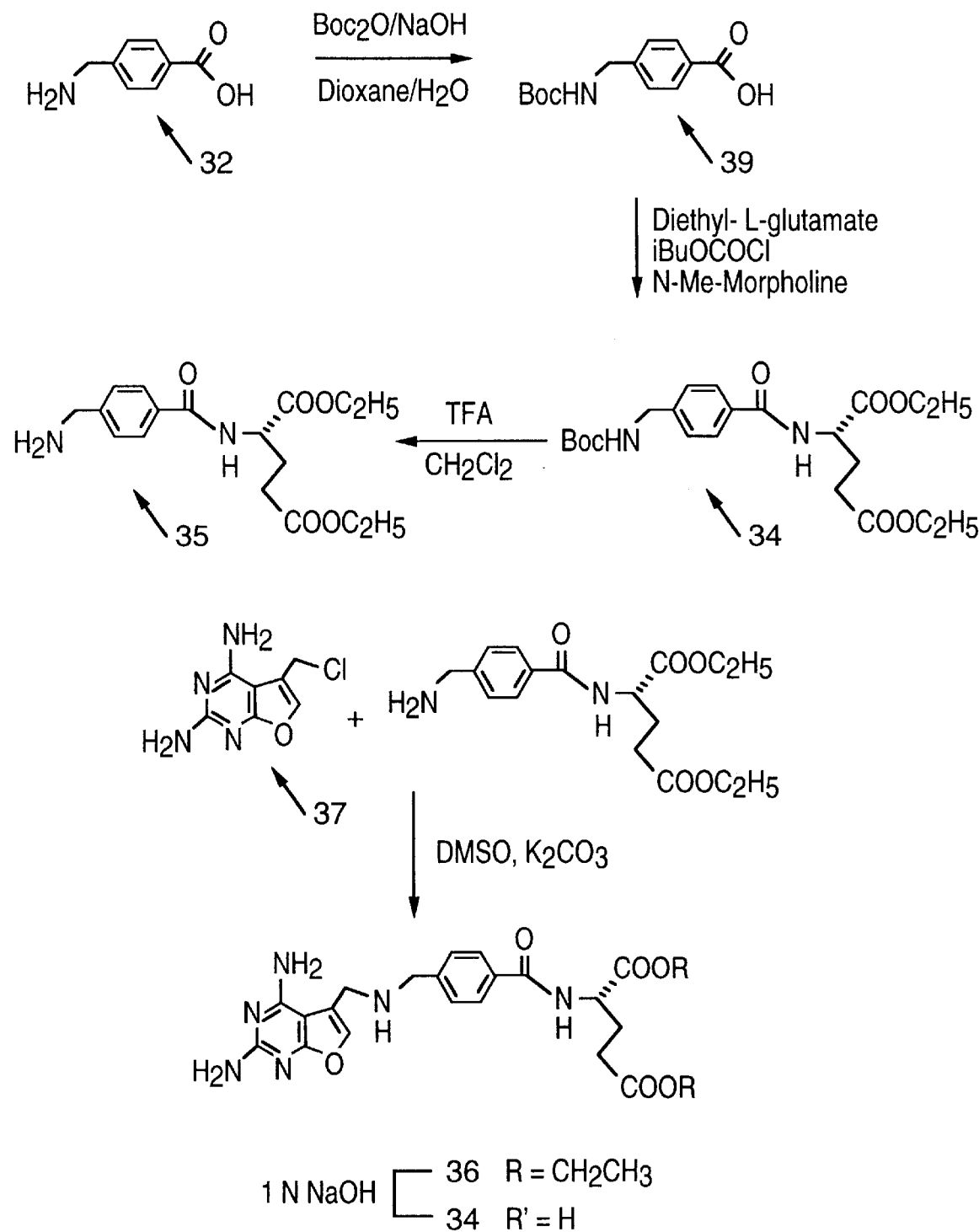
FIG. 7 shows a schematic diagram of the methods of preparing two of compounds having formula 4.
Figure 8:
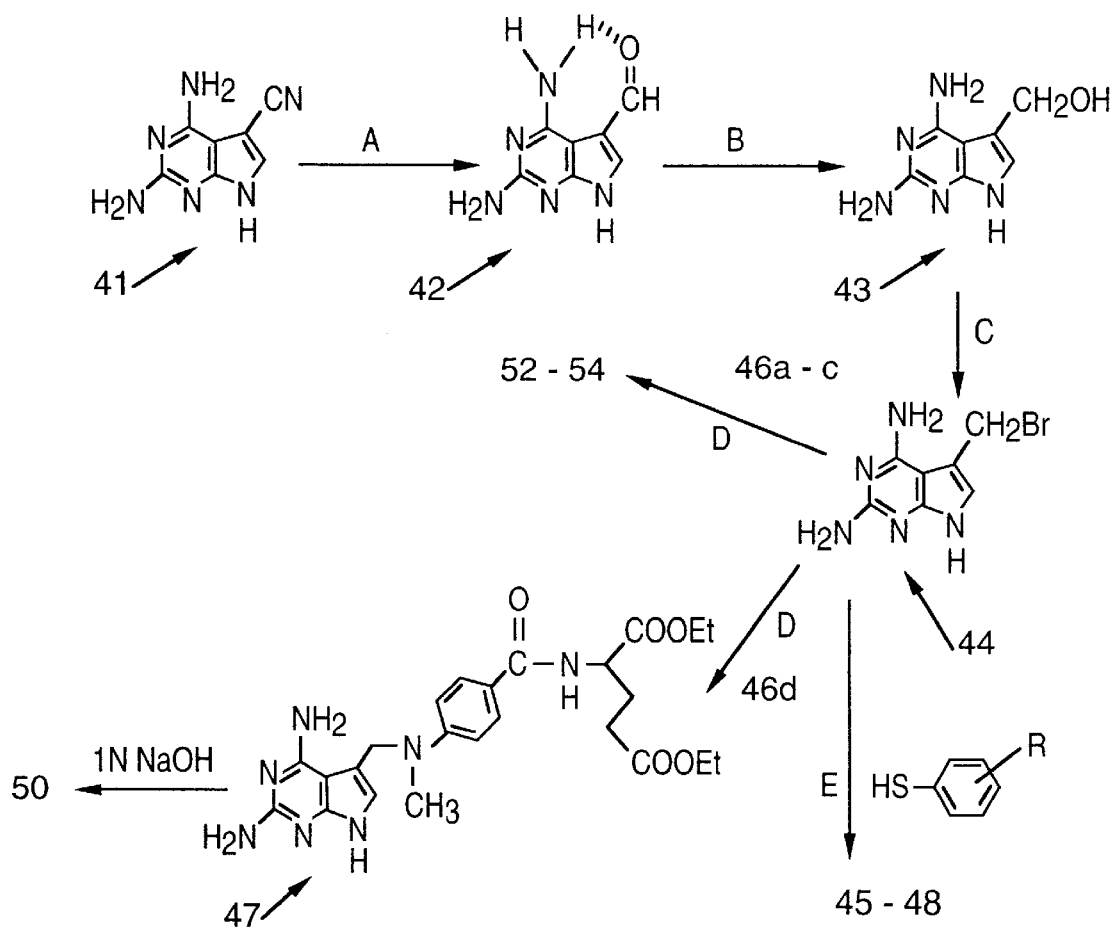
FIG. 8 shows a schematic diagram of the methods of preparing compounds having formula 9.
Figure 9:
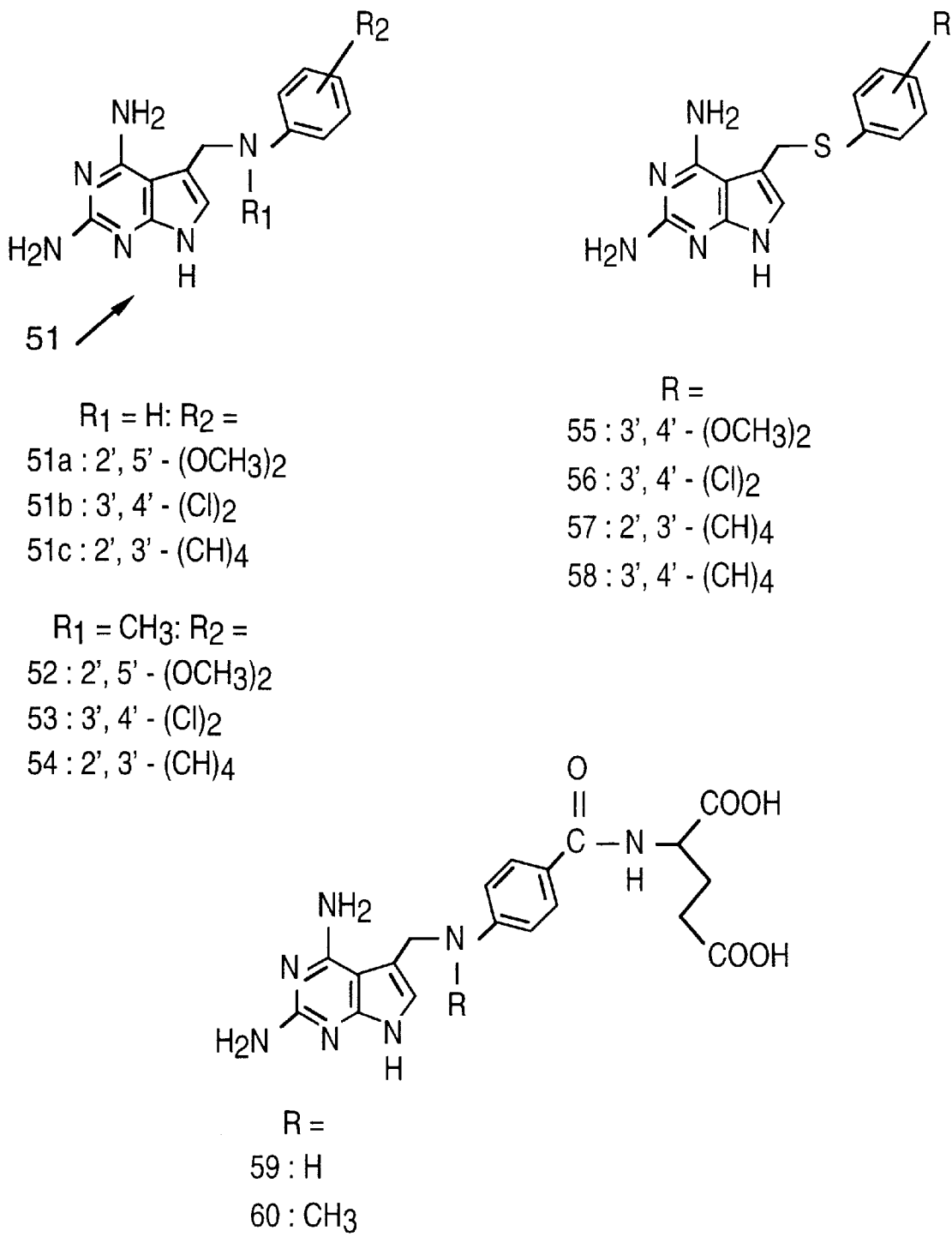
FIG. 9 shows of compounds having formula 9 as synthesized by the methods shown in FIG. 8.

The following example provides methods for synthesizing compounds of formula 4. Reference numerals correspond with those in FIGS. 6 and 7.

Methyl 4-[2-(2,4-diaminofuro[2,3-d]pyrimidin-5-yl)-ethanyl]benzoate(27)

About 2.64 g of tributylphosphine was added to a solution containing about 0.79 g of 2,4-diamino-5(chloromethyl)furo [2,3-d]pyrimidine (25) in about 10 ml anhydrous DMSO. The mixture was stirred at about 60° C. for about 2 hours under nitrogen to form the phosphonium salt. The solution was cooled to room temperature, at which time 0.35 g of sodium hydride (60% dispersion in mineral oil) followed by about 0.72 g of methyl 4-formylbenzoate (26) was added. The mixture was stirred for about 24 hours at room temperature. The DMSO was removed by vacuum distillation. About 50 ml of ethylether was added to the residue and the supernatant decanted after 10 minutes. About 50 ml of ethylether was added again, the residue stirred for about 1 hour, and the supernatant decanted. This process was repeated 3 more times; the mixture was then stored at 0° C. with about 50 ml ethylether. After about 18 hours, the mixture was ultrasonicated for 2 hours and cooled to 0° C. for a period of about 10 hours. The resulting solid was filtered, washed with ethylether, air dried, washed with water and air dried again. The solid was then suspended in about 250 ml of hot methanol. About 3 g of silica gel were added to the filtrate, and the suspension was evaporated to dryness under reduced pressure. The silica gel plug was loaded on a dry silica gel column (2.4×20 cm) and flushed initially with $CHCl_3$ (500 ml). The column was then eluted sequentially with 100 ml portions of 1% to 8% methanol in $CHCl_3$. Fractions which showed a major spot at $R_f$ 0.66, as determined by TLC, were pooled and evaporated to dryness. The resulting residue was dissolved in glacial acetic acid and evaporated to dryness. This residue was redissolved in hot methanol and the solution stored at 0° C. for about 72 hours. The resulting solid was filtered, washed with ether, and dried to yield about 0.52 g of Compound 27.

Methyl 4-[2-(2,4-diaminofuro[2,3-d]pyrimidin-5-yl) ethyl]benzoate (28) and (±)-methyl 4-]2-(2,4-diamino-5,6-dihydrofuro[2,3-d]pyrimidin-5-yl)ethyl] benzoate (29)

About 0.31 g of 5% palladium on carbon was added to a solution containing about 0.155 g of Compound 27 in about 20 ml of a 1:1 mixture of methanol/DMF. The suspension was hydrogenated in a Parr apparatus at room temperature and 25 psi of hydrogen pressure for 30 minutes. The reaction mixture was filtered through Celite®, and the catalyst was washed with about 30 ml of a 1:1 methanol/DMF mixture. The filtrate was evaporated to dryness under reduced pressure, and the residue dissolved in about 100 ml methanol. About 500 mg of silica gel was added to the solution, and evaporated to dryness. The silica gel plug was loaded on a dry silica gel column (2.4×16 cm) and flushed with about 500 ml $CHCl_3$. The column was then eluted with a gradient of 1–9% methanol in $CHCl_3$, collecting 15 ml fractions. Fractions showing a single spot at $R_f$ 0.63, as determined by TLC, were pooled and evaporated to dryness, and the residue was stirred in ether, filtered, and dried to yield about 0.08 g of Compound 28. Later fractions from the column described above, showing a single spot at $R_f$ 0.52, were pooled and evaporated to dryness under reduced pressure, and the residue obtained was stirred in ether, filtered, and dried to yield about 0.02 g of Compound 29.

4-[2-(2,4-diaminofuro[2,3-d]pyrimidin-5-yl)ethyl] benzoic acid (30)

About 1.5 ml of 1N sodium hydroxide was added to a solution containing about 0.065 g of Compound 28 in about 10 ml of a mixture of 2:1 methanol/DMSO. The mixture was stirred at room temperature for 18 hours and evaporated to dryness under reduced pressure (oil pump). The residue was dissolved in about 5 ml water and 1N HCl was added dropwise to bring the pH of the solution to 5.5. The suspension was cooled to 5° C. for about 12 hours and filtered. The residue was washed sequentially with water, acetone and ether and dried to yield about 0.05 g of Compound 30.

N-[4-[2-(2,4-diaminofuro[2,3-d]pyrimidin-5-yl) ethyl]-benzoyl]-L-glutamic acid (33)

About 45 microliters of triethylamine was added to a suspension containing about 0.047 g of Compound 30 in about 3 ml anhydrous DMF, and the mixture stirred under nitrogen at room temperature for about 5 minutes. The solution was cooled to 0° C., about 42 microliters of isobutylchloroformate was added, and the mixture stirred at 0° C. for 30 minutes. About 0.077 g of diethyl-L-glutamate hydrochloride was added to the reaction mixture, followed immediately by about 45 microliters triethylamine. The mixture was slowly allowed to warm to room temperature, and stirred under nitrogen for a period of about 18 hours. The reaction mixture was then subjected to another cycle of activation using ½ of the quantities listed above. The reaction mixture was warmed to room temperature and stirred for 24 hours and evaporated to dryness under reduced pressure. The residue was dissolved in a 4:1 mixture of $CHCl_3$/methanol and chromatographed on a silica gel column (2.4×15 cm), packed with $CHCl_3$/methanol (24:1), eluting with 24:1 $CHCl_3$/methanol. Fractions showing a single spot were pooled and evaporated to dryness. The residue was stirred in cold anhydrous ether and filtered to obtain about 0.054 g of Compound 31. About 1 ml of 1N sodium hydroxide was added to a solution containing about 0.052 g of Compound 31 in about 5 ml methanol and the solution stirred at room temperature for 24 hours. The methanol was evaporated under reduced pressure, the residue dissolved in about 5 ml water, and stirring was continued for an additional 24 hours. The pH of the solution was then adjusted to 4.0 by dropwise addition of 1N HCl. The-resulting suspension was stored at 5° C. for about 12 hours and filtered; the residue was washed well with water and acetone and dried to yield about 0.044 g of Compound 33.

4-[[N-(tert-butyloxycarbonyl)amino]methyl]benzoic acid (39)

About 10 ml of 1N sodium hydroxide was added to a solution containing about 1.51 g of 4-(aminomethyl)benzoic acid (32) in about 20 ml of 1:1 dioxane/water. The mixture was stirred at room temperature for about 12 hours, and evaporated to half of its original volume under reduced pressure. The pH of the solution was adjusted to 3 by dropwise addition of 50% aqueous HCl, while maintaining the temperature below 10° C. with an ice bath. The resulting suspension was diluted with water (70 ml) and extracted with ethylacetate (3×50 ml). The combined organic layers were washed with about 50 ml saturated NaCl, dried $MgSO_4$, and filtered. The filtrate was evaporated to dryness under reduced pressure and the residue recrystallized from a mixture of ethylacetate/hexanes to yield about 2.10 g of Compound 39.

Diethyl-N-[4-[[N-(tert-butyloxycarbonyl)amino] methyl]benzoyl]-L-glutamate (34)

A solution containing about 1.26 g of Compound 39 in about 20 ml anhydrous DMF under nitrogen was cooled in an ice-salt bath. About 0.55 ml of N-methylmorpholin was added to the cooled solution, followed 5 minutes later by about 0.65 ml isobutylchloroformate. After stirring for a period of about 20 minutes, 1.20 g diethyl-L-glutamate hydrochloride was added, followed immediately by about 0.55 ml N-methylmorpholin. The reaction mixture was warmed to room temperature and stirred for 12 hours. At this time, the activation cycle was repeated using ½ the amounts of reagents indicated above, after which the reaction mixture was warmed to room temperature and stirred for an additional 12 hours. The solvents were removed under reduced pressure, and the residue was dissolved in about 100 ml $CH_2Cl_2$, washed with about 75 ml water, 50 ml 0.1 NHCl, and about 50 ml saturated NaCl. The organic layers were dried ($MgSO_4$) and filtered. The filtrate was evaporated under reduced pressure and the residue was flash chromatographed on silica gel (2.4×24 cm), eluting first with $CH_2Cl_2$ and then with 1% methanol in $CH_2Cl_2$. Fractions showing a single spot corresponding to the product were pooled and evaporated under reduced pressure to yield about 1.29 g of Compound 34.

Diethyl N-[4-(aminomethyl)benzoyl]-L-glutamate (35)

About 1.8 ml trifluoroacetic acid was added dropwise to a stirred solution containing about 1.0 g of Compound 34 in about 20 ml $CH_2Cl_2$. The mixture was stirred at room temperature for 15 minutes, evaporated to dryness under reduced pressure, and co-evaporated twice with about 30 ml absolute ethanol. The residue was then subjected to column chromatography on silica gel (1.5×15 cm), eluting with a gradient of 5–10% methanol in $CHCl_3$ to yield about 0.68 g of Compound 35.

Diethyl N-[4-[N-](2,4-diaminofuro[2,3-d]pyrimidin-5-yl)methyl(amino)methyl(benzoyl)-L-glutamate (37)

About 0.28 g of anhydrous $K_2CO_3$ and about 0.67 g of Compound 35 were added to a solution containing about 0.2 g of Compound 35 in about 3 ml anhydrous DMSO. The reaction mixture was stirred under nitrogen at room temperature for 24 hours. The temperature was then raised to about 45° C. and the reaction continued for an additional 48 hours. The reaction mixture was then cooled to room temperature, diluted with about 50 ml water and stirred for about 8 hours. The solid that separated was filtered, washed with water, air dried, and dissolved in methanol. About 1 g of silica gel was added to the solution and the suspension evaporated to dryness under reduced pressure. The silica plug was loaded on a dry silica gel column (2.4×17 cm) and eluted with a gradient of 1–7% methanol in $CHCl_3$. Fractions corresponding to the product were pooled and evaporated to dryness. The residue was triturated with cold anhydrous ether to yield about 0.25 g of Compound 37.

N-[4-[[N-](2,4-diaminofuro[2,3-d]pyrimidin-5-yl)methyl]amino]methyl]benzoyl]-L-glutamic acid (34)

About 1 ml of 1N sodium hydroxide was added to a solution containing about 0.1 g of Compound 37 in about 10 ml of 2:1 methanol/THF. The mixture was stirred at room temperature for about 24 hours. The volatiles were removed under reduced pressure, and the residue dissolved in about 5 ml water and stirred for an additional 24 hours. The solution was cooled in an ice bath and the pH adjusted carefully to 4.0 by dropwise addition of 1N HCl. The precipitate was collected by filtration, washed well with water and ether, and immediately dried under high vacuum to yield about 0.08 g of Compound 34.

Example 13

Compounds 33 and 34 were evaluated as inhibitors of *Lactobacillus casei* DHFR, human recombinant (REC) DHFR and DHFR isolated from human CCRF-CEM leukemic cells. The performance of these compounds was compared with that of MTX. The compounds were also evaluated as inhibitors of *L. casei* TS and human recombinant TS. The results are presented in Table 17 below.

TABLE 17

Inhibitory Concentrations ($IC_{50}$ in $\mu M$)

| Compound | Human REC DHFR | L. casei DHFR | CCRF-CEM DHFR | Human REC TS | L. casei TS |
|---|---|---|---|---|---|
| 33 | 1.0 | 0.1 | 0.25 | 220 | 200 |
| 34 | >200 | >200 | 30.5 | 63.0 | >200 |
| MTX | 0.004 | 0.006 | 0.0007 | 170 | ND |

Example 14

Compounds 33 and 34 were also evaluated for their substrate activity in CCRF-CEM human leukemia folylpolyglutamate synthetase; the compounds were compared against aminopterin. Results are presented in Table 18 below.

TABLE 18

Substrate Activity of Compounds 33 and 34 for CCRF-CEM Human Leukemia Cell Folylpolyglutamate Synthetase

| Substrate | $K_m$, $\mu M$ | $V_{max(rel)}$ | $V_{max}/K_{m(rel)}$ |
|---|---|---|---|
| Aminopterin | 4.8 ± 0.7 (N = 6) | 1 (N = 6) | 0.21 ± 0.04 (N = 6) |
| 33 | 8.5 ± 2.1 (N = 3) | 0.65 ± 0.01 (N = 3) | 0.07 ± 0.02 (N = 3) |
| 34 | ND | 0.6 (N = 5) | ND |

Example 15

Compounds 33 and 34 were also tested for their growth inhibition of human T-lymphoblastic leukemia cell line CCRF-CEM, its MTX-resistance subline (R30dm), and human squamous cell carcinoma cell lines (FaDu and A235). The performance of these compounds was evaluated against MTX. Results are presented in Table 19 below.

TABLE 19

Growth Inhibition ($EC_{50}$, $\mu M$) During Continuous Exposure (0 to 120 hours)

| Compound | CCRF-CEM | R30DM | FaDu | A253 |
|---|---|---|---|---|
| 33 | 0.29 ± 0.01 (N = 3) | 4.25 ± 0.05 (N = 2) | 0.018 ± 0.02 (N = 2) | 0.54 ± 0.09 (N = 3) |
| 34 | 48.0 ± 23.0 (N = 2) | ND | ND | ND |
| MTX | 0.014 ± 0.001 (N = 10) | 0.018 ± 0.003 (N = 5) | 0.017 ± 0.002 (N = 5) | 0.013 ± 0.0008 (N = 3) |

Average values are presented ± range for N=2 and ± standard deviation for N≧3.

Example 16

The following example provides methods for preparing the pyrido[2,3-d]pyrimidine compounds and pharmaceutically acceptable salts thereof as described above. Reference letters and numerals correspond with those in FIG. 13. Guanidine (FIG. 13b) is condensed with 2-amino-3,5-dicarbonitrile-4-$R_{13}$-pyridine (FIG. 13a), wherein $R_{13}$ is a lower alkyl group having one to about seven carbon atoms as described herein, in refluxing ethyl alcohol to produce 2,4-diaminopyrido[2,3-d]pyrimidine-5-$R_3$-6-carbonitrile (FIG. 13c). This product, 2,4-diaminopyrido[2,3-d]pyrimidine-5-$R_3$-6-carbonitrile (FIG. 13c), is then subjected to reductive condensation with an alkyl amine, a substituted aniline or benzylamine derivative containing the $R_2$ group as described herein, such as for example, 3,4,5-trimethoxyaniline, and Raney nickel in aqueous acetic acid solution, and preferably about 70% acetic acid solution, to form 2,4-diamino-5-$R_{13}$-6-[[($R_2$)amino]methyl]pyrido[2,3-d]pyrimidine (FIG. 13d). The starting material 2-amino-3,5-dicarbonitrile-4-$R_3$-pyrimidine (FIG. 13a) may be synthesized by those skilled in the art by modifying the method of Piper, et al., *J. Med. Chem.*, Vol. 29, p. 1080 (1986).

These methods further include adding the product represented in FIG. 13d to about 37% formaldehyde in acetonitrile at about 25° C., adding sodium cyanoborohydride, glacial acetic acid and methanol, and refrigerating the reaction mixture overnight to form 2,4-diamino-5-$R_{13}$-6[[($R_2$)methylamino]methyl]pyrido[2,3-d]pyrimidine (FIG. 13e).

2,4-Diamino-5-$R_3$-6[[($R_2$)formylamino]methyl]pyrido[2,3-d]pyrimidine (FIG. 13f) is prepared by reacting the product of FIG. 13d in about 98% formic acid as a solvent and acetic anhydride as a catalyst, removing the solvent under reduced pressure, diluting the reaction product with methanol and refrigerating the diluted reaction product overnight.

2,4-Diamino-5-$R_3$-6[[($R_2$)nitrosoamino]methyl]pyrido[2,3-d]pyrimidine (FIG. 13g) is prepared by reacting a chilled solution of the product of FIG. 13d in aqueous acetic acid and dimethyl formamide (DMF) and then adding $NaNO_2$ (sodium nitrate) in water. This mixture is stirred at about 0° C. to 5° C. for about two hours and then poured into dilute-sodium hydroxide.

It will be appreciated by those skilled in the art that by following the hereinbefore described methods of preparing the products of FIGS. 13d, 13e, 13f and 13g of this invention that the derivatives of the products of FIGS. 13d, 13e, 13f and 13g can be similarly prepared using the appropriate alkylamine, substituted aniline or benzylamine derivative containing the $R_2$ group as described herein.

Further, a method for preparing 4-amino-4-oxo derivatives of the products of FIGS. 13d, 13e, 13f or 13g of this invention includes subjecting these products to hydrolysis with 6N (six-normal solution) HCl for about six hours at room temperature.

Another embodiment of this invention is a method for preparing 2,4-dioxo derivatives of the products of FIGS. 13d, 13e, 13f or 13g that includes subjecting these products to hydrolysis with 6N HCl under mild reflux conditions for about two hours.

Example 17

The following example provides a method for preparing 6-(thiophenylmethyl)-2,4-diaminopyrido[2,3-d]pyrimidine (FIG. 14e) and 6-(thionapthylmethyl)-2,4-diaminopyrido[2,3-d]pyrimidine (FIG. 14f) generally represented by formula 11. Reference letters and numerals correspond with those in FIG. 14.

2,4-diaminopyrido[2,3-d]pyrimidine-6-carboxyaldehyde (FIG. 14b)

About 2.0 g of the nitrile (FIG. 14a) was dissolved in about 60 ml warm $HCO_2H$ under $N_2$. About 10 g of damp Raney Ni was added. The mixture was refluxed for 2 hours and filtered through Celite®. The filtrate was concentrated under reduced pressure at a temperature of 50° C. with the aid of EtOH. The resulting viscous orange residue was then dissolved in about 150 ml of boiling $H_2O$. The boiling solution was treated with Norit® and filtered through Celite® while hot. The filtrate was neutralized to pH 7 with 1N NaOH to give a yellow precipitate. The suspension was refrigerated overnight, filtered and washed with $H_2O$, EtOH and $Et_2O$ to yield about 1.75 g of a yellow solid. Examination by TLC (4:1:0.1 $CHCl_3$:MeOH:$NH_4OH$) showed a dominant UV-absorbing spot at $R_f$=0.38 and contamination spots at $R_f$=0.19 and at baseline. The spot at $R_f$=0.19 was, after chromatographic separation, determined to correspond to the $R_f$ value of compound (FIG. 14c).

2,4-diaminopyrido[2,3-d]pyrimidine-6-methanol (FIG. 14c)

About 5.0 g of crude aldehyde (FIG. 14b) was pulverized, dried and stirred in anhydrous MeOH under $N_2$ overnight. About 0.17 g of $NaBH_4$ was added to the mixture four times at intervals of 15 minutes. The mixture was stirred for 5 additional hours. Insoluble material was filtered and the filtrate was treated with about 200 ml $H_2O$. The filtrate was then concentrated under reduced pressure at a temperature of 35° C. until a yellow precipitate began to form. The mixture was then refrigerated overnight, filtered and rinsed with $H_2O$, EtOH and $Et_2O$ to yield about 1.50 g of a yellow solid. TLC (4:1:0.1 $CHCL_3$:MeOH:$NH_4OH$) showed a product spot at $R_f$=0.41 and a slight spot corresponding to the starting material. Separation was carried out by chromatography with silica gel.

6-(Bromomethyl)-2,4-diaminopyrido[2,3-d]pyrimidine (FIG. 14d)

About 0.24 g of crude alcohol (FIG. 14c) was dried with $P_2O_5$ at 110° C. under vacuum overnight and then added to about 10 ml of anhydrous dioxane. The mixture was stirred in an ice bath while dry HBr gas was bubbled through for 15 minutes, after which the flask was quickly stoppered. The mixture continued to stir and the alcohol dissolved after approximately ½ hour. The solution stirred for 24 hours and was then added dropwise to stirred $Et_2O$ under $N_2$ to give a yellow suspension. The suspension was refrigerated overnight, filtered and immediately dried with $P2O_5$ under vacuum at 50° C. to yield about 45 mg of the compound represented by FIG. 14d.

6-(Thiophenylmethyl-2,4-diaminopyrido[2,3-d] pyrimidine (FIG. 14e)

About 0.12 ml of phenylthiol was dissolved in about 10 ml DMAC and added dropwise to about 0.25 g of the compound of FIG. 14d. About 1 g of $K_2CO_3$ was added to the mixture to adjust the pH to approximately 8. After 1 hour, the compound of FIG. 14d was not detectable by TLC (3:1:0.1 $CHCl_3$:MeOH:$NH_4OH$). A product spot appeared at $R_f$=0.33 with contamination spots at $R_f$=0.51 and at baseline. The solid was filtered and rinsed with $H_2O$, EtOH and $Et_2O$ to yield about 22 mg of the compound of FIG. 14e.

6-(Thionaphthylmethyl)-2,4-diaminopyrido[2,3-d] pyrimidine (FIG. 14f)

About 0.07 g of napthylenethiol was dissolved in DMAC (15 mL) and added dropwise to about 0.10 g of the compound of FIG. 14d. About 0.3 g of $Na_2CO_3$ was added and the color of the reaction mixture changed from yellow to green. The reaction was monitored by TLC (4:1:0.1 $CHCl_3$:MeOH:$NH_4OH$). A product spot occurred at $R_f$=0.5. After 3 hours, starting material was still present. Also, the yellow color returned. The reaction was run overnight. The pH was then checked and found to be slightly acidic. The solution was added dropwise to about 100 ml of 1N $Na_2CO_3$. The suspension was stirred for 15 minutes and refrigerated for 4 hours. The solid was filtered and rinsed with $H_2O$, EtOH and $Et_2O$ to yield about 25 mg of the compound of FIG. 14f.

Example 18

The following are various methods for making various 2,4-diamino-6-substituted-benzylamino pyrido[2,3-d] pyrimidines generally represented by formula 11. Reference letters and numerals correspond with those in FIG. 15. The synthesis of the desired compounds is achieved via the reductive amination of 2,4-diamino-6 amino pyrido[2,3-d] pyrimidine 2, with the appropriately substituted aldehyde as generally illustrated in FIG. 15.

2,4-diamino-6-nitropyrido[2,3-d]pyrimidine (FIG. 15a)

About 1 equivalent of 2,4,6-triamino pyrimidine was suspended in about 50 ml of refluxing absolute ethanol with stirring under an atmosphere of nitrogen. Concentrated HCl was added dropwise to effect solution and as soon as solution occurred, about 1.2 equivalents of nitromalonaldehyde was added all at once. Within 10 minutes, a thick reddish voluminous precipitate started forming. TLC analysis indicated the presence of a yellow spot corresponding to that of the desired product along with staring materials. The reaction mixture was stirred at reflux for 3.5 hours, immediately diluted with 30 ml of water, cooled and neutralized with concentrated $NH_4OH$. The precipitate was collected on a funnel and was washed repeatedly with water to remove unreacted triamino pyrimidine to yield pure 2,4-diamino-6-nitropyrido[2,3-d]pyrimidine.

Example 19

Figure 16A:
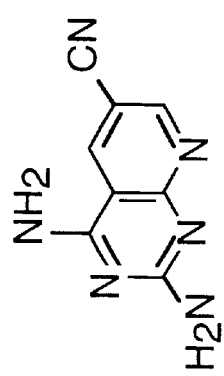
FIG. 16 shows a schematic diagram of the methods of preparing 2,4-diamino-6-(anilinomethyl)pyrido[2,3-d]pyrimidines.

The following is a method of making 2,4-diamino-6-(anilinomethyl)pyrido[2,3-d]pyrimidines generally represented by formula 11. Reference letters and numerals correspond with those in FIG. 16.

Figure 16B:
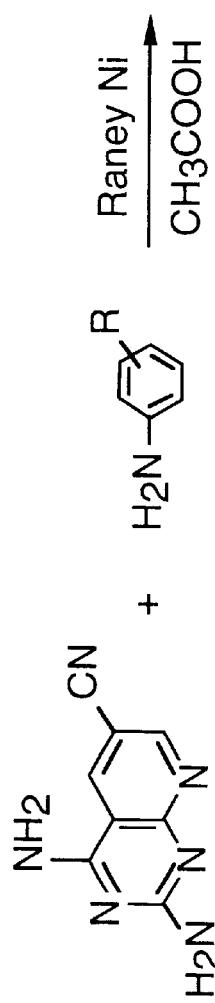
Figure 16C:
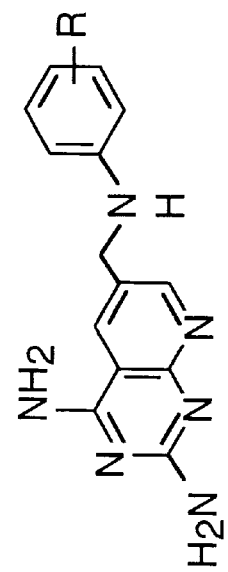

About 1 equivalent of 2,4-diamino-pyrido[2,3pyrimidine-6-carbonitrile (FIG. 16a) (achieved via literature procedures) was dissolved in 80% acetic acid. To this solution was added about 5 equivalents of Raney Nickel followed immediately by about 1.5 equivalents of the appropriately substituted aniline (FIG. 16b). The mixture was hydrogenated under atmospheric pressure and at room temperature for 6 hours. TLC analysis at the end of this period indicated the presence of a spot corresponding to the desired product. The reaction mixture was filtered through Celite® and the filtrate was evaporated to dryness to yield a reddish residue. This residue was dissolved in warm absolute ethanol and then neutralized in the cold with 1N $Na_2CO_3$ dropwise with stirring to deposit the crude product. This solid was collected by filtration and was washed repeatedly with acetone and dissolved in a large volume of methanol; silica gel was added and the methanol stripped off to yield a dry plug. Column chromatography using $CHCl_3$:MeOH (5:1) as the eluant yielded pure target compounds represented by FIG. 16c.

Example 20

The following example provides methods for making pyrido[3,2-d]pyrimidine compounds generally represented by formula 11. Reference letters and numerals correspond with those of FIG. 17.

2,4-dioxo-6-methylpyrido[3,2-d]pyrimidine (FIG. 17a)

About 20 g of 5-aminouracil, 80 ml of 20% HCl and 4 ml of crotonaldehyde were heated together under reflux for 1 hour. The solution was evaporated to dryness under rotary evaporation. Water was added to the residue so as to make the mixture just stirrable and then it was triturated with ammonium hydroxide with strong stirring until the pH increased to 10–11. Stirring was continued for another 10 minutes. The precipitate was filtered and was washed with minimal methanol and then chloroform and dried to yield about 17.58 g of the compound of FIG. 17a.

6-(Acetoxymethyl)-2,4-dioxopyrido-3,2-d] pyrimidine (FIG. 17b)

About 1.77 g of the compound of FIG. 17a in 50 ml of glacial acetic acid containing about 6.5 g of MCPBA (57–85%) was refluxed for 3 hours. About 40 ml of acetic anhydride was added to the hot reaction mixture and the refluxing was continued for another 30 minutes. The clear brown solution was evaporated to dryness and the solid was stirred with about 100 ml ether and filtered. The solid was crystallized from ethanol to yield about 1.55 g of the compound of FIG. 17b.

6-(Acetoxmethyl)-2,4-dichloropyrido[3,2-d] pyrimidine (FIG. 17c)

About 1.5 g of the compound of FIG. 17c was refluxed with about 38 ml of phosphoryl chloride containing about 2.5 ml of triethylamine for 8 hours. The volume was reduced to about 5 ml by rotary evaporation. The dark syrup which resulted was poured into crushed ice. The cold suspension was extracted with methylene chloride (3×50 ml) and washed with cold water until the washing were neutral. The organic layer was dried over anhydrous sodium sulfate and evaporated to dryness under rotary evaporation. The dark solid residue was stirred and refluxed with petroleum ether (30–60° C.) and a suitable amount of decoloring charcoal, and filtered through Celite®, which was repeated twice. The combined liquid solution was concentrated until the light yellow solid precipitated out and was allowed to cool to room temperature and stored in a refrigerator for 2 hours. The crystallized solid was filtered and dried to yield about 0.86 g of the compound of FIG. 17c.

2,4-diamino-6-(hydroxymethyl)pyrido[3,2-d] pyrimidine (FIG. 17d)

About 2.5 g of the compound of FIG. 17c was heated with 30 ml of liquid ammonia in a sealed bomb at between about 150–170° C. for 18 hours. After cooling to room temperature, the bomb was opened and the liquid ammonia was allowed to evaporate at room temperature. The solid was crystallized from glacial acetic acid and a small amount of water to yield about 1.24 g of the compound of FIG. 17d.

2,4-diamino-6-(bromomethyl)pyrido[3,2-d] pyrimidine (FIG. 17e)

A suspension of about 0.72 g of the compound of FIG. 17d in 12 mL dry THF was stirred for 8 hours with 1 ml of phosphorus tribromide. The precipitated solid was filtered, washed with cold 50% THF-Ether, and dried to give the compound of FIG. 17e. Because of the instability, this compound was not purified further. The ¹HNMR showed that the majority of the solid was the desired compound.

2,4-diamino-6-(paramethoxyanilinylmethyl)pyrido[3,2-d]pyrimidine (FIG. 17f)

To a suspension of about 3.5 mmol of the compound of FIG. 17e in anhydrous dimethylacetamide was added 0.92 g anisidine and 1.03 g anhydrous potassium. After the suspension was stirred for 2 days, almost all of the compound of FIG. 17e disappeared. The solvent DMAC was removed under diminished pressure. The solid residue was washed with methanol three times and filtered. To the combined liquid was added silica gel and the methanol was evaporated to dryness. Separation to afford pure product of FIG. 17f was carried out by column chromatography.

2,4-diamino-6-(phenylthiomethyl)pyrido[3,2-d]pyrimidine (FIG. 17g)

To a suspension of about 2.5 mmol of the compound of FIG. 17g in anhydrous dimethylacetamide was added 1 mL thiophenol and 690 mg anhydrous potassium. The suspension was stirred for 3 days. The solvent DMAC was removed under diminished pressure. The solid residue was washed with methanol three times and filtered. The combined liquid was added to silica gel and then the methanol was evaporated to dryness. A small amount of product was separated through a dry column. After crystallization, about 5 mg of pure product of FIG. 17g was obtained.

2,4-diamino-6-(naphathalinylmethyl)pyrido[3,2-d]pyrimidine (FIG. 17h)

The procedure for making the compound of FIG. 17f was repeated with a reaction time of 5 days to yield the compound of FIG. 17h.

Example 21

The following example provides methods for making the tricyclic pyrimidine compounds generally represented by formula 10. Reference letters and numerals correspond with those of FIG. 10.

N-butoxycarbonyl-4-piperidine (FIG. 10b)

About 2 g of 4-piperidine hydrochloride monohydrate (FIG. 10a) was dissolved in about 30 ml of N,N-dimethylformamide at temperatures of between about 110–115° C. The solution was cooled to room temperature, and to this solution was added about 2.6 g of triethyl amine and a solution containing about 3.06 g of ditertiarybutyl decarbonate in 10 ml DMF. The reaction was continued for about 24 hours at room temperature. The DMF was removed under reduced pressure. About 100 ml of water was added to the residue and the mixture was extracted with ethyl ether (2×100 ml), and the organic layer dried over anhydrous MgSO$_4$. The ether was evaporated to dryness under reduced pressure to yield about 2.33 g of the compound of FIG. 10b.

3-bromo-4-piperidine hydrobromide (FIG. 10c)

About 2.6 g of N-butoxycarbonyl-4-piperdone (FIG. 10b) was dissolved in about 70 ml of chloroform; to this solution was added about 2.08 g Br$_2$ over a period of about 30 minutes. The reaction was continued for about 2 hours at room temperature during which a white precipitate of the compound of FIG. 10c was formed. The reaction mixture was filtered and washed with chloroform ether to yield about 2.76 g of the compound of FIG. 10c.

2,4-diamino-5,6,7,8-tetrahydro-7-pyrido[4',3':4,5]furo[2,3-d]pyrimidine hydrobromide (FIG. 10f)

A solution containing about 1.83 g of the compound of FIG. 10c in about 10 ml of anhydrous DMF was added dropwise to a suspension containing about 0.504 g of 2,4-diamino-6-hydroxypyrimidine in about 3 ml of anhydrous DMF. The reaction became a clear solution after about 1 hour; the solution was then left at room temperature for about 48 hours. The white precipitate which formed was collected by filtration and air dried to yield about 0.66 g of the compound of FIG. 10f.

2,4-diamino-5,6,7,8-tetrahydro-(7-butoxycarbonyl)pyrido[4',3',5':4,5]furo[2,3-d]pyrimidine hydrobromide (FIG. 10e)

The filtrate obtained in preparing the compound of FIG. 10c was diluted with about 150 ml of chloroform and washed with water, saturated sodium bicarbonate and brine. The organic layer was dried over anhydrous MgSO$_4$, and the chloroform was removed under reduced pressure to yield a viscous brown oil. The residue was dissolved immediately in about 5 ml of anhydrous DMF, and added to a suspension containing about 0.252 g of 2,4diamino-6-hydroxypyrimidine in anhydrous DMF. The reaction was continued for about 48 hours at room temperature. The DMF was removed under reduced pressure, and the residue was dissolved in 50 ml of methanol; about 1.7 g of silica gel was added and the mixture was evaporated to dryness under reduced pressure. About 50 ml of ether was added to the silica gel plug; the homogenous plug collected after filtration was air-dried and then placed on top of a dry silica gel column (1.5 cm×10 cm) and gradiantly eluted with MeOH in CHCl$_3$. Fractions containing the compound of FIG. 10e were pooled and evaporated to dryness under reduced pressure to yield 0.025 g of the compound.

2,4-diamino-5,6,7,8-tetrahydro-7-(benzyl)pyrido[4',3':4,5]furo[2,3-d]pyrimidine (FIG. 10g)

About 0.46 g of the compound of FIG. 10f was suspended in 5 ml of anhydrous DMSO. About 0.483 g of anhydrous potassium carbonate and 0.24 g of benzyl bromide were added to the suspension; the reaction was continued for 24 hours at room temperature. The mixture was then diluted with about 30 ml of water and stirred for 24 hours at room temperature. The resulting precipitate was collected by filtration, washed with water, acetone, ether and air-dried. The crude solid was dissolved in a mixture of DMF:MeOH (1:5); about 1.2 g of silica gel was added and the mixture was evaporated to dryness under reduced pressure. The resulting silica gel plug was placed on a top of a dry silica gel column (1.5 cm×10 cm) and gradiantly eluted with MeOH in CHCl$_3$. The fractions containing the compound of FIG. 10g were pooled and evaporated to dryness under reduced pressure; the resulting solid was triturated with ether and filtered to yield about 0.156 g of product.

2,4-diamino-5,6,7,8-tetrahydro-7-[(3',4',5'-trimethoxy)benzyl]pyrido[4',3':4,5]furo[2,3-d]pyrimide (FIG. 10h)

The compound of FIG. 10h was prepared and purified in the same manner as the compound of FIG. 10g, only using 3',4',5'-trimethoxybenzyl chloride instead of benzyl bromide to yield about 0.12 g of the compound of FIG. 10h as a yellow solid.

2,4-diamino-5,6,7,8-tetrahydro-7-[(3',5'-dimethoxy)benzyl]pyrido[4',3':4,5]furo[2,3-d]pyrimide (FIG. 10i)

The compound of FIG. 10i was prepared and purified in the same manner as the compound of FIG. 10g, only using 3',5'-dimethoxybenzyl chloride instead of benzyl bromide to yield about 0.126 g of the compound of FIG. 10i.

2,4-diamino-5,6,7,8-tetrahydro-7-[(2',4'-dichloro) benzyl]pyrido[4',3':4,5]furo[2,3-d]pyrimide (FIG. 10j)

The compound of FIG. 10j was prepared and purified in the same manner as the compound of FIG. 10g, only using 2',4'-dichlorobenzyl chloride instead of benzyl bromide to yield about 0.151 g of the compound of FIG. 10j.

2,4-diamino-5,6,7,8-tetrahydro-7-[(3',4'-dichloro) benzyl]pyrido[4',3':4,5]furo[2,3-d]pyrimide (FIG. 10k)

The compound of FIG. 10k was prepared and purified in the same manner as the compound of FIG. 10g, only using 3',4'-dichlorobenzyl chloride instead of benzyl bromide to yield about 0.131 g of the compound of FIG. 10k.

2,4-diamino-5,6,7,8-tetrahydro-7-[(2',6'-dichloro) benzyl]pyrido[4',3':4,5]furo[2,3-d]pyrimide (FIG. 10l)

The compound of FIG. 10l was prepared and purified in the same manner as the compound of FIG. 10g, only using 2',6'-dichlorobenzyl chloride instead of benzyl bromide to yield about 0.093 g of the compound of FIG. 10l.

2,4-diamino-5,6,7,8-tetrahydro-7-[(2',4'-dichloro) benzyl]pyrido[4',3':4,5]furo[2,3-d]pyrimide (FIG. 10m)

2,4-diamino-5,6,7,8-tetrahydro-7-[(4"-benzoyl)diethyl-L-glutamic acid)]pyrido[4',3':4,5]furo[2,3-d]pyrimidine was prepared and purified in the same manner as the compound of FIG. 10g, only using 4'-(chloromethyl)benzoyl glutamic acid diethyl ester instead of benzyl bromide. About 1.5 ml of 1N NaOH was added to a solution containing about 0.183 g of this compound in 10 ml methoxyethanol, and the solution stirred at room temperature for about 24 hours. The ethoxyethanol was evaporated under reduced pressure, the residue was dissolved in about 10 ml of water and stirring continued for an additional 24 hours. The solution was cooled in an ice bath and the pH was adjusted to about 3.5 via dropwise addition of 1N HCl. The precipitate formed was collected by filtration, washed with water, acetone and ether and air-dried to obtain about 0.160 g of the compound of FIG. 10m.

Example 22

The compound of FIG. 10m was tested for DHFR inhibition, as discussed above in Example I, against *Pneumocystis carinii* (Pc), *Toxoplasmosis gondii* (Tg), *Macrobacterium avium* (Ma) and rat liver (RL). Ma is an opportunistic infection in HIV infected patients. Table 20 sets forth the $IC_{50}$ values.

TABLE 20

Inhibitory Concentrations ($IC_{50}$, microM) and Selectivity Ratios

| Compound | Pc | Tg | RL | RL/Pc | RL/Tg | M. avium |
|---|---|---|---|---|---|---|
| 10 m | 10.9 | 21.5 | 85.8 | 7.9 | 4 | 0.97 |

The compound of FIG. 10m showed a weak inhibitory activity against DHFR, but displayed promising selectivity ratios of 7.9 and 4 against Pc DHFR and Tg DHFR, respectively, against RL DHFR. In addition, compound 10m showed significant inhibitory activity against Ma DHFR and had a selectivity ratio of 88 versus RL DHFR.

In addition, the ability of the compound of FIG. 10m to function as a substrate of human CCRF-CEM folylpolyglutamate synthetase was assessed, as discussed above in EXAMPLE 4. Results are presented in Table 21.

TABLE 21

Activity of the Compound of FIG. 10 m as Substrate for CCRF-CEM Human Leukemia Cell Folylpolyglutamate Synthetase

| substrate | $K_m$, microM | $V_{max,rel}$ | $V_{max}/K_{m(rel)}$ | n |
|---|---|---|---|---|
| Aminopterin | 4.8 ± 0.7 | 1 | 0.21 ± 0.04 | 6 |
| 10 m | 6.2 ± 1.4 | 0.29 ± 0.05 | 0.06 ± 0.01 | 2 |

Example 23

The following example provides methods for making pyrido[3,2-d]pyrimidine compounds generally represented by formula 11. Reference letters and numerals correspond with those of FIG. 11.

Figure 11A:
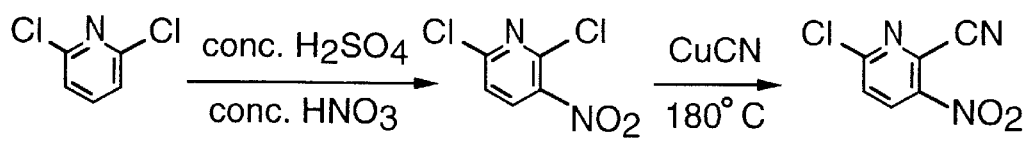
FIG. 11 shows a schematic diagram of the methods of preparing pyrido[3,2-d]pyrimidines.
Figures 11B, 11C:
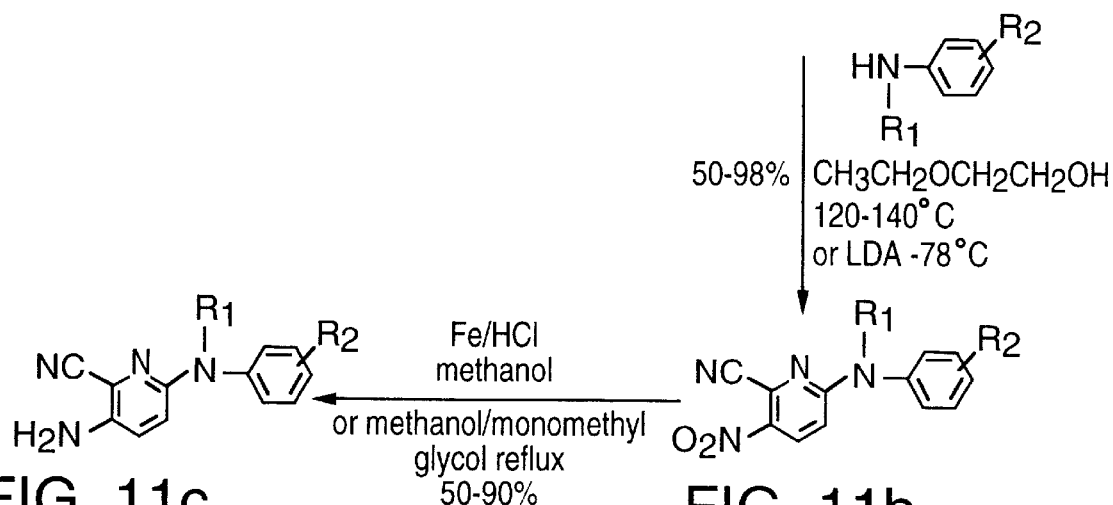
Figure 11D:
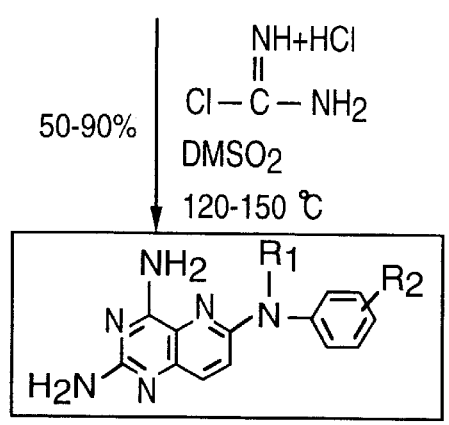

The compound of FIG. 11a was synthesized from 2,6-dichloropyridine in two steps—nitration at the 3 position with concentrated sulfuric acid and 90% nitric acid, followed by substitution of the 2-chloro moiety with a cyano group using CuCN at 180° C. The compound of FIG. 11b was synthesized via a direct aromatic substitution of FIG. 11a with arylamines, 3',4',5'-trimethoxybenzylamine, or N-methylarylamines in 2 ethoxyethanol at temperatures between about 120–140° C. The compound of FIG. 11b was then reduced by iron in acidic conditions under reflux in methanol to yield the intermediate 2-cyano-3-amino-6-substituted pyridines (FIG. 11c). Monomethylglycol was added to increase the solubility. The compound of FIG. 11c was condensed with formamidine hydrochloride in dimethyl sulfone at temperatures between about 120 and 150° C. to provide the compound of FIG. 11d.

Example 24

The following example provides methods for making pyrido[3,2-d]pyrimidine compounds generally represented by formula 11. Reference letters and numerals correspond with those of FIG. 12.

The compound of FIG. 12a was reduced with iron powder, followed by condensation with chlorohydrochloride in DMSO at temperatures of between about 120 and 150° C. to yield 2,4-diamino-6-chloro-pyrido[3,2-d]pyrimidine (FIG. 12c). The compound of FIG. 12c was subjected to a substitution reaction with substituted thiophenols, to yield three arylthiol compounds (FIGS. 12f, 12g, and 12h) generally represented by FIG. 12d. The oxidation of these compounds with hydrogen peroxide in acetic acid provided three corresponding sulfonyl compounds with the general structure represented by FIG. 12e.

Example 25

The following example provides methods for making pyrido[3,2-d]pyrimidine compounds generally represented by formula 11. Reference letters and numerals correspond with those of FIG. 18.

The compound of FIG. 18a was prepared from 2,6-dichloropyridine by methods known in the art. The 3-amino group of the compound of FIG. 18a was protected with an acetyl group by reacting the compound with acetyl anhydride and triethylamine in the presence of DMAP under reflux conditions in methylene chloride for 20 hours. Part of the starting material was converted to the N,N-diacetylated amino derivative, which was in turn converted in situ into the compound of FIG. 18b when stirred in a saturated sodium bicarbonate solution at room temperature for about 1.5 hours. The compound of FIG. 18b was then oxidized with trifluroperacetic acid in methylene chloride at room temperature for 24 hours to yield the compound of FIG. 18c, 2-amidylpyridine-N-oxide. The compound of FIG. 18c was then heated at about 140° C. with a guanidine carbonate base in 2-ethoxyethanol for about one hour to yield the compound of FIG. 18d, 6-chloro-2-methyl-4-oxo-pyrido[3,2-d]pyrimidine. The compound of FIG. 18d was then reacted with the sodium salt of p-thiocresol in anhydrous DMF at 125° C. to yield the pyrido[3,2-d]pyrimidine compound of FIG. 18e.

Any compatible sulfur, oxygen or nitrogen containing nucleophile can be reacted with the compound of FIG. 18d to yield the corresponding pyrido[3,2-d]pyrimidine compound.

Example 26

Figure 19:
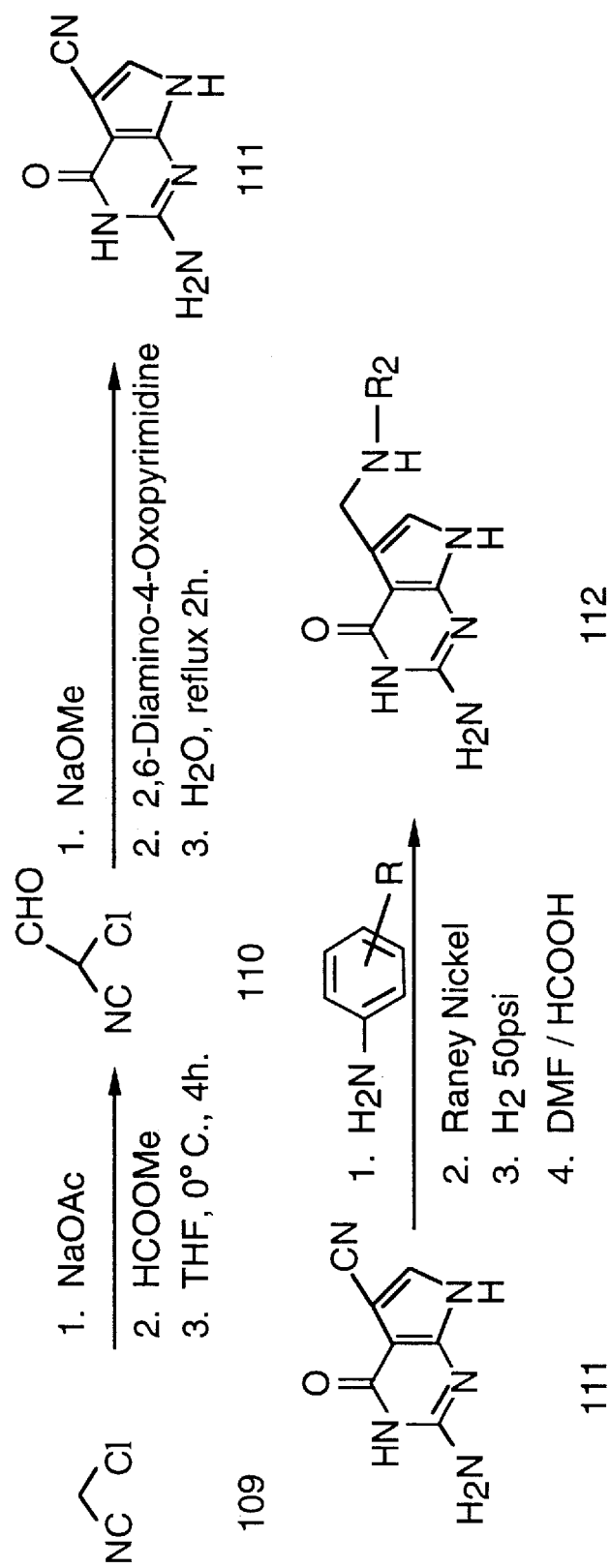
FIG. 19 shows a schematic diagram of the methods of preparing the compounds having formula 13.

Reference numerals correspond with those of FIG. 19.

A 2-amino-4-oxo-5-cyanopyrrolo[2,3-d]pyrimidine(III) was prepared according to the method reported by Migawa, et al., "A Two Step Synthesis of the Nucleoside q Precursor 2-amino-5-cyanopyrrolo[2-3-d pyrimidine-4-one" *Syn. Comm.* 26:3317(1996) which involved the synthesis of chloroformylacetonitrile (110) from chloroacetonitrile (109) and methyl formate as shown in FIG. 19. Cyclocondensation of compound 10 with 2,6-diamino-4-oxopyrimidine afforded to the key intermediate in 65–70% overall yield. Reductive amination of the 5-nitrile with the appropriate anilines or ethyl-p-aminobenzoyl-L-glutamate in the presence of Raney nickel and hydrogen at 50 psi for 5–6 hours afforded the desired analogues which were purified by column chromatography and were obtained in 20–62% yield. This yielded the product generally represented by compound 112. For the classical analogue, compound 407, which is the compound 112 where $R_2$ is p-benzoyl-L-glutamate, saponification of the chromatographically purified ester afforded the desired product. This method was used to synthesize compounds 407–415, which are generally represented by compound 112 in FIG. 19 with the following substitutions:

| Compound | $R_2$ |
|---|---|
| 407 | p-benzoyl-L-glutamate |
| 408 | 2,5-diOMe phenyl |
| 409 | 3,5-diOMe phenyl |
| 410 | 2,4-diOMe phenyl |
| 411 | 3,4,5-triOMe phenyl |
| 412 | 2,5-diCl phenyl |
| 413 | 3,5-diCl phenyl |
| 414 | 2,4-diCl phenyl |
| 415 | 3-Cl phenyl |

Example 27

Compounds 407–415, prepared as described in Example 26, were tested for inhibition of tgDHFR, pcDHFR, rlDHFR and *E-coli* thymidylate synthase (ecTS) according to the methods disclosed in Example 1. The performance of these compounds was measured against TMP. Results are presented in Table 22.

TABLE 22

Inhibitory Concentration ($IC_{50}$) of Nonclassical 5 In $\mu$M.

| Cpd. | $R_2$ | pcDHFR | rlDHFR | tgDHFR | rl/tg | ecTS |
|---|---|---|---|---|---|---|
| 408 | 2-5,diOMe phenyl | >47 | >47 | 2.2 | >21 | >160 (21%) |
| 409 | 3,5-diOMe phenyl | >20 | >20 | 2.6 | >8 | >160 (0%) |
| 410 | 2-4-diOMe phenyl | >16 | >16 | 7.1 | >1.4 | >160 (8%) |
| 411 | 3,4,5-triOMe phenyl | >22 | >22 | 6.9 | >3 | >290 (8%) |
| 412 | 2,5-diCl phenyl | >25 | >25 | 0.66 | >38 | ND |
| 413 | 3,5-diCl phenyl | 66.2 | >63 | 3 | >21 | ND |
| 414 | 2,4-diCl phenyl | >15 | >15 | 2.2 | >7 | ND |
| 415 | 3-Cl phenyl | >26 | >26 | 3.5 | >7 | >180 (26%) |
| TMP | — | 12.0 | 133.0 | 2.7 | 49.0 | — |

Results of testing of the classical analogue, compound 407, are shown in Table 23. As can be seen from Table 22, the nonclassical analogues, compounds 408–415, were micromolar inhibitors of tgDHFR with the 2,5-dichlorophenyl analogue being the most potent ($IC_{50}$=0.66 $\mu$M). All the analogues were poorly inhibitory against pcDHFR, rlDHFR and ecTS.

Compound 407 was a poor inhibitor of TS from *L. casei, E. coli, P. carinii* (46, >12, 5.8 $\mu$M respectively) and DHFR from *L. casei* and *E. coli* (6.9 and 23 $\mu$M respectively). The growth inhibitory potency of compound 407 was compared to that of methotrexate (MTX) in continuous exposure against CCRF-CEM human lymphoblastic leukemia and a series of MTX resistant sublines. Compound 407 was only 5-fold less potent than MTX against the parenteral cells. DHFR-overexpressing cells were 43-fold resistant to MTX, but only 2.5-fold resistant to compound 407, suggesting that DHFR is not the primary target of this agent. MTX transport-defective cells are 160-fold resistant to MTX, but <4-fold resistant to compound 407. This suggests either that the mutation decreasing the $V_{max}$ of MTX transport in this cell line does not affect compound 407 in a similar manner or that compound 407 primarily uses a separate transport pathway. Polyglutamation of tight-binding enzyme inhibitors, like MTX, is not required in continuous exposure; this accounts for the lack of resistance of polyglutamylation-defective R30dm to MTX. However, for inhibitors where polyglutamylation is required for potent target inhibition (for example ZD1694), resistance may become apparent for polyglutamylation-defective cell lines, even in continuous exposure. The weak cross-resistance of R30dm to compound 407 suggest either that the parent drug is a potent target inhibitor or that polyglutamylation of this drug is highly efficient.

TABLE 23

Growth Inhibition of CCRF-CEM Human Leukemia Cells And Its MTX-resistant Sublines By MTX and Compound 407

| Cell Line | Resistance Mechanism | EC50, nM | |
|---|---|---|---|
| CEM | sensitive | MTX | Compound 407 |
| | | 15 ± 0 (n = 3) | 79 ± (n = 3) |

TABLE 23-continued

Growth Inhibition of CCRF-CEM Human Leukemia Cells And Its MTX-resistant Sublines By MTX and Compound 407

| Cell Line | Resistance Mechanism | EC5O, nM | |
|---|---|---|---|
| R1 | ↑ DHFR | 6445 ± 55 (n = 2) | 200 ± 20 (n = 2) |
| R2 | ↓ transport | 2350 ± 550 (n = 2) | 310 ± 30 (n = 2) |
| R30 dm | ↑↑ FPGS | 16 ± 1 (n = 2) | 120 ± 10 (n = 2) |

Example 28

Figure 20:
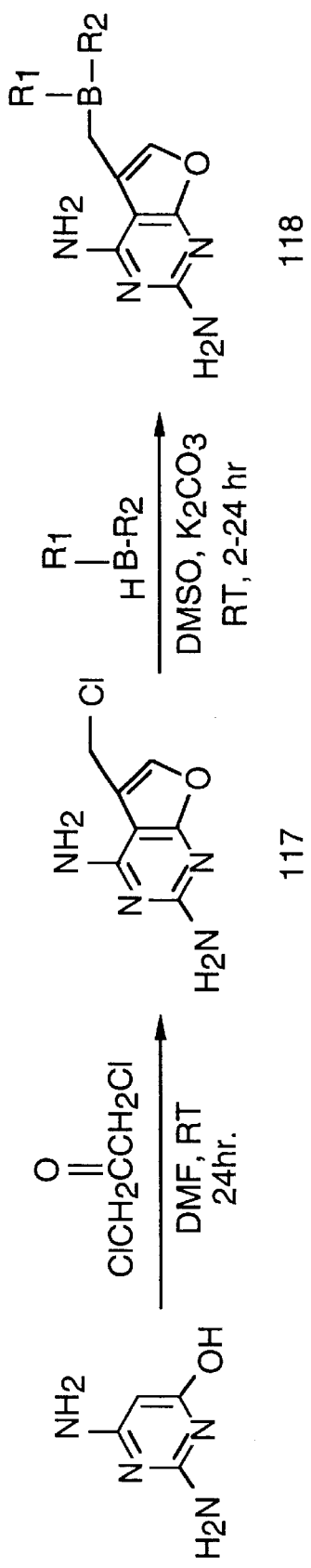
FIG. 20 shows a schematic diagram of the methods of preparing compounds having formula 13.

Reference numerals correspond with those in FIG. 20.

The syntheses of compounds 420–434 was carried out by a nucleophilic displacement of the key intermediate 2,4-diamino-5-chloromethylfuro[2,3-d]pyrimidine (117) with the appropriate thiol or aniline as shown in FIG. 20. The intermediate (117) was obtained from 2,6-diamino-4-hydrooxypyrimidine and dichloroacetone. Purified 117 afforded the target compounds in 16–39% yield. Chromatographic purification was necessary for the final compounds, which was carried out on silica gel using 3% MeOH in CHCl$_3$.

As can be seen from FIG. 20, the product of this method has the general formula of compound 4, as described throughout the specification. Referring to formula 4, in these particular compounds, X and Y are both NH$_2$, L and M are both carbon and the bond between L and M is a double bond, R4 is hydrogen, A is CH, R3 is H, and B, R1 and R2 are as illustrated below in Table 24.

TABLE 24

| Compound | B | R$_1$ | R$_2$ |
|---|---|---|---|
| 420 | S | — | phenyl |
| 421 | S | — | 1-naphthyl |
| 422 | S | — | 2-naphthyl |
| 423 | N | H | 1-naphthyl |
| 424 | N | H | 2-naphthyl |
| 425 | O | — | 2-naphthyl |
| 426 | N | H | 2-phenoxyphenyl |
| 427 | N | H | 4-phenoxyphenyl |
| 428 | N | H | 2-phenylphenyl |
| 429 | N | CH$_3$ | 2-naphthyl |
| 430 | N | H | 2,5-dichlorophenyl |
| 431 | N | CH$_3$ | 3,4-dichlorophenyl |
| 432 | N | CH$_3$ | 3,4,5-trichlorophenyl |
| 433 | N | H | 3-methoxyphenyl |
| 434 | N | CH$_3$ | 2,5-dimethoxyphenyl |

Compounds 420–434 were prepared from compound 118 as described below:

2-4-Diamino-5-[(phenylthio)methyl]furo[2,3-d]pyrimidine (420)

To a 100 ml three neck round bottom flask was added sequentially anhydrous DMSO (15 mL), thiophenol (0.85 g), crude 117 (0.75 g) and anhydrous potassium carbonate (1.03 g). The reaction mixture was stirred at room temperature for 2 h and then quenched with water (150 mL). The resultant suspension was stirred at room temperature for 10 h and filtered. The solid was extracted twice with MeOH (150 mL+100 mL) and the extracts were mixed with silica gel (2 g). The mixture was evaporated under reduced pressure and dried in vacuo. The residue was powered and poured on top of a dry column of silica gel (40 g). The column was washed with MeOH in CHCl$_3$. Fractions corresponding to a single spot (TLC) of the product were pooled and evaporated. The residue was washed with ether and air dried to afford 0.17 g (16% for two steps) of compound 420 as a light pinkish solid.

2,4-Diamino-5-[(1-naphthylthio)methyl]furo[2,3-d]pyrimidine (421)

To a 50 ml three neck round bottom flask was added sequentially anhydrous DMSO (8 ml), 1-naphthylthiol (0.89 g), compound 117 (0.63 g) and anhydrous potassium carbonate (0.92 g). The reaction mixture was stirred at room temperature for 2 h and then quenched with distilled water (16 ml). The resultant suspension was stirred at room temperature for 4 h, cooled to 5° C. and filtered. The solid was washed with cold water (2×5 ml) and then stirred in ether (20 ml) for 8 h. The suspension obtained was filtered and the residue dissolved in acetic acid (40 ml). The solution was mixed with charcoal (0.1 g) and stirred at 40° C. for 15 min. The mixture was filtered and the filtrate evaporated to dryness. The residue was washed thoroughly with MeOH to yield 0.44 g (29%) of compound 422 as a light yellow solid which was homogeneous on TLC.

2,4-Diamino-5-[(2-naphthylthio)methyl]furo[2,3-d]pyrimidine (422)

To a 50 ml three neck round bottom flask was added, in order, anhydrous DMSO (5 mL), 2-naphthalenethiol (1.12 g), crude 117 (1.39 g) and anhydrous potassium carbonate (0.97 g). The reaction mixture was stirred at room temperature for 2 h and then quenched with distilled water (50 ml). The resultant suspension was stirred at room temperature for 8 h, cooled to 5° C. and filtered. The solid was washed with cold water (2×5 ml) and then extracted several times with MeOH (100 ml). Extracts with a major spot of the product on TLC were pooled and mixed with silica gel (2 g). The mixture was evaporated under reduced pressure and then dried in vacuo. The residue was ground into a fine powder and poured on top of a dry column of silica gel (40 g). The column was washed with MeOH in CHCl$_3$: 200 ml (0.5%), 100 ml (1%), 100 ml (2%). The column was then eluted with 3% MeOH in CHCl$_3$. Fractions corresponding to a single spot were also pooled and evaporated. The residue was washed thoroughly with ether to afford an additional 0.05 g of the pure product. Fractions with a major spot of the product and a faint spot just below the product spot were also pooled and evaporated. The residue was washed thoroughly with MeOH to afford an additional 0.06 g of the pure product (combined yield 10% for two steps) compound 422 as a light pinkish solid.

2,4-Diamino-5-[(1-naphthylamino)methyl]furo[2,3-d]pyrimidine (423)

To a 50 ml three neck round bottom flask was added sequentially anhydrous DMSO (5 ml), 1-aminonaphthalene (0.66 g), Compound 117 (0.50 g) and anhydrous potassium carbonate (0.69 g). The reaction mixture was stirred at 50° C. for 8 h under nitrogen in the dark. The reaction was then quenched with distilled water (15 ml) and the resultant suspension stirred at room temperature for 4 h, cooled to 5° C. and filtered. The residue was washed with cold water (2×5 ml) and then dissolved in hot MeOH, and the solution mixed with silica gel (2 g). The mixture was evaporated under reduced pressure and then dried in vacuo. The residue was ground into a fine powder and poured on top of a dry column of silica gel (40 g). The column was washed with MeOH in CHCl$_3$: 200 ml (0.5%), 100 ml (1%), 100 ml (2%).

The column then eluted with 3% MeOH in CHCl$_3$. Fractions corresponding to a single spot of the product (TLC) were pooled and evaporated. The residue was washed with ether and air dried to afford 0.25 g (33%) of compound 423 as a light yellow solid.

2,4-Diamino-5-[(2-naphthylamino)methyl]furo[2,3-d]pyrimidine (424)

To a 50 ml three neck round bottom flask was added, in sequence, anhydrous DMSO (4 mL) 2-aminonaphthalene (0.54 g), compound 117 (0.61 g) and anhydrous potassium carbonate (0.55 g). The reaction mixture was stirred at 45° C. for 8 h under nitrogen in the dark and then quenched with distilled water (12 ml). The resultant suspension was stirred at room temperature for 4 h, cooled to 5° C. and filtered. The solid was washed with cold water (2×5 ml) and then dissolved in hot MeOH. The solution was then mixed with silica gel (2 g) and the mixture evaporated under reduced pressure and then dried in vacuo. The residue was ground into a fine powder and poured on top of a dry column of silica gel (40 g). The column was washed with MeOH in CHCl$_3$: 200 ml (0.5%), 100 ml (1%), 100 ml (2%). The column was then eluted with 3% MeOH in CHCl$_3$. Fractions corresponding to a single spot of the product (TLC) were pooled and evaporated. The residue was washed with ether and air dried to afford 0.27 g (29%) of compound 424 as a white solid.

2,4-Diamino-5-[(2-naphthoxy)methyl]furo[2,3-d]pyrimidine (425)

To a 50 ml three neck round bottom flask was added in sequence anhydrous DMSO (4 ml), 2-naphthol (0.27 g), compound 117 (0.25 g) and anhydrous potassium carbonate (0.26 g). The reaction mixture was stirred at 45° C. for 24 h under nitrogen in the dark and then quenched with distilled water (12 ml). The resultant suspension was stirred at room temperature for 4 h, cooled to 5° C. and filtered. The sold was washed with cold water (2×5 ml) and then dissolved in MeOH. The solution was mixed with silica gel (1 g) and the mixture was evaporated under reduced pressure and dried in vacuo. The residue was ground into a fine powder and poured on top of a wet column of silica gel (30 g) and eluted with 3% MeOH in CHCl$_3$. Fractions corresponding to a single spot of the product (TLC) were pooled and evaporated to afford 0.09 g compound 425 (23%) as a white solid.

2,4-Diamino-5-[(2'-phenoxyanilino)methyl]furo[2,3-d]pyrimidine (426)

To a 50 ml three neck round bottom flask was added in order anhydrous DMSO (4 ml), 2-phenoxyaniline (0.35 g), compound 117 (0.25 g) and anhydrous potassium carbonate (0.21 g). The reaction mixture was stirred at 45° C. for 8 h under nitrogen in the dark and then quenched with distilled water (12 ml). The resultant suspension was stirred at room temperature for 4 h, cooled to 5° C. and filtered. The solid was washed with cold water (2×5 ml) and then dissolved in MeOH. The solution was mixed with silica gel (1 g). The mixture was evaporated under reduced pressure and dried in vacuo. The residue was ground into a fine powder and poured on top of a wet column of silica gel (30 g) and eluted with 3% MeOH in CHCl$_3$. Fractions corresponding to a single spot (TLC) of the product were pooled and evaporated. The residue was washed with ether and dried to afford 1.16 g (37%) of compound 426 as a white solid.

2,4-Diamino-5-[(4'-phenoxyanilino)methyl]furo[2,3-d]pyrimidine (427)

Using a similar method to that for compound 426, 0.06 g of chromatographically pure compound 427 was obtained as a white solid. Fractions corresponding to a major spot of the product (TLC) and a spot of some unknown impurity just below were pooled and evaporated. The residue was washed with MeOH to afford an additional 0.12 g of the product which was homogeneous on TLC.

2,4-Diamino-5-[(2'-phenylanilino)methyl]furo[2,3-d]pyrimidine (428)

To a 50 ml three neck round bottom flask with compound 117 (0.30 g), 2-aminobiphenyl (0.38 g) and K$_2$CO$_3$ (0.25 g) was added anhydrous DMSO (3 ml) and the reaction mixture stirred for 8 h at 45° C. under nitrogen in the dark. Distilled water (10 ml) was added to precipitate the product and the suspension was stirred for 2 h, cooled to 5° C. and filtered. The solid was washed with cold water (2×2 ml) and suspended in MeOH (200 ml). Silica gel (1 g) was added and the suspension sonicated and heated to 50° C. for 15 min, evaporated under reduced pressure and dried in vacuo for 10 h. The residue was powdered and poured on top of a wet column of silica gel (30 g) and eluted with 3% MeOH in CHCl$_3$. Fractions corresponding to the product spot (TLC) were pooled and evaporated. The residue was washed with ether and air dried to afford 0.24 g (48%) of compound 428 as a light yellow solid. Recrystallization from MeOH afforded the analytically pure compound 428.

2,4-Diamino-5-[(N-methyl-2-naphthylamino)methyl]furo[2,3-d]pyrimidine (429)

To a suspension of compound 424 (0.10 g, 0.32 mmol), 30% (w/w) aqueous solution of formaldehyde (0.1 ml) and NaCN BH$_3$ (0.063 g) in acetonitrile (10 ml) was added dropwise concentrated hydrochloric acid until the suspension dissolved. The solution was stirred at room temperature for 1 h. The solvent was evaporated under reduced pressure and the residue dissolved in a minimum amount of distilled water and the pH of the solution adjusted to 7 with concentrated NH$_4$OH. The resulting suspension was sonicated, cooled to 5° C. and filtered. The residue was washed with cold water (2×3 ml), stirred in MeOH (5 ml) for 12 h and filtered. The residue was washed with MeOH (2×3 ml) to afford 0.065 g (64%) of compound 429 as a light yellow solid.

2,4-Diamino-5-[(2',5'-dichloroanilino)methyl]furo[2,3-d]pyrimidine (430)

To a 100 ml three neck round bottom flask was added, in sequence, anhydrous DMSO (30 ml), 2,5-dichloroaniline (2.43 g), crude compound 117 (1.49 g) and anhydrous potassium carbonate (2.07 g). The reaction mixture was stirred at 45° C. for 8 h and then quenched with distilled water (150 ml). The resultant suspension was stirred at room temperature for 8 h and filtered. The solid was extracted with MeOH (100 mL) several times and extracts which gave a major spot of the product on TLC were pooled and mixed with silica gel (2 g) and the mixture evaporated under reduced pressure and then dried in vacuo. The residue was ground into a fine powder and poured on top of a dry column of silica gel (40 g). The column was washed with MeOH in CHCl$_3$: 200 mL (0.5%), 100 mL (1%), 100 ml (2%). The column was then eluted with 3% MeOH in CHCl$_3$. Fractions corresponding to a single spot of the product (TLC) were pooled and evaporated. The residue obtained was washed with ether and air dried to afford 0.067 g (3% for two steps) of compound 430 as a light yellow solid.

2,4-Diamino-5-[(N-methyl-3',4'-dichloroanilino)methyl]furo[2,3-d]pyrimidine (431)

To a 100 ml three neck round bottom flask was added anhydrous DMSO (30 ml), N-methyl-3,4-dichloroaniline (2.64 g), crude compound 117 (1.49 g) and anhydrous potassium carbonate (2.07 g). The reaction mixture was stirred at 45° C. for 24 h and then quenched with distilled water (150 ml). The resultant suspension was stirred at room temperature for 4 h and filtered. The residue was extracted with MeOH (100 mL) several times and extracts which gave a major spot of the product on TLC were pooled and mixed with silica gel (2 g). The mixture was evaporated under reduced pressure and then dried in vacuo. The residue was ground into a fine powder and poured on top of a dry column of silica gel (40 g). The column was washed with MeOH in CHCl$_3$: 200 mL (0.5%), 100 mL (1%), 100 ml (2%). The column was then eluted with 3% MeOH in CHCl$_3$. Fractions corresponding to a single spot (TLC) of the product were pooled and evaporated. The residue was washed with ether and air dried to afford 0.08 g (3% for two steps) of compound 431 as a white solid.

2,4-Diamino-5-[(N-methyl-3',4',5'-trichloroanilino) methyl]furo[2,3-d]-pyrimidine (432)

To a 100 ml three neck round bottom flask was added 3,4,5-trichloroaniline (1.96 g), potassium carbonate (1.66 g), acetonitrile (25 mL) and iodomethane (1.42 g). The reaction mixture was stirred at 40° C. for 3 days under nitrogen in the dark. The reaction mixture was then quenched with ethyl acetate (50 ml) and filtered. The residue was washed with ethyl acetate (3×20 ml). The filtrate and the washings were combined and washed with water (3×30 ml). The organic layer was then filtered through anhydrous MgSO$_4$ and evaporated under reduced pressure. The residue was dissolved in a minimum amount of ethyl acetate/hexane 1:12 and the solution was placed on a wet column of silica gel (80 g) and eluted with ethyl acetate/hexane 300 ml (1:12), 500 ml (1:8) to afford 0.88 g of N-methyl-3,4,5-trichloraniline (42%) as a white solid. The product was used directly for the condensation without characterization. To a 100 ml three neck round bottom flask was added anhydrous DMSO (5 ml), N-methyl-3,4,5-trichloroaniline (0.88 g) crude compound 117 (0.20 g) and anhydrous potassium carbonate (0.56 g). The reaction mixture was stirred at 45° C. for 24 h and then quenched with distilled water (15 ml). The resulting suspension was stirred at room temperature for 4 h and filtered. The residue was extracted with MeOH (100 ml) several times and the extracts which showed a major spot of the product on TLC were pooled and mixed with silica gel (2 g). The mixture was evaporated under reduced pressure and dried in vacuo. The residue was ground into fine powder and poured on top of a dry column of silica gel (40 g). The column was eluted with 3% MeOH in CHCl$_3$. Fractions corresponding to a single spot of the product were pooled and evaporated. The residue was washed with ether and air dried to afford 0.06 g (16% for two steps) of compound 432 as a light yellow solid.

2,4-Diamino-5-[(3'-methoxyanilino)methyl]furo[2,3-d]-pyrimidine (433)

To a 100 ml three neck round bottom flask was added anhydrous DMSO (15 ml), 3-methoxyanilino (0.93 g), crude compound 117 (0.75 g) and anhydrous potassium carbonate (1.04 g). The reaction mixture was stirred at 45° C. for 8 h and then quenched with distilled water (150 ml). The resulting suspension was stirred at room temperature for 8 h and filtered. The residue was dissolved in MeOH and the solution was mixed with silica gel (2 g). The mixture was evaporated under reduced pressure and dried in vacuo. The residue was ground into a fine powder and poured on top of a dry column of silica gel (40 g). The column was washed with 200 mL of 0.5%, 100 mL of 1%, 100 mL of 2% of MeOH in CHCl$_3$. The column was then eluted with 3% MeOH in CHCl$_3$. Fractions containing a single product spot were pooled and evaporated. The residue was washed with ether and air dried to afford 0.12 g (11% for two steps) of compound 433 as a white solid.

2,4-Diamino-5-[(N-methyl-2',5'-dimethoxyanilino) methyl]furo[2,3-$_d$]pyrimidine (434)

To a 100 ml three neck round bottom flask was added 2,5-dimethoxyaniline (1.53 g), anhydrous potassium carbonate (1.66 g), acetonitrile (25 ml) and iodomethane (1.42 g). The reaction mixture was stirred at 40° C. for 3 days under nitrogen in the dark. The reaction mixture was quenched with ethyl acetate (50 ml) and filtered. The residue was washed with ethyl acetate (3×20 ml). The filtrate and the washings were combined and washed with water (3×30 ml). The organic layer was filtered through MgSO$_4$ and evaporated under reduced pressure. The residue was dissolved in a minimum amount of ethyl acetate/hexane 1:8. The solution was placed on a wet column of silica gel (80 g) and eluted with ethyl acetate/hexane: 300 ml (1:8), 500 ml (1:5) to afford 0.51 g of N-methyl-2,5-dimethoxyaniline. To a 50 ml three neck round bottom flask with compound 117 (0.32 g, 1.61 mmol), N-methyl-2,5-dimethoxyaniline (0.40 g) and anhydrous potassium carbonate (0.27 g) was added anhydrous DMSO (3 ml) and the reaction mixture stirred at 45° C. for 8 h under nitrogen in the dark. Distilled water (10 ml) was added to precipitate the product and the suspension stirred for 2 h and then cooled to 5° C. and filtered. The solid was washed with cold water (2×2 ml) suspended in MeOH (200 ml). Silica gel (1 g) was added and the suspension sonicated and then heated to 50° C. for 15 min. The suspension was then evaporated under reduced pressure and dried in vacuo at room temperature for 10 h. The residue was powdered and poured on top of a wet column of silica gel (40 g) and eluted with 5% of MeOH in CHCl$_3$. Fractions corresponding the product spot (TLC) were pooled and evaporated. The residue was washed with ether and air dried to afford 0.15 g (28%) of compound 434 as a white solid.

Example 29

Compounds 420–434, prepared as described in Example 28, were tested for inhibiting DHFR according to the methods of Example 1. The inhibitory concentration (IC$_{50}$) values along with the selectivity ratios (IC$_{50}$) rlDHRF/IC$_{50}$ pcDHRF or tgDHFR) for compounds 420–434 are listed in Table 23 along with epiroprim and TMP. Compound 422, the S-2-naphthyl, and compound 428, the NH-2-biphenyl, were extremely selective against pcDHFR with selectivity ratios of 18.9 and 17.8, respectively. Compound 422 was also significantly potent against pcDHFR (IC$_{50}$ of 0.66 µM). Compared to epiroprim and TMP, compound 422 is significantly more potent and more selective against pcDHFR. Compound 428 displayed high selectivity for pcDHFR at 17.8 with an IC$_{50}$ of 7.7 µM comparable to epiroprim and TMP in potency but with better selectivity. The other analogues were neither potent nor significantly selective. The results suggest that all three features, namely the heterocyclic ring, the bridge and the side chain aryl moiety combine to provide pcDHFR selectivity in the series.

TABLE 25

Inhibitor Concentrations (IC$_{50}$, $\mu$M) and Selectivity Ratios of 5-Substituted Furo[2,3-d]pyrimidines Against pcDHFR, tgDHFR and rlDHFR. (5,8)

| | pcDHFR | rlDHFR | rl/pc | tgDHFR | rl/tg |
|---|---|---|---|---|---|
| 420 | >26 | 252 | ND | >26 | ND |
| 421 | 19 | 23 | 1.2 | 19 | 1.2 |
| 422 | 0.65 | 12.3 | 18.9 | 11.6 | 1.1 |
| 423 | 13.5 | 12 | 0.89 | 37 | 0.32 |
| 424 | 41 | 36.5 | 0.89 | 38 | 0.96 |
| 425 | 14 | 60.3 | 4.31 | >42 | ND |
| 426 | >12 | >12 | ND | >12 | ND |
| 427 | 8.1 | 16.2 | 2.00 | 32.4 | 0.50 |
| 428 | 7.7 | 187 | 17.79 | 45.4 | 3.02 |
| 429 | 14.8 | 1406 | 0.99 | 23.6 | 0.62 |
| 430 | 50.9 | 71.9 | 1.4 | >47 | ND |
| 431 | 44.8 | >27 | ND | >27 | ND |
| 432 | 284 | 34.3 | 0.1 | 21.5 | 1.6 |
| 433 | >31.3 | >31.3 | ND | >31.3 | ND |
| 434 | >27 | >27 | ND | >27 | ND |
| TMP | 12 | 133 | 11.1 | 2.7 | 49 |
| Epiroprim | 2.6 | 33.2 | 12.8 | 0.48 | 70.6 |

Example 30

Compounds having the general formula 14, as more specifically identified below, were evaluated as inhibitors of DHFR in the manner described above in Example 1, except that the compounds were not compared with TMQ, PTX, TMP or MTX. Compound numbers correspond with those described in Table 5 above.

Table 26 below illustrates the results of the testing.

TABLE 26

Inhibitory Concentrations (IC$_{50}$ $\mu$M) and Selectivity Ratios

| Compound # | Pc DHFR[1] | RL DHFR[1] | Selectivity Ratio: RL DHFR/Pc DHFR | Tg DHFR[1] | Selectivity Ratio: RL DHFR/Tg |
|---|---|---|---|---|---|
| 113-102 | 38 | 97 | 2.55 | 17% @ 75 $\mu$M | ND |
| 113-103 | 28% @ 28 $\mu$M | 6.4 | ND | 6.3 | 1.00 |
| 113-118 | 60% @ 31 $\mu$M | 48% @ 31 $\mu$M | ND | 15% @ 31 $\mu$M | ND |
| 113-125 | 0% @ 11 $\mu$M | 49% @ 11 $\mu$M | ND | 12.2 | ND |
| 113-143 | 51% @ 61 $\mu$M | 39% @ 61 $\mu$M | ND | 34% @ 61 $\mu$M | ND |
| 113-143B | 18% @ 40 $\mu$M | 3.7 | <0.11 | 6 | 0.62 |
| 113-148 | 45% @ 85 $\mu$M | 27% @ 85 $\mu$M | ND | 27% @ 85 $\mu$M | ND |
| 113-154B | 36 | 1.8 | 0.05 | 4.4 | 0.41 |
| 113-149 | 10% @ 35 $\mu$M | 13% @ 35 $\mu$M | ND | 13% @ 35 $\mu$M | ND |
| 113-154A | 55 | 2.3 | 0.04 | 10.2 | 0.23 |

As noted in the table, some of the inhibition did not reach 50%. For those results, the % inhibition and the concentration at which this % was achieved are noted. As can be seen from the above table, these compounds would have a relatively low toxicity to mammals.

Example 31

Compounds having the general formula 14, as specifically identified below, were evaluated as inhibitors of DHFR and TS as generally described in Examples 6–8. Some of the compounds were compared with TMP and MTX and/or ZD1694. All of the compounds were also compared with LY231514, which is a thymidylate synthase inhibitor. Results are presented in Tables 27 and 28 below.

TABLE 27

Inhibition of Dihydrofolate Reductase (IC$_{50}$ in $\mu$M)

| Compound | Molecular Weight | L. casei |
|---|---|---|
| 113-102 | 348 | >2.9 × 10$^{-5}$ (17%)* |
| 113-103 | 254 | 3.9 × 10$^{-6}$ |
| 113-118 | 395 | >2.5 × 10$^{31}$ $^5$ (0%) |
| 113-125 | 292 | 3.4 × 10$^{-6}$ |
| 113-143 | 402 | >2.5 × 10$^{-5}$ (8%) |
| 113-148 | 372 | 2.7 × 10$^{-5}$ |
| 113-154B | 289 | 3.5 × 10$^{-6}$ |
| 113-149 | 445 | >2.3 × 10$^{-5}$ (8%) |
| 113-154A | 342 | 2.9 × 10$^{-6}$ |
| 113-161 | 426 | 2.4 × 10$^{-8}$ |
| LY231514** | 427 | 2.3 × 10$^{-4}$ |
| trimethoprim | 290 | 3.5 × 10$^{-7}$ |
| methotrexate | 454 | 1.10 × 10$^{-8}$ |

*FIGS. in parentheses indicate the % inhibition obtained at the stated concentration.
**Kindly provided by D. Chuan Shih, Eli Lilly & Co.

TABLE 28

Inhibition of thymidylate synthase (IC$_{50}$ in $\mu$M)

| Compound | Molecular Weight | L. casei |
|---|---|---|
| 113-161 | 426 | 9.8 × 10$^{-6}$ |
| LY231514** | 427 | 2.1 × 10$^{-5}$ |
| ZD 1694*** | 458 | 8.0 × 10$^{-6}$ |

**Kindly provided by D. Chuan Shih, Eli Lilly & Co.
***Kindly provided by Zeneca Pharmaceuticals.

Example 32

Figure 21:
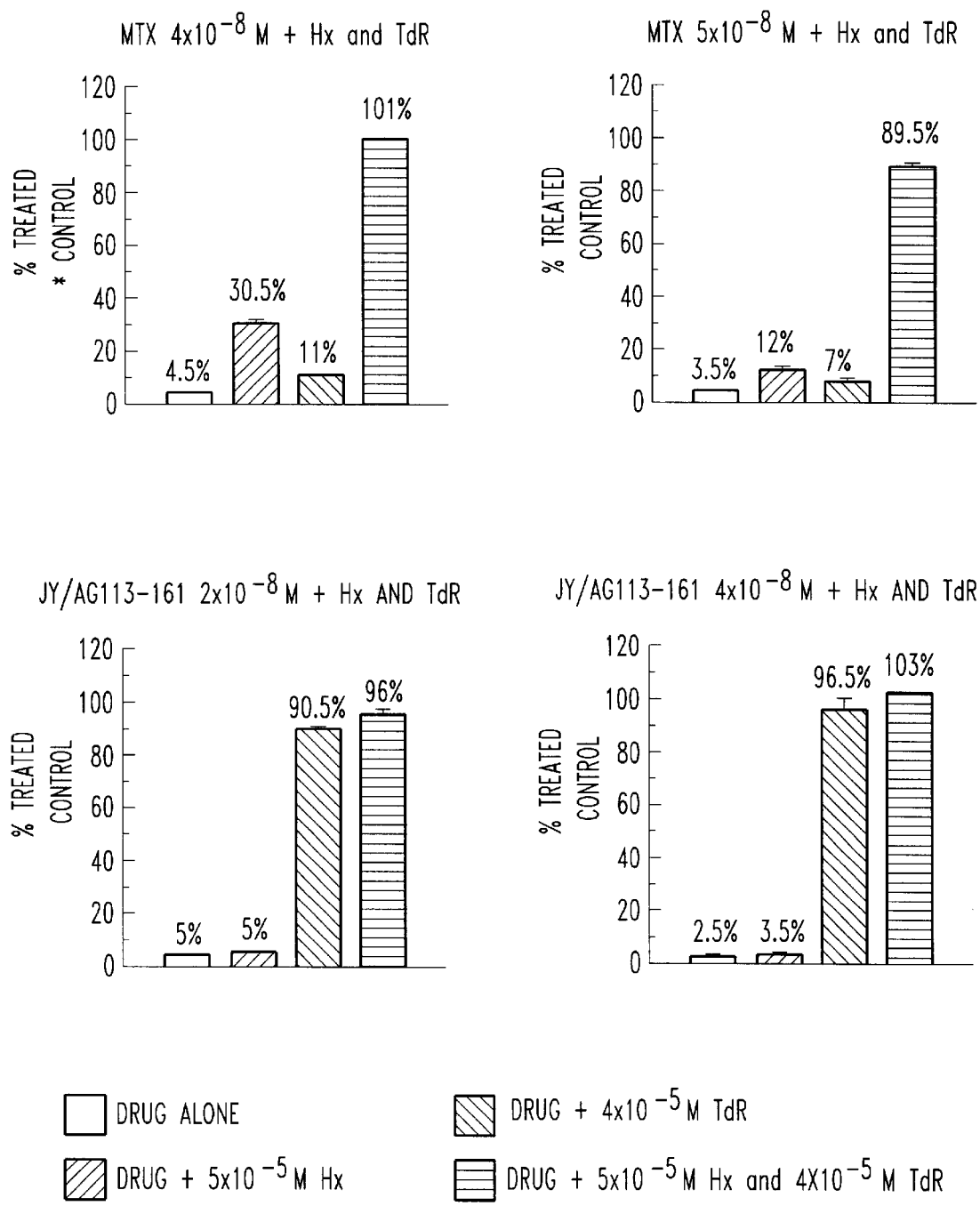
FIG. 21 shows the level of protection of FaDu cells from MTX (FIGS. 21A, 21B) and compound 113–161 (FIGS. 21C, 21D), determined according to Example 32.

Compound 113–161 was also tested for its ability to inhibit the growth of FaDu human squamous cell carcinoma cell lines. Performance was tested against MTX using hypoxanthine (Hx) and Thymidine (TdR). Results are shown in FIG. 21. The protection study indicates that 113–161 almost completely reversed the TS inhibition unlike MTX, and almost completely reversed DHFR and TS when both were supplied.

Figure 22:
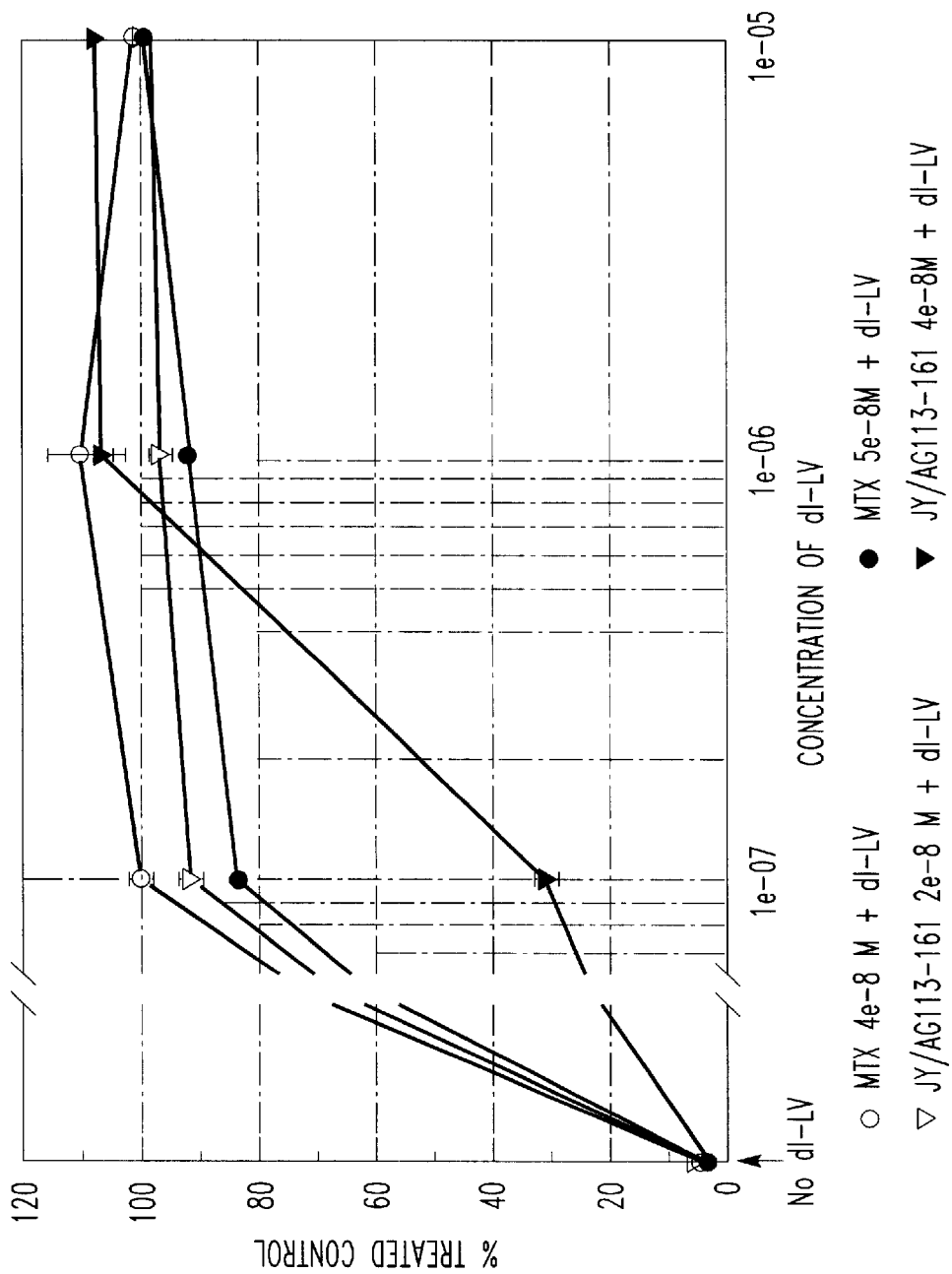
FIG. 22 shows the protection at 120 hours of FaDu cells from MTX and 113–161, determined according to Example 32.

Protection after 120 hours with di-LV was also determined. Results are shown in FIG. 22. All of the tested compounds reversed inhibition with leucovorin.

Example 33

The compounds identified in Table 29 below were further tested for their in vitro anti-cancer activity by the National Cancer Institute. GI$_{50}$ represents the concentration at which growth was inhibited by 50%.

TABLE 29

In Vitro Anti-Cancer Activity

| Panel/Cell Line | 113-102 GI$_{50}$ | 113-103 GI$_{50}$ | 113-118 GI$_{50}$ | 113-125 GI$_{50}$ | 113-143 GI$_{50}$ | 113-148 GI$_{50}$ | 113-154B GI$_{50}$ | 113-149 GI$_{50}$ | 113-154A GI$_{50}$ |
|---|---|---|---|---|---|---|---|---|---|
| Leukemia | | | | | | | | | |
| CCRF-CEM | 4.72E−06 | 1.33E−05 | >1.00E−04 | >1.00E−04 | >1.00E−04 | 2.97E−06 | 2.42E−05 | 5.80E−08 | |
| HL-60 (TB) | 2.01E−05 | | >1.00E−04 | >1.00E−04 | 3.95E−05 | 4.81E−06 | 2.38E−05 | 6.47E−08 | 4.18E−05 |
| K-562 | >1.00E−04 | 4.85E−05 | | 3.38E−05 | 8.60E−06 | 5.91E−06 | 2.43E−05 | 8.46E−08 | 2.30E−05 |
| MOLT-4 | >1.00E−04 | 2.06E−05 | | 1.73E−05 | 8.07E−06 | 7.46E−06 | 1.93E−05 | 2.85E−07 | 3.87E−05 |
| RPMI-8226 | >1.00E−04 | 6.02E−05 | >1.00E−04 | 7.16E−05 | | | 7.67E−05 | 4.39E−07 | 6.74E−05 |
| SR | >1.00E−04 | 5.95E−05 | | 3.16E−05 | 4.91E−06 | 3.51E−06 | 2.43E−05 | 3.14E−08 | 3.25E−05 |
| Non-Small Cell Lung Cancer | | | | | | | | | |
| A549/ATCC | >1.00E−04 | 2.96E−05 | 9.98E−05 | 5.43E−05 | >>1.00E−04 | 6.46E−06 | 2.12E−05 | 1.73E−07 | 2.61E−05 |
| EKVX | 6.45E−06 | 9.35E−08 | | 7.09E−05 | >1.00E−04 | 5.78E−06 | 9.27E−07 | 4.24E−07 | 5.21E−06 |
| HOP-92 | 1.60E−05 | 6.34E−05 | 3.10E−05 | 2.41E−05 | 3.16E−05 | 1.63E−05 | 4.00E−05 | 4.67E−07 | 1.82E−05 |
| NCI-H226 | >1.00E−04 | >1.00E−04 | >1.00E−04 | >1.00E−04 | >1.00E−04 | 1.24E−05 | 3.54E−05 | 1.95E−07 | 2.30E−05 |
| NCI-H23 | >1.00E−04 | >1.00E−04 | 9.73E−05 | >1.00E−04 | 6.66E−05 | 8.47E−06 | 3.68E−05 | 2.78E−07 | 2.69E−05 |
| NCI-H322M | >1.00E−04 | 5.99E−05 | 7.47E−05 | >1.00E−04 | >1.00E−04 | 1.01E−05 | >1.00E−04 | 5.81E−07 | 2.69E−05 |
| NCI-H460 | >1.00E−04 | 3.45E−05 | 4.25E−05 | 6.02E−05 | >1.00E−04 | 7.70E−06 | 1.39E−05 | 1.62E−07 | 1.93E−05 |
| NCI-H522 | >1.00E−04 | 8.40E−05 | 2.91E−05 | 3.44E−05 | 6.24E−06 | 8.34E−06 | 3.38E−05 | 4.77E−08 | 2.50E−05 |
| Colon Cancer | | | | | | | | | |
| COLO 205 | >1.00E−04 | 6.65E−05 | 3.82E−05 | >1.00E−04 | 3.44E−05 | 1.17E−05 | 5.99E−05 | 1.90E−07 | 4.82E−05 |
| HCC-2998 | >1.00E−04 | 6.90E−05 | | | | | 1.74E−05 | 3.17E−07 | |
| HCT-116 | >1.00E−04 | 3.60E−05 | 4.83E−05 | >1.00E−04 | >1.00E−04 | 4.51E−06 | 3.19E−05 | 2.86E−07 | 3.68E−05 |
| HCT-15 | 2.52E−05 | 5.53E−05 | 5.14E−05 | 5.79E−05 | 4.89E−05 | 1.02.E−05 | 2.04E−05 | 1.27E−07 | 2.43E−05 |
| HT29 | >1.00E−04 | 3.67E−05 | 4.84E−05 | >1.00E−04 | >1.00E−04 | 4.77E−06 | 3.84E−05 | 2.81E−07 | 1.00E−05 |
| KM12 | >1.00E−04 | 5.06E−05 | 4.84E−05 | >1.00E−04 | >1.00E−04 | 1.22E−05 | 3.47E−05 | 1.94E−07 | 4.65E−05 |
| SW-620 | 4.16E−05 | >1.00E−04 | >1.00E−04 | >1.00E−04 | >1.00E−04 | 1.71E−05 | 7.34E−05 | 2.36E−07 | |
| CNS Cancer | | | | | | | | | |
| SF-268 | >1.00E−04 | >1.00E−04 | >1.00E−04 | 3.71E−05 | >1.00E−04 | 1.10E−05 | 4.55E−05 | 6.69E−07 | 3.95E−05 |
| SF-295 | >1.00E−04 | 5.12E−05 | 7.93E−05 | 4.97E−05 | 1.78E−05 | 8.43E−06 | 3.51E−05 | 4.18E−08 | 3.66E−05 |
| SF-539 | >1.00E−04 | >1.00E−04 | 3.02E−05 | 2.18E−05 | 3.39E−05 | 7.20E−06 | 3.80E−05 | 7.45E−08 | 2.04E−05 |
| SNB-19 | >1.00E−04 | >1.00E−04 | >1.00E−04 | 3.74E−05 | >1.00E−04 | 1.09E−05 | 7.04E−05 | 2.73E−07 | 6.74E−05 |
| SNB-75 | >1.00E−04 | 7.38E−08 | >1.00E−04 | 2.42E−05 | >1.00E−04 | 1.76E−05 | 3.62E−05 | 3.58E−07 | 2.75E−05 |
| U251 | 1.22E−05 | 4.40E−05 | | 3.00E−05 | 3.11E−06 | 1.04E−05 | 2.95E−05 | 1.44E−07 | 2.34E−05 |
| Melanoma | | | | | | | | | |
| LOX IMVI | >1.00E−04 | 5.13E−05 | 5.00E−05 | 7.31E−05 | 2.59E−05 | 1.37E−05 | 4.10E−05 | 2.50E−07 | 3.00E−05 |
| MALME-3M | >1.00E−04 | >1.00E−04 | 1.95E−05 | >1.00E−04 | 3.96E−05 | 1.86E−05 | 4.69E−05 | 2.83E−07 | 4.74E−05 |
| M14 | >1.00E−04 | 4.83E−05 | 9.36E−05 | >1.00E−04 | >1.00E−04 | 1.20E−05 | 5.40E−05 | 7.70E−08 | 2.98E−05 |
| SK-MEL-2 | >1.00E−04 | >1.00E−04 | >1.00E−04 | >1.00E−04 | >1.00E−04 | 1.31E−05 | >1.00E−04 | 3.81E−07 | 9.83E−05 |
| SK-MEL-28 | 3.93E−05 | >1.00E−04 | >1.00E−04 | >1.00E−04 | >1.00E−04 | 1.57E−05 | >1.00E−04 | 1.15E−05 | >1.00E−05 |
| SK-MEL-5 | >1.00E−04 | 6.91E−05 | | >1.00E−04 | 1.28E−05 | 5.80E−06 | 2.95E−05 | 6.11E−08 | 3.73E−05 |
| UACC-257 | 3.14E−05 | 5.42E−05 | | >1.00E−04 | 9.09E−06 | 6.36E−06 | 3.81E−05 | 8.02E−08 | 5.64E−05 |
| UACC-62 | 7.94E−05 | >1.00E−04 | 8.00E−05 | >1.00E−04 | >1.00E−04 | 1.23E−05 | 3.20E−05 | 3.99E−08 | 1.96E−05 |
| Ovarian Cancer | | | | | | | | | |
| IGROV1 | >1.00E−04 | 5.99E−05 | 6.82E−05 | >1.00E−04 | >1.00E−04 | 1.42E−05 | 3.63E−05 | 6.11E−08 | 1.73E−05 |
| OVCAR-3 | >1.00E−04 | >1.00E−04 | >1.00E−04 | >1.00E−04 | >1.00E−04 | 1.48E−05 | 8.33E−05 | 2.88E−08 | 7.48E−05 |
| OVCAR-4 | 5.63E−05 | 8.70E−05 | 8.01E−05 | >1.00E−04 | >1.00E−04 | 8.88E−06 | 4.79E−05 | 8.21E−07 | 7.78E−05 |
| OVCAR-5 | >1.00E−04 | >1.00E−04 | >1.00E−04 | >1.00E−04 | >1.00E−04 | 1.08E−05 | >1.00E−04 | 2.60E−06 | |
| OVCAR-8 | >1.00E−04 | 6.56E−05 | 5.25E−05 | 6.44E−05 | >1.00E−04 | 1.76E−05 | 4.02E−05 | 3.64E−07 | 3.11E−05 |
| SK-OV-3 | >1.00E−04 | >1.00E−04 | >1.00E−04 | >1.00E−04 | >1.00E−04 | 1.73E−05 | 7.68E−05 | 5.06E−07 | 8.88E−05 |
| Renal Cancer | | | | | | | | | |
| 786-0 | >1.00E−04 | 3.98E−05 | >1.00E−04 | 4.45E−05 | >1.00E−04 | 1.16E−05 | 3.63E−05 | 2.54E−07 | 3.28E−05 |
| A498 | 1.43E−05 | >1.00E−04 | 1.42E−05 | 5.28E−05 | 7.02E−08 | 1.94E−06 | 1.34E−05 | 1.36E−07 | 8.45E−07 |
| ACHN | 4.40E−05 | >1.00E−04 | 3.48E−05 | >1.00E−04 | 6.26E−06 | 7.99E−06 | 3.75E−05 | 7.28E−07 | 3.57E−05 |
| CAKI-1 | 8.79E−05 | 8.35E−05 | >1.00E−04 | 3.02E−05 | >1.00E−04 | 1.16E−05 | 5.57E−05 | 3.66E−07 | 4.95E−05 |
| RXF 393 | 4.81E−06 | 1.83E−05 | 9.47E−05 | 2.56E−05 | >1.00E−04 | 1.11E−05 | 3.02E−05 | 1.34E−07 | 3.27E−05 |
| SN12C | >1.00E−04 | 2.73E−05 | >1.00E−04 | >1.00E−04 | >1.00E−04 | 1.33E−05 | 5.80E−05 | 5.37E−07 | 4.31E−05 |
| TK-10 | >1.00E−04 | 8.87E−05 | >1.00E−04 | >1.00E−04 | >1.00E−04 | 1.02E−05 | 5.51E−05 | 9.61E−07 | 5.89E−05 |
| UO-31 | >1.00E−04 | 2.19E−05 | >1.00E−04 | 4.81E−05 | >1.00E−04 | 4.78E−06 | 2.94E−05 | 3.47E−07 | 3.40E−05 |
| Prostate Cancer | | | | | | | | | |
| PC-3 | 3.81E−05 | 3.33E−05 | 6.40E−05 | >1.00E−04 | >1.00E−04 | 9.47E−06 | 2.78E−055 | 4.79E−08 | 2.22E−05 |
| DU-145 | >1.00E−04 | 1.75E−05 | >1.00E−04 | >1.00E−04 | >1.00E−04 | 1.31E−05 | 5.53E−05 | 2.24E−07 | 7.56E−05 |
| Breast Cancer | | | | | | | | | |
| MCF7 | 5.00E−05 | >1.00E−04 | 2.96E−05 | 6.19E−05 | 4.39E−05 | 1.26E−05 | 3.31E−05 | 1.18E−07 | 2.72E−05 |
| NCI/ADR-RES | 2.23E−06 | 5.67E−05 | | 7.44E−05 | 4.22E−06 | 6.75E−06 | 1.10E−05 | 1.45E−07 | 2.59E−05 |
| MDA-MB- | 5.22E−05 | >1.00E−04 | <1.00E−04 | 9.10E−05 | >1.00E−04 | 1.08E−05 | 8.31E−05 | 5.95E−07 | 3.73E−05 |

TABLE 29-continued

In Vitro Anti-Cancer Activity

| Panel/Cell Line | 113-102 $GI_{50}$ | 113-103 $GI_{50}$ | 113-118 $GI_{50}$ | 113-125 $GI_{50}$ | 113-143 $GI_{50}$ | 113-148 $GI_{50}$ | 113-154B $GI_{50}$ | 113-149 $GI_{50}$ | 113-154A $GI_{50}$ |
|---|---|---|---|---|---|---|---|---|---|
| 231/ATCC | | | | | | | | | |
| HS 578T | >1.00E−04 | 5.18E−06 | <1.00E−04 | 8.07E−05 | >1.00E−04 | 1.49E−05 | 2.23E−05 | 2.83E−07 | 2.70E−05 |
| MDA-MB-435 | >1.00E−04 | >1.00E−04 | 9.54E−05 | 5.91E−05 | >1.00E−04 | 1.30E−05 | 5.59E−05 | 1.01E−08 | 3.92E−05 |
| MDA-N | >1.00E−04 | 4.11E−05 | 7.83E−05 | 7.55E−05 | >1.00E−04 | 1.47E−05 | 4.65E−05 | <1.00E−08 | 3.53E−05 |
| BT-549 | >1.00E−04 | >1.00E−04 | 4.09E−05 | 5.21E−05 | >1.00E−04 | 1.58E−05 | 1.86E−05 | 7.80E−06 | 1.93E−05 |
| T-47D | 5.04E−07 | 9.82E−06 | | 6.64E−05 | | 3.84E−06 | 3.10E−05 | 5.63E−07 | 6.02E−05 |

As can be seen from Table 29, several of the compounds were very selective against various cell lines. For example, compound 113–102 was very selective against the CCRf-CEM leukemia cell line, the RXF-393 renal cancer cell line and the NCI/ADR-RES breast cancer cell line. Compound 113–103 was selective against the EKVX non-small cell lung cancer and the SNB-75 CNS cancer cell lines. Compound 113–143 was very potent against the A498 renal cancer cell line and also showed high selectivity against other cell lines (K-562, MOLT-4, SR, NCI-H522, U251, UACC-257, ACHN, and NCI/ADR-RES). Compound 113–154B is selective against EKUX non-small cell lung cancer and compound 113–149 has selectivity against numerous cell lines. Compound 113–154A is selective against EKUX non-small lung cancer and A498 renal cancer cell lines.

Example 34

Compounds having the general formula 15, as specifically identified below, were tested for their ability to inhibit DHFR as generally described in Example 1. Compound numbers correspond with those described in Table 3. Results are presented in Table 30 below.

TABLE 30

Inhibitory Concentrations ($IC_{50}\mu M$) and Selectivity Ratios

| Compound No. | Pc DHFR[1] | RL DHFR[1] | Selectivity Ratio: RL DHFR/Pc DHFR | Tg DHFR[1] | Selectivity Ratio: RL DHFR/Tg DHFR |
|---|---|---|---|---|---|
| 111-157B | 50% @ 51 μM | 37% @ 51 μM | ND | 15.4 | >3.3 |
| 111-178 | 30% @ 14 μM | 0% @ 14 μM | ND | 15% @ 14 μM | ND |
| 111-183 | 38% @ 29 μM | 10% @ 29 μM | ND | 38% @ 29 μM | ND |
| 111-184 | 36.2 | 40% @ 10 μM | ND | 27.7 | ND |
| 111-190 | 10.3 | 20% @ 32 μM | >3.2 | 38% @ 32 μM | ND |
| 111-191 | 16.2 | 12.6 | 0.78 | 4.5 | 2.80 |
| 111-192 | 8% @ 12 μM | 34% @ 13 μM | ND | 63 | ND |
| 111-194 | 57% @ 63 μM | 34% @ 63 μM | ND | 29% @ 63 μM | ND |
| 111-204 | 193 | 12% @ 38 μM | >2 | 31% @ 38 μM | ND |

Compounds 111–190 and 111–204 showed high selectivity against rat liver DHFR.

Example 35

A compound corresponding to general formula 14 was synthesized using the following method. For compound 23m, synthesized according to the following method, $R_{18}$ is $CH_3$, $R_{13}$ is H, $Z_5$ is $R_{14}$ which is H, $A_1$ is CH, $B_1$ is $CH_1$, $R_{15}$ is H, $R_{16}$ is H, and $R_{17}$ is p-benzoyl-L-glutamate.

Figure 23:
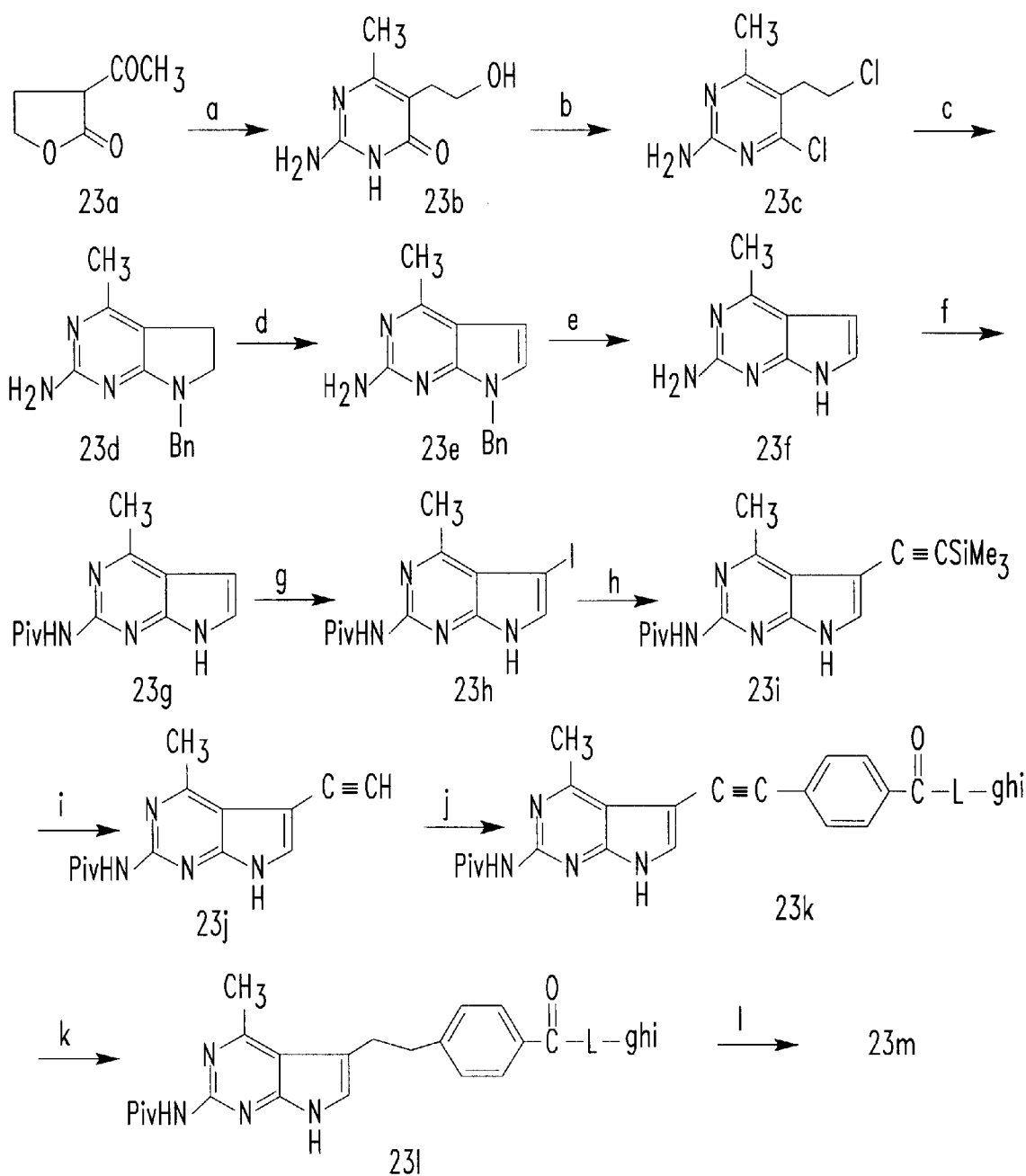
FIG. 23 shows a schematic diagram of the methods of preparing a compound having Formula 14, as described in Example 35.

Reagents and conditions used in the synthesis of the compound are as follows. Letters correspond with those shown in FIG. 23. a) guanidine carbonate, EtOH, triethylamine, reflux, 69%. b) $SOCl_2$, reflux, 68%. c) benzylamine, triethylamine, n-BuOH, 90° C., 50%. d) $MnO_2$, 1,4-dioxane, reflux, 45%. e) Na/liq. $NH_3$, −78° C., 70%. f) PivCl, pyridine, reflux, 75%. g) NIS, dark, rt, 52%. h) trimethylsilylacetylene, tetrakis(triphenylphosphine)palladium(0), CuI, triethylamine, THF, rt. i) n-$Bu_4NF$, THF, rt, 60%, two steps. j) diethyl 4-iodobenzoyl-L-glutamate, tetrakis(triphenylphosphine)palladium(0), CuI, triethylamine, THF, rt, 42%. k) 5% Pd/C, $H_2$, 50 psi., 70%. l) 1N NaOH, MeOH, 50° C., 71%.

The synthesis of target compound 23m (as described above) was initiated from 2-acetylbutyrolactone 23a which was used to synthesize 5-(2-hydroxyethyl)-6-methyl-2-thiouracil according to the methods generally taught by Badaway, J. Heterocyclic Chem. 33:229 (1996). This method was modified to access a new synthetic pathway for the intermediate 23d. Compound 23a and guanidine carbonate were refluxed with absolute ethanol in the presence of triethylamine to give 23b in 69% yield. Compound 23b was converted to 23c in 68% yield by refluxing with phosphorus oxychloride. The condensation step was carried out by refluxing a mixture of 23c, benzylamine and triethylamine in n-BuOH, which afforded 23d in 50% yield. $MnO_2$ can be used to obtain 23e in reasonable yield (45%).

Dissolving Na/liq. $NH_3$ conditions were used to afford the product 23f in good yield (70%) from compound 23e. These methods are generally described by Hoops, et al., J. Heterocyclic Chem. 33:767 (1996) and Meade and Beuchamp, J. Heterocyclic Chem. 33:303 (1996).

The 2-amino group of intermediate 23f was protected with pivaloyl chloride, which both increases the solubility of 23 g and controls the regioselectivity of iodination in the subsequent step. Compound 23h was the only product obtained using NIS as the iodinating agent. Coupling of 23h with trimethylsilylacetylene in the presence of tetrakis(triphenylphosphine)palladium(0), copper(I) iodide and triethylamine in THF afforded compound 23i following the procedure generally taught by Shih and Gossett, Heterocycles, 36:825 (1993). The silyl protecting group of 23i was then removed by fluoide ion to give compound 23j (60% yield overall in two steps). Compound 23j was then coupled successfully with diethyl 4-iodobenzoyl-L-glutamate, under similar palladium-catalyzed reaction conditions as were employed in converting 23h to 23i, to give compound 23k in 43% yield. Subsequent catalytic hydrogenation (5% Pd-C/$H_2$/50 psi) and saponification afforded target compound 23m.

Example 36

The compounds identified below were further tested for their in vitro anticancer activity by the National Cancer Institute. Results are presented in Table 31 below. $GI_{50}$ represents the concentration at which growth was inhibited by 50%.

TABLE 31

In Vitro Anti-Cancer Activity

| Panel/Cell Line | 111-157B | 111-178 | 111-183 | 111-184 | 111-190 | 111-191 | 111-192 | 111-194 | 111-204 |
|---|---|---|---|---|---|---|---|---|---|
| Leukemia | | | | | | | | | |
| CCRF-CEM | 1.66E−05 | 1.31E−05 | 1.00E−05 | >1.00E−04 | 6.89E−05 | 4.06E−05 | 2.54E−05 | >1.00E−04 | 6.54E−05 |
| HL-60 (TB) | 1.59E−05 | 1.64E−05 | 1.82E−05 | >1.00E−04 | 4.52E−05 | | | >1.00E−04 | |
| K-562 | 3.38E−05 | 3.70E−05 | 2.58E−05 | >1.00E−04 | 1.88E−05 | >1.00E−04 | 3.03E−05 | >1.00E−04 | >1.00E−05 |
| MOLT-4 | 2.06E−05 | 1.73E−05 | 1.03E−05 | >1.00E−04 | 2.92E−05 | 3.12E−05 | 2.61E−05 | 4.52E−05 | >1.00E−04 |
| RPMI-8226 | 2.98E−05 | 1.07E−05 | 2.82E−05 | >1.00E−04 | 4.69E−05 | 2.53E−05 | 2.76E−05 | 6.96E−05 | >1.00E−04 |
| SR | 8.36E−06 | 1.56E−05 | 9.52E−06 | >1.00E−04 | 5.02E−05 | 1.19E−05 | 7.14E−05 | 1.44E−05 | 5.48E−05 |
| Non-Small Cell Lung Cancer | | | | | | | | | |
| A549/ATCC | 1.52E−05 | 1.41E−05 | 1.51E−05 | >1.00E−04 | 2.73E−05 | 2.06E−05 | 2.73E−05 | 3.40E−05 | >1.00E−04 |
| EKVX | 1.45E−05 | 2.93E−05 | 2.74E−05 | >1.00E−04 | 1.67E−05 | >1.00E−04 | 2.11E−05 | >1.00E−04 | >1.00E−04 |
| HOP-62 | 1.24E−05 | 1.36E−05 | 4.36E−06 | >1.00E−04 | 1.70E−05 | 3.72E−06 | 3.67E−05 | 3.20E−05 | 2.08E−05 |
| HOP-92 | 1.46E−05 | 1.68E−05 | 1.08E−05 | >1.00E−04 | 1.93E−05 | 9.38E−06 | 1.85E−05 | 6.57E−05 | 2.21E−05 |
| NCI-H226 | 1.53E−05 | 2.99E−05 | >1.00E−04 | >1.00E−04 | 3.00E−05 | >1.00E−04 | 2.96E−05 | >1.00E−04 | >1.00E−05 |
| NCI-H23 | 1.75E−05 | 1.57E−05 | 2.70E−05 | >1.00E−04 | 3.55E−05 | >1.00E−04 | 2.93E−05 | >1.00E−04 | >1.00E−04 |
| NCI-H322M | 1.44E−05 | 3.36E−05 | 2.66E−05 | >1.00E−04 | 1.99E−05 | >1.00E−04 | 2.71E−05 | 7.12E−05 | 6.92E−05 |
| NCI-H460 | 1.37E−05 | 7.51E−06 | 5.41E−06 | >1.00E−04 | 1.28E−05 | 5.12E−06 | 2.23E−05 | 3.92E−05 | >1.00E−04 |
| NCI-H522 | 1.47E−05 | 1.54E−05 | 6.14E−05 | >1.00E−04 | 3.65E−05 | >1.00E−04 | 2.31E−05 | >1.00E−04 | >1.00E−04 |
| Colon Cancer | | | | | | | | | |
| COLO 205 | 3.02E−05 | 3.74E−05 | >1.00E−04 | >1.00E−04 | 7.17E−05 | >1.00E−04 | 1.86E−05 | >1.00E−04 | 8.37E−05 |
| HCC-2998 | 1.91E−05 | 1.04E−05 | 2.54E−05 | >1.00E−04 | 2.13E−05 | >1.00E−04 | 3.76E−05 | >1.00E−04 | >1.00E−04 |
| HCT-116 | 1.68E−05 | 2.03E−05 | 2.88E−05 | >1.00E−04 | 3.00E−05 | >1.00E−04 | 2.47E−05 | 4.19E−05 | >1.00E−04 |
| HCT-15 | 3.05E−05 | 9.31E−06 | 4.39E−06 | >1.00E−04 | 8.39E−05 | >1.00E−04 | 3.35E−05 | >1.00E−04 | >1.00E−04 |
| HT29 | 2.46E−05 | 2.40E−05 | 2.22E−05 | >1.00E−04 | 2.31E−05 | >1.00E−04 | 2.59E−05 | >1.00E−04 | >1.00E−04 |
| KM12 | 2.65E−05 | 3.10E−05 | 3.15E−05 | >1.00E−04 | 4.78E−05 | >1.00E−04 | 1.71E−05 | >1.00E−04 | >1.00E−04 |
| SW-620 | 2.56E−05 | 1.73E−05 | 2.89E−05 | >1.00E−04 | 5.18E−05 | 6.46E−05 | 4.91E−05 | >1.00E−04 | >1.00E−04 |
| CNS Cancer | | | | | | | | | |
| SF-268 | 1.49E−05 | 2.95E−05 | 1.05E−05 | >1.00E−04 | 1.24E−05 | 8.78E−06 | 2.19E−05 | 5.81E−05 | 6.29E−05 |
| SF-295 | 1.90E−05 | 1.43E−05 | 1.85E−05 | >1.00E−04 | 1.92E−05 | 4.62E−05 | 4.21E−05 | 4.08E−05 | 7.09E−05 |
| SF-539 | 2.23E−05 | 2.57E−05 | 4.86E−05 | >1.00E−04 | 2.92E−05 | 7.01E−05 | 8.79E−05 | 3.07E−05 | >1.00E−04 |
| SNB-19 | 1.31E−05 | 2.53E−05 | 1.68E−05 | >1.00E−04 | 2.63E−05 | >1.00E−04 | 4.51E−05 | 5.48E−05 | >1.00E−04 |
| SNB-75 | 3.61E−06 | 7.87E−06 | 7.07E−06 | >1.00E−04 | 7.90E−06 | 3.36E−06 | 2.57E−05 | 1.49E−05 | 2.01E−05 |
| U251 | 1.45E−05 | 1.63E−05 | 1.22E−05 | >1.00E−04 | 1.54E−05 | 9.15E−06 | 3.25E−05 | 3.07E−05 | 3.14E−05 |
| Melanoma | | | | | | | | | |
| LOX IMVI | 1.66E−05 | 2.43E−05 | 9.24E−06 | >1.00E−04 | 2.70E−05 | 5.73E−05 | 1.77E−05 | 5.98E−05 | >1.00E−04 |
| MALME-3M | 6.74E−06 | 1.80E−05 | 1.12E−05 | >1.00E−04 | 6.74E−06 | 5.07E−06 | 1.01E−05 | >1.00E−04 | >1.00E−04 |
| M14 | 2.59E−05 | 3.16E−05 | 4.51E−05 | >1.00E−04 | 5.83E−05 | >1.00E−04 | 1.96E−05 | >1.00E−04 | >1.00E−04 |
| SK-MEL-2 | 2.99E−05 | 3.41E−05 | >1.00E−04 | >1.00E−04 | 2.30E−05 | >1.00E−04 | 2.08E−05 | >1.00E−04 | 2.34E−05 |
| SK-MEL-28 | 2.81E−05 | 1.96E−05 | 3.40E−05 | >1.00E−04 | 2.91E−05 | >1.00E−04 | 3.37E−05 | >1.00E−04 | 9.38E−05 |
| SK-MEL-5 | 2.05E−05 | 2.90E−05 | 7.52E−05 | >1.00E−04 | 4.81E−05 | >1.00E−04 | 1.55E−05 | >1.00E−04 | 9.45E−05 |
| UACC-257 | 1.83E−05 | 2.20E−0S | 6.98E−05 | >1.00E−04 | 1.96E−05 | >1.00E−04 | 1.97E−05 | >1.00E−04 | >1.00E−04 |
| UACC-62 | 1.67E−05 | 1.23E−05 | 2.94E−05 | >1.00E−04 | 1.89E−05 | >1.00E−04 | 1.62E−05 | >1.00E−04 | 8.51E−05 |
| Ovarian Cancer | | | | | | | | | |
| IGROV1 | 1.75E−05 | 1.86E−05 | 1.52E−05 | >1.00E−04 | 1.73E−05 | >1.00E−04 | 1.65E−05 | >1.00E−04 | 3.96E−05 |
| OVCAR-3 | 1.65E−05 | 1.77E−05 | 2.55E−05 | >1.00E−04 | 2.36E−05 | 4.40E−05 | 3.57E−05 | >1.00E−04 | >1.00E−04 |
| OVCAR-4 | 1.14E−05 | 9.64E−06 | 6.46E−06 | >1.00E−04 | 8.96E−06 | | 2.56E−05 | >1.00E−04 | >1.00E−04 |
| OVCAR-5 | 3.11E−05 | 4.64E−05 | >1.00E−04 | >1.00E−04 | 3.12E−05 | >1.00E−04 | 3.44E−05 | >1.00E−04 | >1.00E−04 |
| OVCAR-8 | 1.48E−05 | 1.19E−05 | 6.05E−06 | >1.00E−04 | 1.08E−05 | 4.10E−06 | 2.62E−05 | 3.52E−05 | 6.00E−05 |
| SK-OV-3 | 1.72E−05 | 2.74E−05 | 2.48E−05 | >1.00E−04 | 1.68E−05 | >1.00E−04 | 4.99E−05 | 3.95E−05 | 4.42E−05 |
| Renal Cancer | | | | | | | | | |
| 786-0 | 1.06E−05 | 1.04E−05 | 1.61E−05 | >1.00E−04 | 1.33E−05 | 5.03E−06 | 3.09E−05 | 1.76E−05 | 3.96E−05 |
| A498 | | | | | | | 2.86E−05 | >1.00E−04 | |
| ACHN | 1.81E−05 | 1.45E−05 | 2.88E−05 | >1.00E−04 | 2.25E−05 | >1.00E−04 | 3.24E−05 | 9.79E−05 | >1.00E−04 |
| CAKI-1 | 1.78E−05 | 1.60E−05 | 2.28E−05 | >1.00E−04 | 2.23E−05 | >1.00E−04 | 2.80E−05 | >1.00E−04 | >1.00E−04 |
| RXF 393 | 2.98E−06 | 3.75E−06 | 5.25E−06 | >1.00E−04 | 8.66E−06 | 2.72E−06 | 2.75E−05 | 1.50E−05 | 1.51E−05 |
| TK-10 | 1.95E−05 | 1.31E−05 | 2.39E−05 | >1.00E−04 | 1.64E−05 | 4.58E−05 | 3.07E−05 | 7.82E−05 | 4.86E−05 |
| UO-31 | 2.33E−05 | 2.92E−05 | 6.29E−05 | >1.00E−04 | 3.48E−05 | >1.00E−04 | 3.62E−05 | >1.00E−04 | >1.00E−04 |
| Prostate Cancer | | | | | | | | | |
| PC-3 | 1.51E−05 | 1.07E−05 | 1.11E−05 | >1.00E−04 | 1.44E−05 | 1.24E−05 | 2.25E−05 | 3.10E−05 | 4.64E−05 |
| DU-145 | 1.47E−05 | 1.07E−05 | 1.63E−05 | >1.00E−04 | 2.57E−05 | 7.23E−05 | 2.78E−05 | 3.27E−05 | >1.00E−04 |

TABLE 31-continued

In Vitro Anti-Cancer Activity

| Panel/Cell Line | 111-157B | 111-178 | 111-183 | 111-184 | 111-190 | 111-191 | 111-192 | 111-194 | 111-204 |
|---|---|---|---|---|---|---|---|---|---|
| Breast Cancer | | | | | | | | | |
| MCF7 | 1.20E−05 | 4.42E−06 | 1.41E−05 | >1.00E−04 | 1.61E−05 | 4.23E−05 | 3.21E−05 | 5.52E−05 | 5.72E−05 |
| NCI/ADR-RES | 2.23E−05 | 1.80E−06 | 1.69E−05 | >1.00E−04 | 2.42E−05 | 1.89E−05 | 2.74E−05 | >1.00E−04 | >1.00E−04 |
| MDA-MB-231/ATCC | 1.79E−05 | 2.26E−05 | 3.37E−05 | >1.00E−04 | 2.18E−05 | 3.51E−05 | 3.23E−05 | 4.82E−05 | 3.20E−05 |
| HS 578T | 1.28E−05 | 1.58E−05 | 8.46E−06 | >1.00E−04 | 1.51E−05 | 7.36E−06 | 3.28E−05 | 6.44E−05 | 8.08E−05 |
| MDA-MB-435 | 1.91E−05 | 2.39E−05 | >1.00E−04 | >1.00E−04 | 3.72E−05 | >1.00E−04 | 2.13E−05 | >1.00E−04 | 3.39E−05 |
| MDA-N | 2.88E−05 | 3.10E−05 | >1.00E−04 | >1.00E−04 | 4.54E−05 | >1.00E−04 | 2.09E−05 | >1.00E−04 | 2.51E−05 |
| BT-549 | | 3.98E−05 | 3.32E−05 | >1.00E−04 | 6.84E−05 | >1.00E−04 | 2.46E−05 | >1.00E−04 | >1.00E−04 |

Example 37

Figure 24:
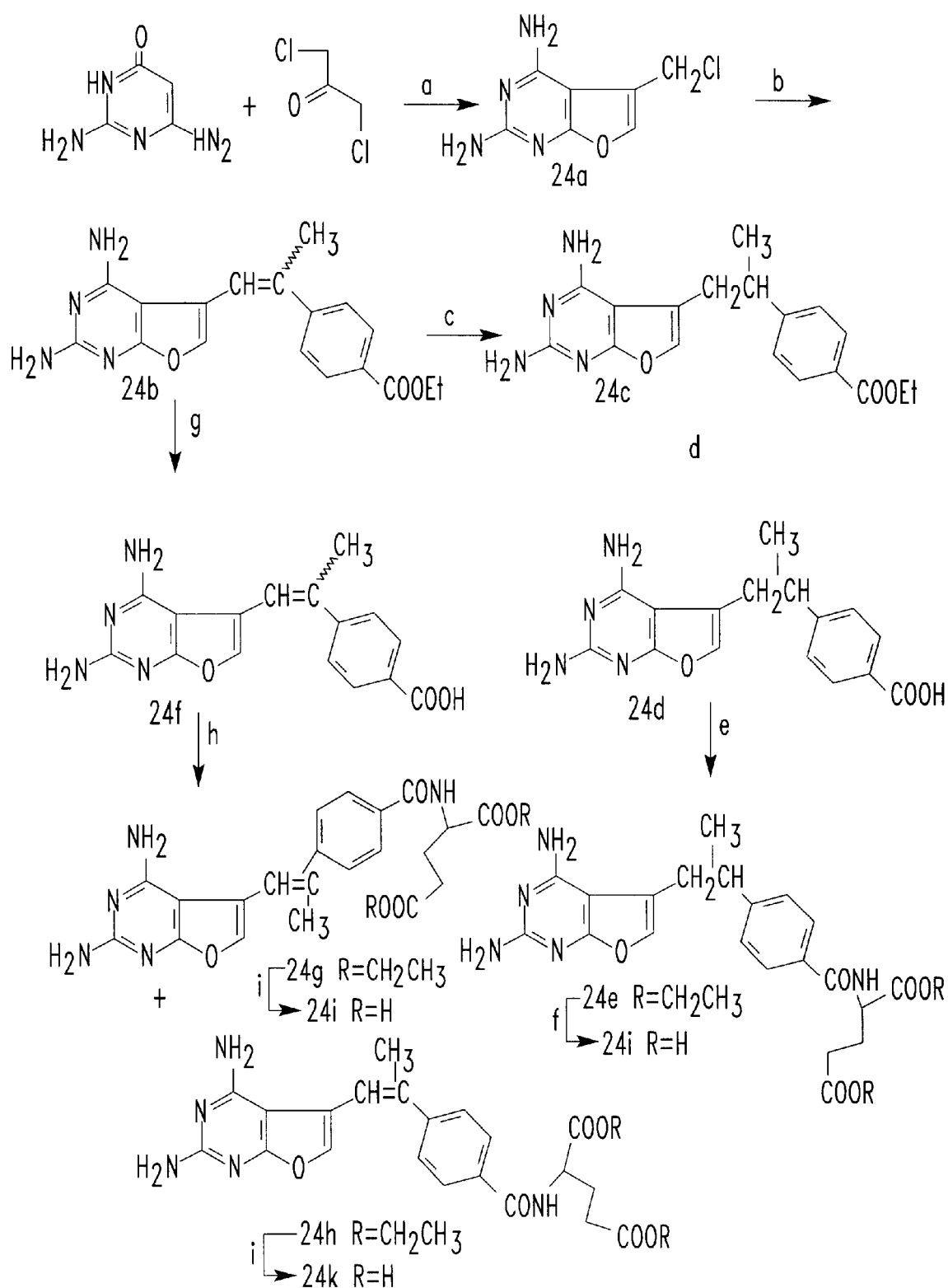
FIG. 24 shows a schematic diagram of the methods of preparing compounds having Formula 15, as described in Example 37.

Compounds corresponding to general formula 15 was synthesized using the method described below. Reference numerals and letters correspond with those shown in FIG. 24. The synthesized compounds were N-[4-[1-methyl-2-(2,4-diaminofuro[2,3-d]pyrimidin-5-yl)ethyl]benzyl]-L-glutamic acid 24i, and its regio-restricted E isomer 24j and Z isomer 24j.

Reagents and conditions used in the synthesis are as follows: a. DMF, r.t.; b. (i) Bu$_3$P/DMSO (ii) NaH (iii) ethyl-4-acetylbenzoate; c. 5% Pd-C/H$_2$, 45 psi, MeOH/CHCl$_3$/DMF; d. (i) 1N NaOH, DMSO/MeOH (ii) 1N H; e. iBuOCOCl, Et3N, Diethyl-L-glutamate; f. (i) 1N NaOH, DMSO/MeOH (ii) 1N HCl; g. same as d; h. same as e; i. same as f.

A Wittig type condensation of 2,4-diamino-5-(chloromethyl)furo[2,3-d]pyrimidine 24a with ethyl-4-acetyl-benzoate furnished the desired two-carbon bridged 9-methylfuro[2,3-d]- pyrimidine nucleus present in the target compounds as generally taught by Gangjee A. et al. presented at the 217 ACS National Meeting, Anaheim, Calif., Mar. 21–25, 1999, Abstract No. MEDI 049. The crucial intermediate 24a was readily obtained by the reaction of 2,6-diaminopyrimidin-4-one and dichloroacetone in DMF at room temperature as previously reported by Gangjee et al., J. Med. Chem. 41:1263–1271 (1998). Wittig condensation was first carried out by displacing the chloride with 3 eq of tributylphosphine and followed by 2.2 eq of sodium hydride in anhydrous dimethylsulfoxide to form a less sterically hindered ylide. This ylide was immediately condensed with the corresponding ethyl-4-acetyl-benzoate and after methanolic workup afforded the desired olefin 24b in 42% yield with both E and Z isomers. This was the common intermediate for the target molecules. E and Z isomer were assigned by the characteristic 6-CH chemical shift at 7.52 ppm for the E isomer, which is 0.85 ppm downfield from the Z isomer (6.67 ppm); this compares favorably with the previously reported trans and cis products. However, during the synthetic process some methyl ester exchange with ethyl ester was detected and the separation of excess tributylphosphine and phosphine oxide was also problematic. Reducing the amount of tributylphosphine and NaH to 1.5 eq, and using an ethanol workup instead of methanol, afforded the desired olefin in 65% yield (E:Z ratio 2:1) as determined by $^1$H NMR. Catalytic hydrogenation of the olefinic double bond of 24b was carried out under optimized conditions which included 3 eq (w/w) of 5% palladium on activated carbon as catalyst in methanol/chloroform/N,N-dimethylformamide (30:70:2), 45 psi of hydrogen and 4.5 h. After column chromatographic separation and recrystallization from methanol the desired 8,9-dihydro derivative 24c was obtained in 75% yield. Saponification of 24c with aqueous sodium hydroxide afforded the free acid 24d in 90% yield. Subsequent coupling of 24d with diethyl-L-glutamate went smoothly using isobutyl chloroformate as coupling agent and afforded the desired coupled product 24e in 85% yield. Final saponification with aqueous sodium hydroxide at room temperature followed by acidification to pH 4 in an ice bath afforded the pure target diacid 24i in 97% yield. The structure of 24i and the intermediates were confirmed by $^1$H NMR and elemental analysis.

The isolation of the conformational restricted E and Z isomer started from the E and Z mixture 24b from the Wittig reaction. It was more efficient to separate the E and Z mixture after coupling with the L-glutamate diester than prior to coupling. Thus hydrolysis of 24b with aqueous sodium hydroxide afforded the E, Z free acids 24f in 92% yield. Subsequent coupling of 24f with diethyl-L-glutamate went smoothly using isobutyl chloroformate as the coupling agent and afforded the desired coupled products 24g and 24h in 85% yield as an E, Z mixture. Separation of the E isomer 24g from the Z isomer 24h was achieved by recrystallization from the methanol/ethylacetate (1:1). The white crystals which separated were the pure E isomer as confirmed by high performance TLC and by its $^1$H NMR. The Z isomer remained in the filtrate. Final saponification with aqueous sodium hydroxide at room temperature followed by acidification to pH 4 in an ice bath afforded the pure target E-diacid 24j in 97%. The Z-diacid 24k obtained in 95% yield was contaminated with 20% of 24j as indicated by the $^1$H NMR.

Example 38

Compounds 24i, 24j and 24k prepared according to Example 37 were evaluated as inhibitors of L. casei DHFR, E. coli DHFR, T. gondii DHFR and human recombinant DHFR. Reference numbers again correspond with FIG. 24. The inhibitory concentration (IC$_{50}$) values are listed in Table 1 and compared with the previous reported values for methotrexate (MTX). The analogue 24i inhibited human recombinant DHFR with an IC$_{50}$ 0.42 $\mu$M. This inhibitory activity was about 20 fold less than that of MTX. The Z isomer 24k was five fold less potent than the reduced analogue 24i while the E isomer was only marginally active against human recombinant DHFR with an IC$_{50}$ of 42 $\mu$M. These three compounds were also evaluated as inhibitors of L. casei TS, E. coli TS, rat TS and human recombinant TS and were found to be weak inhibitors of these enzymes.

The target compounds 24i, 34j and 24k were also evaluated as inhibitors of the growth of leukemia CCRF-CEM cells in culture during continuous exposure (Table 32). The reduced compound 24i was highly cytotoxic and had an IC$_{50}$=29 nM which was similar to MTX. Interestingly, in the transport deficient cell line R2(Bos) compound 24i was about four times more potent than MTX indicating that transport is much more important for MTX than 24i. The 7.5-fold decrease in activity of 24i in the FPGS deficient cell line indicates that polyglutamylation of 24i does play a role in its cytotoxic activity. Again the pure E isomer was essentially inactive with $IC_{50}$=340 μM and the 80% Z isomer mixture ($IC_{50}$=12 μM) was much less potent than 24i.

TABLE 32

Growth Inhibition by compounds 24i–24k and MTX of CCRF-CEM Human Leukemia Cells, Its Methotrexate-resistant Sublines, Human Squamous Cell Carcinoma FaDu and A253 Cells During Continuous Exposure (0–120h)

| Cell line | Resistance mechanism | $EC_{50}$(nM) | | | |
|---|---|---|---|---|---|
| | | MTX | 24i | 24j | 24k |
| CCRF-CEM | Sensitive | 14.4 ± 1.0 (n = 5) | 29.2 ± 3.3 (n = 5) | 34000 ± 6000 (n = 2) | 1175 ± 83 (n = 4) |
| RI | Incr DHFR | 675 ± 35 (n = 2) | 685 ± 45 (n = 2) | nd | 32000 ± 1000 (n = 2) |
| R2(Bos) | Def Transport | 1600 ± 100 (n = 2) | 430 ± 60 (n = 2) | nd | 17000 ± 0 (n = 2) |
| R30dm | Decr FPGS | 14 ± 0 (n = 2) | 220 ± 20 (n = 2) | nd | 6400 ± 900 (n = 2) |
| FaDu | Sensitive | 11.3 ± 1.8 (n = 2) | 17.5 ± 0.5 (n = 2) | >10000 (n = 2) | 1400 ± 100 (n = 2) |
| A253 | Sensitive | 14.5 ± 0.5 (n = 2) | 28.5 ± 2.5 (n = 2) | >10000 (n = 2) | 700 ± 70 (n = 2) |

It will be appreciated by those skilled in the art that the present invention provides compounds, and pharmaceutically acceptable salts thereof, effective against infections caused by *Pneumocystis carinii, Toxoplasmosis gondii,* and other organisms, methods of preparing these compounds, and methods of using these compounds in a patient for therapeutic or prophylactic purposes. It will be further appreciated by those skilled in the art that this invention provides compounds, and pharmaceutically acceptable salts thereof, effective in reducing tumors or otherwise destroying cancerous cells in patients with cancer, methods of preparing these compounds, and methods of using these compounds in a patient for therapeutic purposes.

Whereas particular embodiments of this invention have been described above for purposes of illustration, it will be evident to those skilled in the art that numerous variations of the details of the present invention may be made without departing from the invention as defined in the appended claims.

What is claimed is:

1. A compound, and pharmaceutically acceptable salts, formulations and prodrugs of said compound, having the formula:

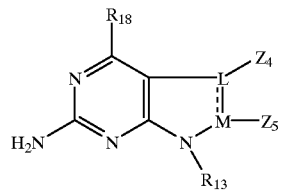

(14)

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $Z_4$ and $Z_5$ are different and are selected from the group consisting of $R_{14}$ and

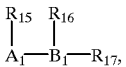

where $Z_4$ is $R_{14}$ when $Z_5$ is

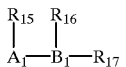

and $Z_4$ is

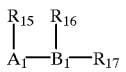

when $Z_5$ is $R_{14}$;
wherein $A_1$ is CH;
wherein $B_1$ is CH;
wherein $R_{13}$ is selected from the group consisting of H, a lower akyl group, a substituted or unsubstituted aralkyl group, and a substituted or unsubstituted aryl group;
wherein $R_{14}$ is selected from the group consisting of H, and a lower alkyl group;
wherein $R_{15}$ is selected from the group consisting of H and a lower alkyl group;
wherein $R_{16}$ is selected from the group consisting of H and a lower alkyl group;
wherein $R_{17}$ is selected from the group consisting of aryl, diaryl, triaryl, mono-, di- or tri-substituted aryl, mono-, di- or tri-substituted diaryl, mono-, di- or tri- substituted triaryl, a substituted or unsubstituted heteroaryl and p-aroyl-L-glutamate and each of said substituents is independently selected from the group consisting of a substituted or unsubstituted lower alkyl group, a substituted or unsubstituted alkoxy, a substituted or unsubstituted alkoxyaryloxy group and a halogen;
wherein $R_{18}$ is a lower akyl group; and
wherein each lower alkyl group is independently selected from the group consisting of lower alkyl groups having from about 1 to 6 carbons.

2. The compound of claim 1, wherein $R_{13}$ is selected from the group consisting of a benzyl group and hydrogen and wherein $R_{17}$ is selected from the group consisting of phenyl, methoxyphenyl, trimethoxyphenyl, and p-benzoyl-L-glutamate.

3. The compound of claim 2, wherein said methoxyphenyl is selected from the group consisting of 4-methoxyphenyl, 3-methoxyphenyl and 2-methoxyphenyl and said trimethoxyphenyl is 3,4,5-trimethoxyphenyl.

4. The compound of claim 3 wherein $R_{13}$ is benzyl and $R_{17}$ is 3-methoxyphenyl.

5. The compound of claim 3 wherein $R_{13}$ is H and $R_{17}$ is 2-methoxyphenyl.

6. The compound of claim 3 wherein $R_{13}$ is benzyl and $R_{17}$ is 3,4,5-trimethoxyphenyl.

7. A method of inhibiting dihydrofolate reductase and/or thymidylate synthase in a patient comprising the steps of:
   a) incorporating into a suitable pharmaceutical carrier a compound, or pharmaceutically acceptable salts, formulations and prodrugs of said compound, having the formula:

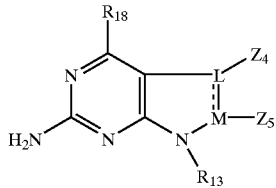

wherein L and M are selected from the group consisting of carbon and CH, the chemical bond between L and M is selected from the group consisting of a single bond and a double bond, L and M are carbon when the bond is a double bond, and L and M are CH when the bond is a single bond;
wherein $Z_4$ and $Z_5$ are different and are selected from the group consisting of $R_{14}$ and

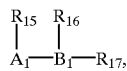

where $Z_4$ is $R_{14}$ when $Z_5$ is

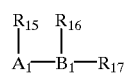

and $Z_4$ is

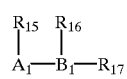

when $Z_5$ is $R_{14}$;
wherein $A_1$ is CH;
wherein $B_1$ is CH;
wherein $R_{13}$ is selected from the group consisting of H, a lower alkyl group, a substituted or unsubstituted aralkyl group, and a substituted or unsubstituted aryl group;
wherein $R_{14}$ is selected from the group consisting of H, and a lower alkyl group;
wherein $R_{15}$ is selected from the group consisting of H and a lower alkyl group;
wherein $R_{16}$ is selected from the group consisting of H and a lower alkyl group;
wherein $R_{17}$ is selected from the group consisting of aryl, diaryl, triaryl, mono-, di- or tri-substituted aryl, mono-, di- or tri-substituted diaryl, mono-, di- or tri- substituted triaryl, a substituted or unsubstituted heteroaryl and p-aryl-L-glutamate and each of said substituents is independently selected from the group consisting of a substituted or unsubstituted lower akyl group, a substituted or unsubstituted alkoxy, a substituted or unsubstituted alkoxyaryloxy group and a halogen;

wherein $R_{18}$ is a lower alkyl group; and wherein each lower alkyl group is selected from the group consisting of lower alkyl groups having from about 1 to 6 carbons; and b) administering an effective amount of said compound incorporated in said carrier to said patient.

8. The method of claim 7, wherein $R_{13}$ is selected from the group consisting of a benzyl group and hydrogen and wherein $R_{17}$ is selected from the group consisting of phenyl, methoxyphenyl, trimethoxyphenyl, and p-benzoyl-L-glutamate.

9. The method of claim 7, wherein L and M are both carbon, $A_2$ and $B_2$ are both carbon, and $R_{17}$ is selected from the group consisting of p-benzoyl-L-glutamate, phenyl, biphenyl, methoxyphenyl, dimethoxyphenyl, trimethoxyphenyl, chlorophenyl, dichlorophenyl, trichlorophenyl, naphthyl, methoxynaphthyl, and carbethoxyl phenyl.

10. The method of claim 8, wherein said carrier is selected from the group consisting of physiologic saline and 5% dextrose for injection.

11. The method of claim 8, including administering said compound by a method selected from the group consisting of parenteral administration, oral administration and topical administration.

12. The compound of claim 8 wherein $R_{13}$ is benzyl and $R_{17}$ is 3-methoxyphenyl.

13. The compound of claim 8 wherein $R_{13}$ is H and $R_{17}$ is 2-methoxyphenyl.

14. The compound of claim 8 wherein $R_{13}$ is benzyl and $R_{17}$ is 3,4,5-trimethoxyphenyl.

15. The method of claim 8, wherein the treatment is prophylactic and said illness is selected from the group consisting of infection caused by *Pneumocystis carinii* and *Toxoplasmosis gondii*.

16. The method of claim 7, wherein the treatment is therapeutic and said illness is selected from the group consisting of infection caused by *Pneumocystis carinii* and *Toxoplasmosis gondii*.

17. The method of claim 7, wherein the treatment is prophylactic and said illness is selected from the group consisting of infection caused by *Pneumocystis carinii* and *Toxoplasmosis gondii*.

18. The method of claim 7, wherein said carrier is selected from the group consisting of physiologic saline and 5% dextrose for injection.

19. The method of claim 7, including administering said compound by a method selected from the group consisting of parenteral administration, oral administration and topical administration.

20. The method of claim 7, wherein said methoxyphenyl is selected from the group consisting of 2-methoxyphenyl and 3-methoxyphenyl; said dimethoxyphenyl is selected from the group consisting of 3,4-dimethoxyphenyl and 2,5-dimethoxyphenyl; said trimethoxyphenyl is 3,4,5-trimethoxyphenyl; said chlorophenyl is selected from the group consisting of 2-chlropheny 1, 3-chlorophenyl and 4-chlorophenyl; said dichlorophenyl is selected from the group consisting of 3,4-dichlorophenyl, 2,5-dimethoxyphenyl, 2,4-dichlorophenyl; said trichlorophenyl is 2,3,4-tricholorophenyl; said methoxynaphthyl is 6-methoxynaphthyl and said carbethoxy phenyl is 4-carbethoxy phenyl.

21. The method of claim 8, wherein the treatment is therapeutic and said illness is selected from the group consisting of infection caused by *Pneumocystis carinii* and *Toxoplasmosis gondii*.

* * * * *